United States Patent
Kimura et al.

(10) Patent No.: US 8,008,293 B2
(45) Date of Patent: *Aug. 30, 2011

(54) BICYCLIC OXOMORPHOLINE DERIVATIVE

(75) Inventors: Teiji Kimura, Tsukuba (JP); Koki Kawano, Tsukuba (JP); Eriko Doi, Tsukuba (JP); Noritaka Kitazawa, Tsukuba (JP); Mamoru Takaishi, Tsukuba (JP); Koichi Ito, Tsukuba (JP); Toshihiko Kaneko, Tsukuba (JP); Takeo Sasaki, Tsukuba (JP); Nobuaki Sato, Tsukuba (JP); Takehiko Miyagawa, Tsukuba (JP); Hiroaki Hagiwara, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 113 days.

This patent is subject to a terminal disclaimer.

(21) Appl. No.: 12/522,281

(22) PCT Filed: Feb. 27, 2008

(86) PCT No.: PCT/JP2008/053887
§ 371 (c)(1),
(2), (4) Date: Jul. 7, 2009

(87) PCT Pub. No.: WO2008/108378
PCT Pub. Date: Sep. 12, 2008

(65) Prior Publication Data
US 2010/0113773 A1    May 6, 2010

Related U.S. Application Data

(60) Provisional application No. 60/891,997, filed on Feb. 28, 2007.

(30) Foreign Application Priority Data

Feb. 28, 2007 (JP) ................................. 2007-049085

(51) Int. Cl.
C07D 498/04 (2006.01)
A61K 31/5375 (2006.01)
(52) U.S. Cl. .................... 514/230.5; 544/105; 544/139; 514/235.8
(58) Field of Classification Search .................. 544/105, 544/139; 514/230.5, 235.8
See application file for complete search history.

(56) References Cited

U.S. PATENT DOCUMENTS

| | | |
|---|---|---|
| 3,470,167 A | 9/1969 | Sarkar |
| 3,989,816 A | 11/1976 | Rajadhyaksha |
| 4,910,200 A | 3/1990 | Curtze et al. |
| 5,281,626 A | 1/1994 | Oinuma et al. |
| 5,563,162 A | 10/1996 | Oku et al. |
| 5,804,577 A | 9/1998 | Hebeisen et al. |
| 5,985,856 A | 11/1999 | Stella et al. |
| 6,235,728 B1 | 5/2001 | Golik et al. |
| 6,306,870 B1 | 10/2001 | Bombrun et al. |
| 7,053,087 B1 | 5/2006 | Beatch et al. |
| 7,138,414 B2 | 11/2006 | Schoenafinger et al. |
| 7,300,936 B2 | 11/2007 | Parker et al. |
| 7,314,940 B2 | 1/2008 | Graczyk et al. |
| 7,618,960 B2 * | 11/2009 | Kimura et al. ............. 514/230.5 |
| 7,667,041 B2 | 2/2010 | Kimura et al. |
| 7,687,640 B2 | 3/2010 | Kimura et al. |
| 7,737,141 B2 | 6/2010 | Kimura et al. |
| 7,923,563 B2 | 4/2011 | Kushida et al. |
| 2001/0051642 A1 | 12/2001 | Ahn |
| 2002/0128263 A1 | 9/2002 | Mutel et al. |
| 2002/0183324 A1 | 12/2002 | Jacobson et al. |
| 2003/0195201 A1 | 10/2003 | Bo et al. |
| 2003/0208082 A1 | 11/2003 | Mutel et al. |
| 2003/0225070 A1 | 12/2003 | Mutel et al. |
| 2004/0006062 A1 | 1/2004 | Smallheer et al. |
| 2004/0034096 A1 | 2/2004 | Jolidon et al. |
| 2004/0038969 A1 | 2/2004 | Doherty et al. |
| 2004/0063770 A1 | 4/2004 | Ahn et al. |

(Continued)

FOREIGN PATENT DOCUMENTS

CN          1668593 A       9/2005

(Continued)

OTHER PUBLICATIONS

US Notice of Allowance, dated Jan. 12, 2010, for U.S. Appl. No. 11/715,440.
US Notice of Allowance, dated Sep. 27, 2010, for U.S. Appl. No. 12/721,952.
US Office Action, dated Oct. 4, 2010, for U.S. Appl. No. 12/301,428.
US Office Action, dated Sep. 14, 2009, for U.S. Appl. No. 11/715,440.
US Office Action, dated Sep. 30, 2010, for U.S. Appl. No. 11/663,550.
Supplementary European Search Report dated Apr. 7, 2010 for corresponding European Application No. 05743758.4.

(Continued)

*Primary Examiner* — Kahsay T Habte
(74) *Attorney, Agent, or Firm* — Birch, Stewart, Kolasch & Birch, LLP

(57) ABSTRACT

The present invention relates to a compound represented by formula (I):

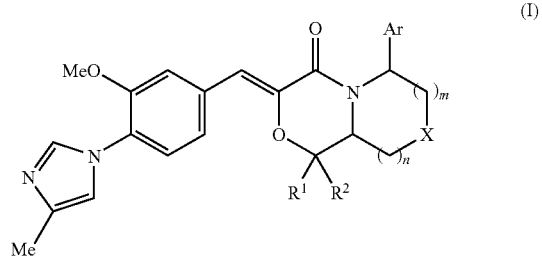

wherein $R^1$ represents a C1-3 alkyl group, $R^2$ represents a hydrogen atom or a C1-3 alkyl group, Ar represents a phenyl group or the like which may be substituted with 1 to 3 substituents, X represents an oxygen atom or the like, n and m are the same or different and integers of 0 to 2, or a pharmacologically acceptable salt, and use thereof as a medicament.

8 Claims, No Drawings

U.S. PATENT DOCUMENTS

| | | | |
|---|---|---|---|
| 2004/0087798 A1 | 5/2004 | Yamada |
| 2004/0127494 A1 | 7/2004 | Parker et al. |
| 2004/0127555 A1 | 7/2004 | Snow et al. |
| 2004/0152743 A1 | 8/2004 | Schoenafinger et al. |
| 2004/0192743 A1 | 9/2004 | Mjalli et al. |
| 2004/0235864 A1 | 11/2004 | Graczyk et al. |
| 2005/0070538 A1 | 3/2005 | Cheng et al. |
| 2005/0131043 A1 | 6/2005 | Mutel et al. |
| 2005/0187277 A1 | 8/2005 | Mjalli et al. |
| 2006/0004013 A1 | 1/2006 | Kimura et al. |
| 2007/0117798 A1 | 5/2007 | Kimura et al. |
| 2007/0117839 A1 | 5/2007 | Kimura et al. |
| 2007/0219181 A1 | 9/2007 | Kimura et al. |
| 2007/0249833 A1 | 10/2007 | Cheng et al. |
| 2008/0070902 A1 | 3/2008 | Kimura et al. |
| 2008/0085894 A1 | 4/2008 | Parker et al. |
| 2008/0096892 A1 | 4/2008 | Cheng et al. |
| 2008/0280948 A1 | 11/2008 | Baumann et al. |
| 2009/0048213 A1 | 2/2009 | Kimura et al. |
| 2009/0048448 A1 | 2/2009 | Kushida et al. |
| 2009/0203916 A1 | 8/2009 | Kushida et al. |
| 2009/0270623 A1 | 10/2009 | Shimomura et al. |

FOREIGN PATENT DOCUMENTS

| | | |
|---|---|---|
| DE | 3541716 A1 | 5/1987 |
| EP | 0219756 | 4/1987 |
| EP | 0 270 091 A1 | 6/1988 |
| EP | 0 589 491 A1 | 3/1994 |
| EP | 1 264 820 | 12/2002 |
| EP | 0 973 768 B1 | 7/2003 |
| EP | 1 757 591 A | 2/2007 |
| EP | 1 808 432 A1 | 7/2007 |
| EP | 1 953 151 A1 | 8/2008 |
| EP | 1 953 158 A1 | 8/2008 |
| EP | 1 992 618 A1 | 11/2008 |
| GE | P 200603920 B | 5/2006 |
| JP | 52-1035 A | 1/1977 |
| JP | 60-174781 A | 9/1985 |
| JP | 3-206042 A | 9/1991 |
| JP | 7-2780 A | 1/1995 |
| JP | 8283219 A | 10/1996 |
| JP | 9-132578 A | 5/1997 |
| JP | 10-510512 A | 10/1998 |
| JP | 11-228548 A | 8/1999 |
| JP | 11-513686 A | 11/1999 |
| JP | 3176365 B2 | 4/2001 |
| JP | 2001-508767 A | 7/2001 |
| JP | 2001-527083 A | 12/2001 |
| JP | 2003-206280 A | 7/2003 |
| JP | 2004-520292 A | 7/2004 |
| JP | 2004-531519 A | 10/2004 |
| JP | 2005-518371 A | 6/2005 |
| JP | 2005-526807 A | 9/2005 |
| JP | 2005-531596 A | 10/2005 |
| JP | 2005-533092 A | 11/2005 |
| JP | 2006-502247 A | 1/2006 |
| JP | 2006-518738 A | 8/2006 |
| JP | 2007-504282 A | 3/2007 |
| JP | 2007-523903 A | 8/2007 |
| RU | 2001126135 A | 7/2003 |
| SG | 145500 | 9/2007 |
| TW | 379224 B | 1/2000 |
| TW | 200400824 | 1/2004 |
| WO | WO 87/02587 A1 | 5/1987 |
| WO | WO-91/12237 A1 | 8/1991 |
| WO | WO 95/21832 A1 | 8/1995 |
| WO | WO-96/10559 A1 | 4/1996 |
| WO | 97/14417 A1 | 4/1997 |
| WO | WO-97/43287 | 11/1997 |
| WO | WO-98/03166 A1 | 1/1998 |
| WO | WO 98/09963 A1 | 3/1998 |
| WO | WO-98-24785 A1 | 6/1998 |
| WO | WO-00/07993 A1 | 2/2000 |
| WO | WO-00/50391 A1 | 8/2000 |
| WO | WO-00/51981 A1 | 9/2000 |
| WO | WO-01/68585 A1 | 9/2001 |
| WO | WO-01/81312 A2 | 11/2001 |
| WO | WO 03/022273 A1 | 3/2003 |
| WO | WO 03/027081 A2 | 4/2003 |
| WO | WO-03/053912 A1 | 7/2003 |
| WO | WO 03/062206 A2 | 7/2003 |
| WO | WO 03/074497 A1 | 9/2003 |
| WO | WO-03/082292 A1 | 10/2003 |
| WO | WO-03/101927 A1 | 12/2003 |
| WO | WO 2004/002478 A1 | 1/2004 |
| WO | WO-2004/007429 | 1/2004 |
| WO | WO-2004/07455 A1 | 1/2004 |
| WO | WO 2004/041776 A2 | 5/2004 |
| WO | WO 2004/089868 A1 | 10/2004 |
| WO | WO 2004-536084 A | 12/2004 |
| WO | WO-2005/020921 A2 | 3/2005 |
| WO | WO-2005/063754 A1 | 7/2005 |
| WO | WO 2005/072731 A1 | 8/2005 |
| WO | WO 2005/087767 A1 | 9/2005 |
| WO | WO-2005/115990 A1 | 12/2005 |
| WO | WO 2006/018662 A2 | 2/2006 |
| WO | WO-2006/046575 A1 | 5/2006 |
| WO | WO-2006/112550 A2 | 10/2006 |
| WO | WO-2007/034282 A2 | 3/2007 |
| WO | WO-2007/060810 A | 5/2007 |
| WO | WO-2007/060810 A1 | 5/2007 |
| WO | WO 2007/060821 A1 | 5/2007 |
| WO | WO-2007/102580 A1 | 9/2007 |
| WO | WO-2008/013213 A1 | 1/2008 |
| WO | WO-2008/097538 A1 | 8/2008 |
| WO | WO 2008/137102 A2 | 11/2008 |
| WO | WO-2008/137139 A1 | 11/2008 |
| WO | WO-2008/156580 A1 | 12/2008 |
| WO | WO-2009/020580 A1 | 2/2009 |

OTHER PUBLICATIONS

English abstract of GEP 20084571 B, published Jul. 10, 2008.
Search Report issued on Oct. 1, 2009, in connection with Georgian Patent Application No. AP 2007 010893.
Official Action issued Jan. 22, 2010, in Peruvian Patent Application No. 001480-2006.
Office Action issued Jan. 19, 2010, in copending U.S. Appl. No. 11/596,723.
Search Report issued May 27, 2009, in connection with Georgia Patent Application No. AP 2006 010709 (with English translation); 1 page.
S. M. Catalano et al., "The Role of Amyloid-Beta Derived Diffusible Ligands (ADDLs) in Alzheimer's Disease," Current Topics in Medicinal Chemistry, vol. 6, 597-608 (2006).
Official Action dated Jul. 4, 2008, which issued in corresponding Russian Patent Application No. 2006146070; 7 pages.
Official Action issued on Nov. 14, 2008, in corresponding Russian Patent Application No. 2006146070; 2 pages.
T. A. Comery, The Journal of Neuroscience, Sep. 28, 2005, 25(39): 8898-8902.
T. A. Comery et al., Society for Neuroscience Annual Meeting (2003), Abstracts, Program No. 525.21.
J. G. Varnes et al., Bioorganic & Medicinal Chemistry Letters, 14 (2004) 1645-1649.
H. Stark et al., Pharmazie 52 (1997), vol. 6, pp. 419-423.
M. Kajbaf et al., Journal of Chromatography, 575 (1992) 75-85.
S. L. Marcus, Cancer Research, 45, 112-115, Jan. 1995.
H. L. Yale, J. Med. Chem., 1966, 9(1), 42-46.
Guiroy et al., Acta Neuropathol (991) 82:87-92.
Ross, J. Med. Chem., 1973, vol. 16, No. 4, 347-352.
Office Action dated Sep. 16, 2008, that issued in connection with copending U.S. Appl. No. 11/594,150 (now abandoned).
Office Action dated Jul. 11, 2008, that issued in connection with copending U.S. Appl. No. 11/136,355.
Yuesong Gong et al.; Proceeding National Academy of Science, vol. 100, No. 18, pp. 10417-10422, Sep. 2, 2003.
Christoph Hock et al.; Neuron, vol. 38, No. 4, pp. 547-554, May 22, 2003.
Joseph T. Jarrett et al.; Biochemistry; vol. 32, No. 18, pp. 4693-4697, May 11, 1993.
George G. Glenner et al.; Biochemical and Biophysical Research Communications; vol. 120, No. 3, pp. 885-890, May 16, 1984.

Colin L. Masters et al.; Proceeding National Academy of Science; vol. 82, No. 12, pp. 4245-4249, Jun. 1985.

Gunnar K. Gouras et al; American Journal of Pathology, vol. 156, No. 1, pp. 15-20, Jan. 2000.

D. Scheuner et al.; Nature Medicine, vol. 2, No. 8, pp. 864-870, Aug. 1996.

Mark S. Forman et al.; The Journal of Biological Chemistry; vol. 272, No. 51, pp. 32247-32253, Dec. 19, 1997.

Mark S. Shearman et al.; Biochemistry; vol. 39, No. 30, pp. 8698-8704, 2000.

Huw D. Lewis et al.; Biochemistry, vol. 42, No. 24, pp. 7580-7586, 2003.

Thomas A. Lanz et al., The Journal of Pharmacology and Experimental Therapeutics; vol. 309, No. 1, pp. 49-55, 2004.

Gwendolyn T. Wong et al.; The Journal of Biological Chemistry, vol. 279, No. 13, pp. 12876-12882, Mar. 26, 2004.

John P. Blass; Journal of Neuroscience Research, vol. 66, No. 1, pp. 851-856, 2001.

Genevieve Evin et al.; NeuroReport; vol. 13, No. 5, pp. 719-723, Apr. 16, 2002.

Osamu Yasuhara et al.; Neuroscience Letters, vol. 171, Nos. 1 and 2, pp. 63-66, 1994.

Jan T. Teller et al.; Nature Medicine, vol. 2, No. 1, pp. 93-95, Jan. 1996.

Takahiko Tokuda et al.; Annals Neurology, vol. 41, No. 2, pp. 271-273, Feb. 1997.

Yorihide Hayashi et al.; Brain Research; vol. 789, No. 2, pp. 307-314, 1998.

Helene Barelli et al.; Molecular Medicine, vol. 3, No. 10, pp. 695-707, Oct. 1997.

Michael E. Calhoun et al.; Proceeding National Academy of Science, vol. 96, No. 24, pp. 14088-14093, Nov. 23, 1999.

B. Dermaut et al.; Brain, vol. 124, No. 12, pp. 2383-2392, 2001.

P. Cras et al.; Acta Neuropathol, vol. 96, No. 3, pp. 253-260, 1998.

Martin C. Herzig et al.; Nature Neuroscience, vol. 7, No. 9, pp. 954-960, Sep. 2004.

Sjoerd G. Van Duinen et al.; Proceeding National Academy of Science, vol. 84, No. 16, pp. 5991-5994, Aug. 1987.

Efrat Levy et al.; Science, vol. 248, No. 4959, pp. 1124-1126, Jun. 1, 1990.

Simon M. Laws et al.; Neurobiology of Aging, vol. 23, No. 1, pp. 55-58, 2002.

E. Vaucher et al.; Experimental Neurology, vol. 175, No. 2, pp. 398-406, 2002.

Dave Morgan et al.; Nature, vol. 408, No. 6815, pp. 982-985, Dec. 2000.

Paula M. Moran et al.; Proceeding National Academy of Science, vol. 92, No. 12, pp. 5341-5345, Jun. 1995.

Milla Koistinaho et al.; Proceeding National Academy of Science, vol. 99, No. 3, pp. 1610-1615, Feb. 5, 2002.

Fangyi Zhang et al.; The Journal of Neuroscience, vol. 17, No. 20, pp. 7655-7661, Oct. 15, 1997.

Marcin Sadowski et al.; Neurochemical Research, vol. 29, No. 6, pp. 1257-1266, Jun. 2004.

S. O'Riordan et al.; Neurology, vol. 59, No. 7, pp. 1108-1110, Oct. 2002.

Jochen Gehrmann et al.; GLIA; vol. 15, No. 2, pp. 141-151, 1995.

Wanda F. Reynolds et al.; Experimental Neurology, vol. 155, No. 1, pp. 31-41, 1999.

Douglas H. Smith et al.; NeuroMolecular Medicine, vol. 4, No. 1 and 2, pp. 59-72, 2003.

Miho Matsubara-Tsutsui et al.; American Journal of Medical Genetics, vol. 114, No. 3, pp. 292-298, 2002.

Marina D. Kirkitadze et al.; Journal of Neuroscience Research, vol. 69, No. 5, pp. 567-577, 2002.

Bernd O. Evert et al.; The Journal of Neuroscience, vol. 21, No. 15, pp. 5389-5396, Aug. 1, 2001.

D.M.A. Mann et al.; Neuroscience Letters, vol. 109, No. 1 and 2, pp. 68-75, 1990.

James Primavera et al.; Journal of Alzheimer's Disease, vol. 1, No. 3, pp. 183-193, 1999.

Benoit I. Giasson et al.; NeuroMolecular Medicine, vol. 4, No. 1 and 2, pp. 49-58, 2003.

Eliezer Masliah et al.; Proceeding National Academy of Science; vol. 98, No. 21, pp. 12245-12250, Oct. 9, 2001.

Marta Barrachina et al.; Neurochemistry International; vol. 46, No. 3, pp. 253-260, 2005.

M.L. Schmidt et al.; Acta Neuropathol, vol. 95, No. 2, pp. 117-122, 1998.

H. Ito et al.; Neuropathology and Applied Neurobiology, vol. 17, No. 5, pp. 365-373, 1991.

S.M. Rosso et al.; Annals of the New York Academy of Science, vol. 920, pp. 115-119, 2000.

M. Tolnay et al.; Neuropathology and Applied Neurobiology, vol. 25, No. 4, pp. 295-305, 1999.

Lee-Way Jin et al.; American Journal of Pathology, vol. 164, No. 3, pp. 975-985, Mar. 2004.

Shoichi Sasaki et al.; Acta Neuropathol, vol. 97, No. 5, pp. 463-468, 1999.

A. Tamaoka et al.; Journal of Neurology, vol. 247, No. 8, pp. 633-635, 2000.

Ronald L. Hamilton et al.; Acta Neuropathol, vol. 107, No. 6, pp. 515-522, 2004.

Bradley J. Turner et al.; Neurochemical Research, vol. 29, No. 12, pp. 2281-2286, Dec. 2004.

Roy O. Weller; Journal of Neuropathology and Experimental Neurology, vol. 57, No. 10, pp. 885-894, Oct. 1998.

Gerald D. Silverberg et al.; Lancet Neurology, vol. 2, No. 8, pp. 506-511, Aug. 2003.

Roy O. Weller et al.; Annals of the New York Academy of Science, vol. 903, pp. 110-117, 2000.

H.Y. Yow et al.; Neuropathology and Applied Neurobiology; vol. 28, p. 149, 2002.

Roy O. Weller et al.; Annals of the New York Academy of Science, vol. 977, pp. 162-168, 2002.

Margaret J. Smith et al.; Annals of Neurology, vol. 49, No. 1, pp. 125-129, 2001.

Richard Crook et al.; Nature Medicine, vol. 4, No. 4, pp. 452-455, Apr. 1998.

Craig S. Atwood, Brain Research Review; vol. 43, No. 1, pp. 164-178, 2003.

Jonathan D. Lowenson et al.; Trends in Cardiovascular Medicine, vol. 4, No. 1, pp. 3-8, 1994.

Andrew B. Singleton et al.; vol. 123, No. 12, pp. 2467-2474, 2000.

W.F. Gattaz et al.; Journal of Neural Transmission, vol. 111, No. 5, pp. 591-601, 2004.

A. Assini et al.; Neurology, vol. 63, No. 5, pp. 828-831, Sep. 2004.

Guido R.Y. DeMeyer et al.; Circulation Research, vol. 90, No. 11, pp. 1197-1204, 2002.

Masahiko Kato et al., Chem. Pharm. Bull., 42 (12), 2546-2555 (1994).

Japanese Patent Office (JPO) Office Action dated Sep. 28, 2007, issued in a corresponding Japanese application No. 2006-513906 for U.S. Appl. No. 11/136,355, (with English language translation).

English translation of Office Action dated Apr. 11, 2008, that issued in copending Pakistan Patent Application No. 1435/2006.

Office Action dated Feb. 24, 2009, issued in copending Singapore Application No. 200803192-4.

Office Action dated Feb. 11, 2009, issued in copending Singapore Application No. 200803266-6.

Supplemental Search Report issued on Apr. 24, 2009, in corresponding European Patent Application No. 05 80 5284.6.

Office Action issued on Apr. 3, 2009, in copending U.S. Appl. No. 11/594,130.

Office Action issued on Apr. 1, 2009, in copending U.S. Appl. No. 12/200,731.

Chen et al., "Preparation of cyclosporine A nanoparticles by evaporative precipitation into aqueous solution," International Journal of Pharmaceutics, vol. 242, pp. 3-14, 2002.

Eurasian Official Action, dated Mar. 12, 2010, for Eurasian Application No. 200870336/28.

Extended European Search Report, dated Aug. 4, 2010, for European Application No. 06822806.3.

International Search Report, dated Jan. 23, 2007, for PCT Application No. PCT/JP2006/322982.

Lieberman et al., "Pharmaceutical Dosage Forms," Tablets, Second Edition, Bioavailability in Tablet Technology, vol. 2, pp. 462-465, 1990.

Lipinski, "Solubility in Water and DMSO: Issues and Potential Solutions," Pharmaceutical Profiling in Drug Discovery for Lead Selection, American Association of Pharmaceutical Scientists, pp. 93-125, 2004.

Tietze et al., "Jikken Manual," Nankodo Co., Ltd., pp. 196-199, Jan. 15, 1995.

US Notice of Allowance, dated Aug. 20, 2010, for U.S. Appl. No. 12/200,731.

US Notice of Allowance, dated Sep. 20, 2010, for U.S Appl. No. 11/596,723.

US Office Action, dated Mar. 9, 2010, for U.S. Appl. No. 12/200,731.

International Search Report for International Appl. No. PCT/JP2008/053887, mailed Sep. 19, 2008.

Office Action from Russian Patent Appl. No. 2008125426/04(030920), date Jun. 1, 2009.

Office Action from U.S. Appl. No. 11/715,440, dated Jul. 16, 2009.

Office Action from U.S. Appl. No. 12/200,731, dated Jul. 30, 2009.

Written Opinion issued Jan. 27, 2011, in Singapore Patent Application No. 201000682-3.

Horig et al., "From bench to clinic and back: Perspective on the 1st IQPC Translational Research Conference," Journal of Translational Medicine 2004, vol. 2, No. 44.

Office Action issued Jan. 24, 2011, in copending U.S. Appl. No. 12/301,428.

Office Action issued Nov. 12, 2010, in Chinese Patent Application No. 200780018090.5 (with English translation).

Schafer et al., "Failure is an option: learning from unsuccessful proof-of-concept trials," Drug Discovery Today 2008, vol. 13, Nos. 21/22, pp. 913-916.

Extended European Search Report, dated Jan. 26, 2011, for European Application No. 07743622.8.

US Office Action, dated Feb. 15, 2011, for U.S. Appl. No. 12/301,421.

"Studies Demonstrate Link Among Alzheimer's Disease, Down Syndrome and Atherosclerosis," Science Daily, Jan. 15, 2010, http://www.sciencedaily.com/releases/2010/01/100115182639.htm, downloaded Mar. 28, 2011.

Fergus, "Alzheimer's Disease and Down Syndrome: Connections Between Alzheimer's Disease and Down Syndrome," http://downsyndrome.about.com/od/medicalissuesinds/a/DSAlzheimers_ro.htm, downloaded Mar. 28, 2011.

Hardy et al., "The Amyloid Hypothesis of Alzheimer's Disease: Progress and Problems on the Road to Therapeutics," Science, 2002, vol. 297, pp. 353-356.

Office Action issued Apr. 6, 2011, in copending U.S. Appl. No. 12/403,565.

Rafii et al., "Recent Developments in Alzheimer's Disease Therapeutics," BMC Medicine, 2009, vol. 7, No. 7, pp. 1-4.

Brocchini et al., "Preparation of piperazinedione-derivative inhibitors of plasminogen activator inhibitor," Database CA [Online] Chemical Abstracts Service, Columbus, Ohio, US, XP002574973, retrieved from STN, Database accession No. 1995:994197, Abstract (1995; downloaded Mar. 24, 2010).

Database Crossfire Beilstein, Beilstein Institut Zur Foerderung Der Chemischen Wissenschaften, Frankfurt Am Maine, DE, XP002574972, Database accession No. 4617764, Abstract (Jan. 2010; downloaded Mar. 24, 2010).

Chinese Office Action, dated May 11, 2011, for Chinese Application No. 200680043109.7 (with English translation).

Cooper et al., "1,4-Dihydropyridines as antagonists of platelet activating factor. 1. Synethesis and structure-activity realtionships of 2-(4-heterocyclyl)phenyl derivatives," J. Med. Chem. (1992), vol. 35, pp. 3115-3129, XP-002399013.

Davey et al., "Novel compounds posessing potent cAMP and cGMP phosphodiesterase inhibitory activity. Synthesis and cardiovascular effects of a series of . . . ," J. Med. Chem. (1991) vol. 34, pp. 2671-2677.

Erhardt et al., "Cardiotonic Agents. 5. Fragments from the heterocycle-phenyl-imidazole pharmacophore," J. Med. Chem. (1989) vol. 32, pp. 1173-1176.

European Search Report issued May 17, 2011, in European Patent Application No. 10177579.9.

Higaki et al., "A Combinatorial Approach to the Identification of Dipeptide Aldehyde Inhibitors of Beta-Amyloid Production," J. Med. Chem. 1999, vol. 42, pp. 3889-3898.

Kimura et al., CAPLUS Accession No. 2005:1290311 (2005).

Mano et al., "Novel imidazole compounds as a new series of potent, orally active inhibitors of 5-Lipoxygenase," Bioorganic and Medicinal Chemistry (2003), vol. 11, pp. 3879-3887, XP-002635592.

Mědiarové et al., "Ultrasound effect on the aromatic nucleophilic substitution reactions on some haloarenes," Ultrasonics Sonochemistry (2003) vol. 10, pp. 265-270.

Office Action issued Apr. 20, 2011, in Chinese Patent Application No. 200880006622.8 (with English translation).

Office Action issued Jun. 10, 2011, in copending U.S. Appl. No. 12/093,929.

Office Action issued Jun. 21, 2011, in copending U.S. Appl. No. 12/093,287.

Office Action issued May 12, 2011, in European Patent Application No. 05 743 758.4.

Office Action issued May 24, 2011, in Japanese Patent Application No. 2007-306088 (with English translation).

Search Report and Substantive Examination Report issued in May. 2011, in El Salvador Patent Application No. 2913/08 (with English translation).

Sitkina et al., "Direct N-arylation of 5-membered heterocyclic nitrogen rings," Chemistry of Heterocyclic Compounds (1966) vol. 2, No. 1, pp. 103-105.

Office Action issued May 11, 2011, in Australian Patent Application No. 2006317468.

Office Action issued May 20, 2011, in Chinese Patent Application No. 200680043648.0 (with English translation).

Office Action issued May 9, 2011, in Australian Patent Application No. 2007223158.

* cited by examiner

BICYCLIC OXOMORPHOLINE DERIVATIVE

This application is the National Phase of PCT/JP2008/053887 filed on Feb. 27, 2008, which claims priority under 35 U.S.C. 119(e) to U.S. Provisional Application No. 60/891,997 filed on Feb. 28, 2007 and under 35 U.S.C. 119(a) to Patent Application No. JP 2007-049085 filed in Japan on Feb. 28, 2007, all of which are hereby expressly incorporated by reference into the present application.

TECHNICAL FIELD

The present invention relates to a bicyclic oxomorpholine derivative and a drug containing the same as an active ingredient. The present invention more particularly relates to a bicyclic cinnamide compound containing a non-peptide morpholine residue and an amyloid beta (hereinafter referred to as Aβ) production decreasing agent containing the same as an active ingredient which is effective particularly for the treatment of neurodegenerative diseases caused by Aβ, such as Alzheimer's disease and Down's syndrome.

BACKGROUND ART

Alzheimer's disease is a disease characterized by nerve cell degeneration and loss as well as formation of senile plaques and neurofibrillary change. Currently, treatment of Alzheimer's disease is limited to symptomatic treatment using symptom improving agents represented by acetylcholine esterase inhibitors, and no basic remedy for suppressing progression of the disease has been developed. Development of a method for controlling the cause of the pathological conditions is necessary to create a basic remedy for Alzheimer's disease.

It is thought that the Aβ protein, which is a metabolite of amyloid precursor protein (hereinafter, referred to as APP), is closely involved in degeneration and loss of nerve cells and further development of dementia symptoms (for example, refer to Non-patent document 1 and Non-patent document 2). The major components of the Aβ protein are Aβ40, which consists of 40 amino acids, and Aβ42, which has two more amino acids at the C terminus. These Aβ40 and Aβ42 have a high agglutination property (for example, refer to Non-patent document 3) and are the major components of a senile plaque (for example, refer to Non-patent document 3, Non-patent document 4, and Non-patent document 5). Further, mutation of the APP and presenilin genes observed in familial Alzheimer's disease is known to increase these Aβ40 and Aβ42 (for example, refer to Non-patent document 6, Non-patent document 7, and Non-patent document 8). Therefore, compounds that decrease production of Aβ40 and Aβ42 are expected as drugs for suppressing progression of or preventing Alzheimer's disease.

Aβ is generated by cleavage of APP by beta secretase followed by excision by gamma secretase. Based on this, development of inhibitors of gamma secretase or beta secretase has been attempted for the purpose of suppressing production of Aβ. Many of these known secretase inhibitors are peptides or peptide mimetics such as, for example, L-685458 (for example, refer to Non-patent document 9) and LY-411575 (for example, refer to Non-patent document 10, Non-patent document 11, and Non-patent document 12).

[Non-patent document 1] Klein W L, and 7 others, Alzheimer's disease-affected brain: Presence of oligomeric Aβ ligands (ADDLs) suggests a molecular basis for reversible memory loss, Proceedings of the National Academy of Science USA 2003, Sep. 2; 100(18), p. 10417-10422

[Non-patent document 2] Nitsch R M, and 16 others, Antibodies against β-amyloid slow cognitive decline in Alzheimer's disease, Neuron, 2003, May 22; 38, p. 547-554

[Non-patent document 3] Jarrett J T, and 2 others, The carboxy terminus of the β amyloid protein is critical for the seeding of amyloid formation: Implications for the pathogenesis of Alzheimer's disease, Biochemistry, 1993, 32(18), p. 4693-4697

[Non-patent document 4] Glenner G G, and another, Alzheimer's disease: initial report of the purification and Characterization of a novel cerebrovascular amyloid protein, Biochemical and biophysical Research Communications, 1984, May 16, 120(3), p. 885-890

[Non-patent document 5] Masters C L, and 5 others, Amyloid plaque core protein in Alzheimer's disease and Down's syndrome, Proceedings of the National Academy of Science USA, 1985, June, 82(12), p. 4245-4249

[Non-patent document 6] Gouras G K, and 11 others, Intraneuronal Aβ42 accumulation in human brain, American Journal of Pathology, 2000, January, 156(1), p. 15-20

[Non-patent document 7] Scheuner D, and 20 others, Secreted amyloid β-protein similar to that in the senile plaques of Alzheimer's disease is increased in vivo by the presenilin 1 and 2 and APP mutations linked to familial Alzheimer's disease, Nature Medicine, 1996, August, 2(8), p. 864-870

[Non-patent document 8] Forman M S, and 4 others, Differential effects of the Swedish mutant amyloid precursor protein on β-amyloid accumulation and secretion in neurons and normeuronal cells, The Journal of Biological Chemistry, 1997, Dec. 19; 272(51), p. 32247-32253

[Non-patent document 9] Shearman M S, and 9 others, L-685458, an Aspartyl Protease Transition State Mimic, Is a Potent Inhibitor of Amyloid β-Protein Precursor γ-Secretase Activity, Biochemistry, 2000, Aug. 1; 39(30), p. 8698-8704

[Non-patent document 10] Shearman M S, and 6 others, Catalytic Site-Directed γ-Secretase Complex Inhibitors Do Not Discriminate Pharmacologically between Notch S3 and β-APP Cleavages, Biochemistry, 2003, Jun. 24; 42(24), p. 7580-7586

[Non-patent document 11] Lanz T A, and 3 others, Studies of Aβ pharmacodynamics in the brain, cerebrospinal fluid, and plasma in young (plaque-free) Tg2576 mice using the γ-secretase inhibitor N2-[(2S)-2-(3,5-difluorophenyl)-2-hydroxyethanoyl]-N1-[(7S)-5-methyl-6-oxo-6,7-dihydro-5H-dibenzo[b,d]azepin-7-yl]-L-alaninamide (LY-411575), The journal of Pharmacology and Experimental Therapeutics, 2004, April; 309(1), p. 49-55

[Non-patent document 12] Wong G T, and 12 others, Chronic treatment with the γ-secretase inhibitor LY-411575 inhibits β-amyloid peptide production and alters lymphopoiesis and intestinal cell differentiation, The Journal of Biological Chemistry, 2004, Mar. 26; 279(13), p. 12876-12882

DISCLOSURE OF INVENTION

Problems to be Solved by the Invention

As described above, compounds suppressing the production of Aβ40 and Aβ42 from APP are expected as agents for therapeutic or prophylactic treatment of diseases attributable to Aβ represented by Alzheimer's disease. However, no non-peptide compound is known which suppresses the production of Aβ40 and Aβ42 and has excellent drug efficacy. Therefore, novel low molecular weight compounds suppressing the production of Aβ40 and Aβ42 are being awaited.

Means for Solving the Problems

The present inventors conducted various research. As a result, for the first time, they discovered a non-peptide bicyclic morpholine type cinnamide compound that suppresses the production of Aβ40 and 42 from APP, and found an agent for prophylactic or therapeutic treatment of diseases attributable to Aβ represented by Alzheimer's disease. Thus, the present invention was accomplished.

That is, the present invention relates to the followings:
1) A compound represented by the following formula (I):

[Formula 1]

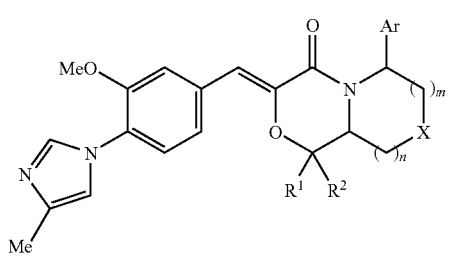

(I)

wherein (1) R¹ represents a C1-3 alkyl group, R² represents a hydrogen atom or a C1-3 alkyl group, or (2) R¹ and R², together with the carbon atom to which they are attached, form a C3-6 cycloalkyl group, Ar represents a phenyl group which may be substituted with 1 to 3 substituents that are the same or different and selected from substituent group A1 or a pyridinyl group which may be substituted with 1 to 3 substituents that are the same or different and selected from substituent group A1, X represents a methylene group which may be substituted with 1 or 2 substituents selected from substituent group A1 or a vinylene group which may be substituted with 1 or 2 substituents selected from substituent group A1, an oxygen atom, or an imino group which may be substituted with a C1-6 alkyl group or a C1-6 acyl group, and n and m are the same or different and integers of 0 to 2, or a pharmacologically acceptable salt thereof;

Substituent group A1: (1) a halogen atom, (2) a hydroxyl group, (3) a cyano group, (4) a C3-8 cycloalkyl group, (5) a C3-8 cycloalkoxy group, (6) a C1-6 alkyl group (the C1-6 alkyl group may be substituted with 1 to 5 halogen atoms or 1 to 3 C1-6 alkoxy groups), (7) an amino group which may be substituted with 1 or 2 C1-6 alkyl groups (the C1-6 alkyl group may be substituted with 1 to 5 halogen atoms), (8) a C1-6 alkoxy group (the C1-6 alkoxy group may be substituted with 1 to 5 halogen atoms), and (9) a carbamoyl group which may be substituted with 1 or 2 C1-6 alkyl groups (the C1-6 alkyl group may be substituted with 1 to 3 halogen atoms).

2) The compound or a pharmacologically acceptable salt thereof according to 1), wherein X represents a methylene group (the methylene group may be substituted with 1 or 2 substituents that are the same or different and selected from the group consisting of C1-6 alkyl groups and hydroxyl group), and n and m are 1.

3) The compound or a pharmacologically acceptable salt thereof according to 1), wherein X represents an oxygen atom, and n and m are 1.

4) The compound or a pharmacologically acceptable salt thereof according to 1), wherein X represents a methylene group, n is 1, and m is 0.

5) The compound or a pharmacologically acceptable salt thereof according to 1), wherein Ar represents a phenyl group substituted with 1 to 3 halogen atoms.

6) The compound or a pharmacologically acceptable salt thereof according to 1), which is selected from the following group:

1) (Z)-(1R,6R,9aR)-3-[3-Methoxy-4-(4-methylimidazol-1-yl)benzylidene]-1-methyl-6-(3,4,5-trifluorophenyl)tetrahydro-[1,4]oxazino[3,4-c][1,4]oxazin-4-one, 2) (Z)-(1S,6R,9aR)-3-[3-Methoxy-4-(4-methylimidazol-1-yl)benzylidene]-1-methyl-6-(3,4,5-trifluorophenyl)tetrahydro-[1,4]oxazino[3,4-c][1,4]oxazin-4-one, 3) (Z)-(1S,6R,9aR)-6-(3,4-Difluoro-phenyl)-3-[3-methoxy-4-(4-methylimidazol-1-yl)benzylidene]-1-methyltetrahydro-[1,4]oxazino[3,4-c][1,4]oxazin-4-one, 4) (Z)-(6S,8aR)-6-(4-Fluorophenyl)-3-[3-methoxy-4-(4-methylimidazol-1-yl)benzylidene]-1,1-dimethyltetrahydropyrrolo[2,1-c][1,4]oxazin-4-one, 5) (Z)-(1S,6R,9aR)-3-[3-Methoxy-4-(4-methylimidazol-1-yl)benzylidene]-1-methyl-6-(4-chlorophenyl)hexahydropyrido[2,1-c][1,4]oxazin-4-one, 6) (Z)-(1S,6S,8aR)-6-(4-Fluorophenyl)-3-[3-methoxy-4-(4-methylimidazol-1-yl)benzylidene]-1-methyltetrahydropyrrolo[2,1-c][1,4]oxazin-4-one, 7) (Z)-(1R,6S,8aR)-6-(4-Fluorophenyl)-3-[3-methoxy-4-(4-methylimidazol-1-yl)benzylidene]-1-methyltetrahydropyrrolo[2,1-c][1,4]oxazin-4-one, 8) (Z)-(6S,8aR)-6-(4-Chlorophenyl)-3-[3-methyloxy-4-(4-methylimidazol-1-yl)benzylidene]-1,1-dimethyltetrahydropyrrolo[2,1-c][1,4]oxazin-4-one, 9) (Z)-(1S,6S,8aR)-6-(4-Chlorophenyl)-3-[3-methoxy-4-(4-methylimidazol-1-yl)benzylidene]-1-methyltetrahydropyrrolo[2,1-c][1,4]oxazin-4-one, 10) (Z)-(1R,6S,8aR)-6-(4-Chlorophenyl)-3-[3-methoxy-4-(4-methylimidazol-1-yl)benzylidene]-1-methyltetrahydropyrrolo[2,1-c][1,4]oxazin-4-one, 11) (Z)-(6S,8aR)-3-[3-Methoxy-4-(4-methylimidazol-1-yl)benzylidene]-1,1-dimethyl-6-(3,4,5-trifluorophenyl)tetrahydropyrrolo[2,1-c][1,4]oxazin-4-one, 12) (Z)-(1S,6S,8aR)-3-[3-Methoxy-4-(4-methylimidazol-1-yl)benzylidene]-1-methyl-6-(3,4,5-trifluorophenyl)tetrahydropyrrolo[2,1-c][1,4]oxazin-4-one, 13) (Z)-(1R,6S,8aR)-3-[3-Methoxy-4-(4-methylimidazol-1-yl)benzylidene]-1-methyl-6-(3,4,5-trifluorophenyl)tetrahydropyrrolo[2,1-c][1,4]oxazin-4-one, 14) (Z)-(6S,8aR)-6-(3,4-Difluoro-phenyl)-3-[3-methoxy-4-(4-methylimidazol-1-yl)benzylidene]-1,1-dimethyltetrahydropyrrolo[2,1-c][1,4]oxazin-4-one, 15) (Z)-(1S,6S,8aR)-6-(3,4-Difluoro-phenyl)-3-[3-methoxy-4-(4-methylimidazol-1-yl)benzylidene]-1-methyltetrahydropyrrolo[2,1-c][1,4]oxazin-4-one, 16) (Z)-(1R,6S,9aR)-3-[3-Methoxy-4-(4-methylimidazol-1-yl)benzylidene]-1-methyl-6-(3,4,5-trifluorophenyl)hexahydropyrido[2,1-c][1,4]oxazin-4-one, 17) (Z)-(1S,6S,9aR)-3-[3-Methoxy-4-(4-methylimidazol-1-yl)benzylidene]-1-methyl-6-(3,4,5-trifluorophenyl)hexahydropyrido[2,1-c][1,4]oxazin-4-one, 18) (Z)-(6S,8aR)-3-[3-Methoxy-4-(4-methylimidazol-1-yl)benzylidene]-1,1-cyclopropyl-6-(3,4,5-trifluorophenyl)tetrahydropyrrolo[2,1-c][1,4]oxazin-4-one, and 19) (6R,9aR)-3-[1-[3-methoxy-4-(4-methyl-1H-imidazol-1-yl) phenyl-(Z)-methylidene]-1,1-dimethyl-6-(3,4,5-trifluorophenyl)tetrahydro [1,4]oxazino[3,4-c][1,4]oxazin-4-one.

7) A drug containing the compound or a pharmacologically acceptable salt according to any one of 1) to 6) as an active ingredient.

8) The drug according to 7) for prophylactic or therapeutic treatment of a disease attributable to amyloid beta.

9) The drug according to 8), wherein the disease attributable to amyloid beta is Alzheimer's disease, senile dementia, Down's syndrome, or amyloidosis.

The compound represented by the general formula (I) or a pharmacologically acceptable salt thereof and the agent for prophylactic or therapeutic treatment of a disease attributable to Aβ of the present invention are novel inventions that have not been listed in the literature.

Hereafter, the present invention will be explained in detail with explanation of meanings of symbols, terms, and the like used in the present specification.

In the present specification, the structural formula of a compound may represent a specific isomer for the sake of convenience. However, the present invention includes all geometrical isomers, isomers such as optical isomers, stereoisomers, and tautomers based on an asymmetric carbon, and isomer mixtures that exist based on the structure of the compound and is not limited by the expression of a formula used for the sake of convenience. The compound may be one of the isomers or a mixture thereof. Therefore, it is possible that the compound may have asymmetric carbon atoms in a molecule, and optically active substances and racemates may exist, but the present invention is not limited to any of these and includes all of them. Further, crystal polymorphs may exist but are not limited similarly. The compound may be any of single crystal forms or a mixture thereof, or may be a hydrate as well as an anhydrate.

The term "diseases attributable to Aβ" includes a wide variety of conditions such as Alzheimer's disease (for example, refer to, Klein W L, and 7 others, Alzheimer's disease-affected brain: Presence of oligomeric Aβ ligands (ADDLs) suggests a molecular basis for reversible memory loss, Proceeding National Academy of Science USA, 2003, Sep. 2, 100 (18), p. 10417-10422; Nitsch R M, and 16 others, Antibodies against β-amyloid slow cognitive decline in Alzheimer's disease, Neuron, 2003, May 22, 38 (4), p. 547-554: Jarrett J T, and 2 others, The carboxy terminus of the β amyloid protein is critical for the seeding of amyloid formation: Implications for the pathogenesis of Alzheimer's disease, Biochemistry, 1993, May 11, 32 (18), p. 4693-4697; Glenner G G, and another, Alzheimer's disease; initial report of the purification and characterization of a novel cerebrovascular amyloid protein, Biochemical and biophysical research communications, 1984, May 16, 120 (3), p. 885-890; Masters C L, and 6 others, Amyloid plaque core protein in Alzheimer disease and Down syndrome, Proceeding National Academy of Science USA, 1985, June, 82 (12), p. 4245-4249; Gouras G K, and 11 others, Intraneuronal Aβ42 accumulation in human brain, American journal of pathology, 2000, January, 156 (1), p. 15-20; Scheuner D, and 20 others, Secreted amyloid β-protein similar to that in the senile plaques of Alzheimer's disease is increased in vivo by the presenilin 1 and 2 and APP mutations linked to familial Alzheimer's disease, Nature Medicine, 1996, August, 2 (8), p. 864-870; Forman M S, and 4 others, Differential effects of the Swedish mutant amyloid precursor protein on β-amyloid accumulation and secretion in neurons and normeuronal cells, The journal of biological chemistry, 1997, Dec. 19, 272 (51), p. 32247-32253), senile dementia (for example, refer to, Blass J P, Brain metabolism and brain disease: Is metabolic deficiency the proximate cause of Alzheimer dementia? Journal of Neuroscience Research, 2001, Dec. 1, 66 (5), p. 851-856), frontotemporal dementia (for example, refer to, Evin G, and 11 others, Alternative transcripts of presenilin-1 associated with frontotemporal dementia, Neuroreport, 2002, Apr. 16, 13 (5), p. 719-723), Pick disease (for example, refer to, Yasuhara O, and 3 others, Accumulation of amyloid precursor protein in brain lesions of patients with Pick disease, Neuroscience Letters, 1994, Apr. 25, 171 (1-2), p. 63-66), Down's syndrome (for example, refer to, Teller J K, and 10 others, Presence of soluble amyloid β-peptide precedes amyloid plaque formation in Down's syndrome, Nature Medicine, 1996, January, 2 (1), p. 93-95; Tokuda T, and 6 others, Plasma levels of amyloid β proteins Aβ1-40 and Aβ1-42 (43) are elevated in Down's syndrome, Annals of Neurology, 1997, February, 41 (2), p. 271-273), cerebrovascular angiopathy (for example, refer to, Hayashi Y, and 9 others, Evidence for presenilin-1 involvement in amyloid angiopathy in the Alzheimer's disease-affected brain, Brain Research, 1998, Apr. 13, 789 (2), p. 307-314; Barelli H, and 15 others, Characterization of new polyclonal antibodies specific for 40 and 42 amino acid-long amyloid β peptides: their use to examine the cell biology of presenilins and the immunohistochemistry of sporadic Alzheimer's disease and cerebral amyloid angiopathy cases, Molecular Medicine, 1997, October, 3 (10), p. 695-707; Calhoun M E, and 10 others, Neuronal overexpression of mutant amyloid precursor protein results in prominent deposition of cerebrovascular amyloid, Proceeding National Academy of Science USA, 1999, Nov. 23, 96 (24), p. 14088-14093; Dermaut B, and 10 others, Cerebral amyloid angiopathy is a pathogenic lesion in Alzheimer's Disease due to a novel presenilin-1 mutation, Brain, 2001, December, 124 (12), p. 2383-2392), hereditary cerebral hemorrhage with amyloidosis (Dutch type) (for example, refer to, Cras P, and 9 others, Presenile Alzheimer dementia characterized by amyloid angiopathy and large amyloid core type senile plaques in the APP 692Ala—>Gly mutation, Acta Neuropathologica (Berl), 1998, September, 96 (3), p. 253-260; Herzig M C, and 14 others, Aβ is targeted to the vasculature in a mouse model of hereditary cerebral hemorrhage with amyloidosis, Nature Neuroscience, 2004, September, 7 (9), p. 954-960; van Duinen S G, and 5 others, Hereditary cerebral hemorrhage with amyloidosis in patients of Dutch origin is related to Alzheimer's disease, Proceeding National Academy of Science USA, 1987, August, 84 (16), p. 5991-5994; Levy E, and 8 others, Mutation of the Alzheimer's disease amyloid gene in hereditary cerebral hemorrhage, Dutch type, Science, 1990, Jun. 1, 248 (4959), p. 1124-1126), cognitive impairment (for example, refer to, Laws S M, and 7 others, Association between the presenilin-1 mutation Glu318Gly and complaints of memory impairment, Neurobiology of Aging, 2002, January-February, 23 (1), p. 55-58), memory disturbance/learning disturbance (for example, refer to, Vaucher E, and 5 others, Object recognition memory and cholinergic parameters in mice expressing human presenilin 1 transgenes, Experimental Neurology, 2002 June, 175 (2), p. 398-406; Morgan D, and 14 others, Aβ peptide vaccination prevents memory loss in an animal model of Alzheimer's disease, Nature, 2000 Dec. 21-28, 408 (6815), p. 982-985; Moran P M, and 3 others, Age-related learning deficits in transgenic mice expressing the 751-amino acid isoform of human β-amyloid precursor protein, Proceeding National Academy of Science USA, 1995, Jun. 6, 92 (12), p. 5341-5345), amyloidosis, cerebral ischemia (for example, refer to, Laws S M, and 7 others, Association between the presenilin-1 mutation Glu318Gly and complaints of memory impairment, Neurobiology of Aging, 2002, January-February, 23 (1), p. 55-58; Koistinaho M, and 10 others, β-amyloid precursor protein transgenic mice that harbor diffuse Aβ deposits but do not form plaques show increased ischemic vulnerability: Role of inflammation, Proceeding National Academy of Science USA, 2002, Feb. 5, 99 (3), p. 1610-1615; Zhang F, and 4 others, Increased susceptibility to ischemic brain damage in transgenic mice overexpressing the amyloid precursor protein, The journal of neuroscience, 1997, Oct. 15, 17 (20), p. 7655-7661), cerebrovascular dementia (for example, refer to, Sadowski M, and 6 others, Links between the pathology of Alzheimer's disease and vascular dementia, Neurochemical Research, 2004, June, 29 (6), p. 1257-1266), opthalmoplegia (for example, refer to, O'Riordan S, and 7 others, Presenilin-1 mutation (E280G), spastic paraparesis, and cranial MRI white-matter abnormalities, Neurology, 2002, Oct. 8, 59 (7), p. 1108-1110), multiple secrosis (for example, refer to, Gehrmann J, and 4 others, Amyloid precursor protein (APP) expression in multiple sclerosis lesions, Glia, 1995, October, 15 (2), p. 141-51; Reynolds W F, and 6 others, Myeloperoxidase polymorphism is associated with gender specific risk for Alzheimer's disease, Experimental Neurology, 1999, January, 155 (1), p. 31-41), head injury, skull damage (for example, refer to, Smith D H, and 4 others, Protein accumulation in traumatic brain injury, NeuroMolecular Medicine, 2003, 4 (1-2), p. 59-72), apraxia (for example, refer to, Matsubara-Tsutsui M, and 7 others, Molecular evidence of presenilin 1 mutation in familial early onset dementia, American journal of Medical Genetics, 2002, Apr. 8, 114 (3), p. 292-298), prion disease, familial amyloid neuropathy, triplet repeat disease (for example, refer to, Kirkitadze M D, and 2 others, Paradigm shifts in Alzheimer's disease and other neurodegenerative disorders: the emerging role of oligomeric assemblies, Journal of Neuroscience Research, 2002, Sep. 1, 69 (5), p. 567-577; Evert B O, and 8 others, Inflammatory genes are upreglulated in expanded ataxin-3-expressing cell lines and spinocerebellar ataxia type 3 brains, The Journal of Neuroscience, 2001, Aug. 1, 21 (15), p. 5389-5396; Mann D M, and another, Deposition of amyloid (A4) protein within the brains of persons with dementing disorders other than Alzheimer's disease and Down's syndrome, Neuroscience Letters, 1990, Feb. 5, 109 (1-2), p. 68-75), Parkinson's disease (for example, refer to, Primavera J, and 4 others, Brain accumulation of amyloid-β in Non-Alzheimer Neurodegeneration, Journal of Alzheimer's Disease, 1999, October, 1 (3), p. 183-193), Dementia with Lewy bodies (for example, refer to, Giasson B I, and 2 others, Interactions of amyloidogenic proteins. NeuroMolecular Medicine, 2003, 4 (1-2), p. 49-58; Masliah E, and 6 others, β-amyloid peptides enhance α-synuclein accumulation and neuronal deficits in a transgenic mouse model linking Alzheimer's disease and Parkinson's disease, Proceeding National Academy of Science USA, 2001, Oct. 9, 98 (21), p. 12245-12250; Barrachina M, and 6 others, Amyloid-β deposition in the cerebral cortex in Dementia with Lewy bodies is accompanied by a relative increase in AβPP mRNA isoforms containing the Kunitz protease inhibitor, Neurochemistry International, 2005, February, 46 (3), p. 253-260; Primavera J, and 4 others, Brain accumulation of amyloid-β in Non-Alzheimer Neurodegeneration, Journal of Alzheimer's Disease, 1999, October, 1 (3), p. 183-193), Parkinsonism-dementia complex (for example, refer to, Schmidt M L, and 6 others, Amyloid plaques in Guam amyotrophic lateral sclerosis/parkinsonism-dementia complex contain species of Aβ similar to those found in the amyloid plaques of Alzheimer's disease and pathological aging, Acta Neuropathologica (Berl), 1998, February, 95 (2), p. 117-122; Ito H, and 3 others, Demonstration of β amyloid protein-containing neurofibrillary tangles in parkinsonism-dementia complex on Guam, Neuropathology and applied neurobiology, 1991, October, 17 (5), p. 365-373), frontotemporal dementia and Parkinsonism linked to chromosome 17 (for example, refer to, Rosso S M, and 3 others, Coexistent tau and amyloid pathology in hereditary frontotemporal dementia with tau mutations, Annals of the New York academy of sciences, 2000, 920, p. 115-119), Dementia with argyrophilic grains (for example, refer to, Tolnay M, and 4 others, Low amyloid (Aβ) plaque load and relative predominance of diffuse plaques distinguish argyrophilic grain disease from Alzheimer's disease, Neuropathology and applied neurobiology, 1999, August, 25 (4), p. 295-305), Niemann-Pick disease (for example, refer to, Jin L W, and 3 others, Intracellular accumulation of amyloidogenic fragments of amyloid-β precursor protein in neurons with Niemann-Pick type C defects is associated with endosomal abnormalities, American Journal of Pathology, 2004, March, 164 (3), p. 975-985), amyotrophic lateral sclerosis (for example, refer to, Sasaki S, and another, Immunoreactivity of β-amyloid precursor protein in amyotrophic lateral sclerosis, Acta Neuropathologica (Berl), 1999, May, 97 (5), p. 463-468; Tamaoka A, and 4 others, Increased amyloid β protein in the skin of patients with amyotrophic lateral sclerosis, Journal of neurology, 2000, August, 247 (8), p. 633-635; Hamilton R L, and another, Alzheimer disease pathology in amyotrophic lateral sclerosis, Acta Neuropathologica, 2004, June, 107 (6), p. 515-522; Turner B J, and 6 others, Brain β-amyloidaccumulation in transgenic mice expressing mutant superoxide dismutase 1, Neurochemical Research, 2004, December, 29 (12), p. 2281-2286), hydrocephalus (for example, refer to, Weller R O, Pathology of cerebrospinal fluid and interstitial fluid of the CNS: Significance for Alzheimer's disease, prion disorders and multiple sclerosis, Journal of Neuropathology and Experimental Neurology, 1998, October, 57 (10), p. 885-894; Silverberg G D, and 4 others, Alzheimer's disease, normal-pressure hydrocephalus, and senescent changes in CSF circulatory physiology: a hypothesis, Lancet neurology, 2003, August, 2 (8), p. 506-511; Weller R O, and 3 others, Cerebral amyloid angiopathy: Accumulation of Aβ in interstitial fluid drainage pathways in Alzheimer's disease, Annals of the New York academy of sciences, 2000, April, 903, p. 110-117; Yow H Y, and another, A role for cerebrovascular disease in determining the pattern of β-amyloid deposition in Alzheimer's disease, Neurology and applied neurobiology, 2002, 28, p. 149; Weller R O, and 4 others, Cerebrovascular disease is a major factor in the failure of elimination of Aβ from the aging human brain, Annals of the New York academy of sciences, 2002, November, 977, p. 162-168), paraparesis (for example, refer to, O'Riordan S, and 7 others, Presenilin-1 mutation (E280G), spastic paraparesis, and cranial MRI white-matter abnormalities, Neurology, 2002, Oct. 8, 59 (7), p. 1108-1110; Matsubara-Tsutsui M, and 7 others, Molecular evidence of presenilin 1 mutation in familial early onset dementia, American journal of Medical Genetics, 2002, Apr. 8, 114 (3), p. 292-298; Smith M J, and 11 others, Variable phenotype of Alzheimer's disease with spastic paraparesis, Annals of Neurology, 2001, 49 (1), p. 125-129; Crook R, and 17 others, A variant of Alzheimer's disease with spastic pararesis and unusual plaques due to deletion of exon 9 of presenilin 1, Nature Medicine, 1998, April; 4 (4), p. 452-455), progressive supranuclear palsy (for example, refer to, Barrachina M, and 6 others, Amyloid-β deposition in the cerebral cortex in Dementia with Lewy bodies is accompanied by a relative increase in AβPP mRNA isoforms containing the Kunitz protease inhibitor, Neurochemistry International, 2005, February, 46 (3), p. 253-260; Primavera J, and 4 others, Brain accumulation of amyloid-β in Non-Alzheimer Neurodegeneration, Journal of Alzheimer's Disease, 1999, October, 1 (3), p. 183-193), cerebral hemorrhage (for example, refer to, Atwood C S, and 3 others, Cerebrovascular requirement for sealant, anti-coagulant and remodeling molecules that allow for the maintenance of vascular integrity and blood supply, Brain Research Reviews, 2003, September, 43 (1), p. 164-78; Lowenson J D, and 2 others, Protein aging: Extracellular amyloid formation and intracellular repair, Trends in cardiovascular medicine, 1994, 4 (1), p. 3-8), spasm (for example, refer to, Singleton A B, and 13 others, Pathology of early-onset Alzheimer's disease cases bearing the Thr113-114ins presenilin-1 mutation, Brain, 2000, December, 123 (Pt12), p. 2467-2474), mild cognitive impairment (for example, refer to, Gattaz W F, and 4 others, Platelet phospholipase A2 activity in Alzheimer's disease and mild cognitive impairment, Journal of Neural Transmission, 2004, May, 111 (5), p. 591-601; Assini A, and 14 others, Plasma levels of amyloid β-protein 42 are increased in women with mild cognitive impairment, Neurology, 2004, Sep. 14, 63 (5), p. 828-831), arteriosclerosis (for example, refer to, De Meyer G R, and 8 others, Platelet phagocytosis and processing of β-amyloid precursor protein as a mechanism of macrophage activation in atherosclerosis, Circulation Research, 2002, Jun. 14, 90 (11), p. 1197-1204)

The term "C1-3 alkyl group" refers to an alkyl group having 1 to 3 carbon atoms, and preferred examples thereof include linear or branched alkyl groups such as a methyl group, an ethyl group, an n-propyl group, and an i-propyl group.

The term "C3-6 cycloalkyl group" refers to a cyclic alkyl group having 3 to 6 carbon atoms, and preferred examples thereof include a cyclopropyl group, a cyclobutyl group, a cyclopentyl group, and a cyclohexyl group.

The term "C1-6 alkyl group" refers to an alkyl group having 1 to 6 carbon atoms, and preferred examples thereof include linear or branched alkyl groups such as a methyl group, an ethyl group, an n-propyl group, an i-propyl group, an n-butyl group, an i-butyl group, a tertiary butyl group, an n-pentyl group, an i-pentyl group, a neopentyl group, an n-hexyl group, a 1-methylpropyl group, a 1,2-dimethylpropyl group, a 1-ethylpropyl group, a 1-methyl-2-ethylpropyl group, a 1-ethyl-2-methylpropyl group, a 1,1,2-trimethylpropyl group, a 1-methylbutyl group, a 2-methylbutyl group, a 1,1-dimethylbutyl group, a 2,2-dimethylbutyl group, a 2-ethylbutyl group, a 1,3-dimethylbutyl group, a 2-methylpentyl group, and a 3-methylpentyl group.

The term "C1-6 acyl group" used herein refers to an acyl group having 1 to 6 carbon atoms, and preferred examples thereof include a formyl group, an acetyl group, a propionyl group, a butyryl group, an isobutyryl group, a pentanoyl group, and a hexanoyl group.

The expression "$R^1$ and $R^2$ form, together with the carbon atom to which they are attached, a C3-6 cycloalkyl group" is specifically shown by the following formula, for example:

[Formula 2]

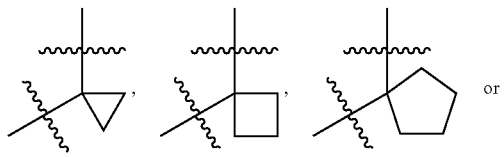

or

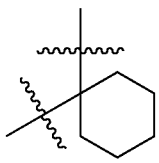

The substituent group A1 refers to the following groups.
Substituent group A1: (1) a halogen atom, (2) a hydroxyl group, (3) a cyano group, (4) a C3-8 cycloalkyl group, (5) a C3-8 cycloalkoxy group, (6) a C1-6 alkyl group (the C1-6 alkyl group may be substituted with 1 to 5 halogen atoms or 1 to 3 C1-6 alkoxy groups), (7) an amino group which may be substituted with 1 or 2 C1-6 alkyl groups (the C1-6 alkyl group may be substituted with 1 to 5 halogen atoms), (8) a C1-6 alkoxy group (the C1-6 alkoxy group may be substituted with 1 to 5 halogen atoms), and (9) a carbamoyl group which may be substituted with 1 or 2 C1-6 alkyl groups (the C1-6 alkyl group may be substituted with 1 to 3 halogen atoms).

Here, the term "halogen atom" refers to a fluorine atom, a chlorine atom, a bromine atom, an iodine atom, or the like and is preferably a fluorine atom, a chlorine atom, or a bromine atom.

The term "C3-8 cycloalkyl group" refers to a cyclic alkyl group having 3 to 8 carbon atoms, and preferred examples thereof include a cyclopropyl group, a cyclobutyl group, a cyclopentyl group, a cyclohexyl group, a cycloheptyl group, and a cyclooctyl group.

The term "C3-8 cycloalkoxy group" refers to a cyclic alkyl group having 3 to 8 carbon atoms in which one hydrogen atom is replaced with an oxygen atom, and preferred examples thereof include a cyclopropoxy group, a cyclobutoxy group, a cyclopentoxy group, a cyclohexoxy group, a cycloheptyloxy group, and a cyclooctyloxy group.

The term "C1-6 alkyl group" refers to an alkyl group having 1 to 6 carbon atoms, and preferred examples thereof include linear or branched alkyl groups such as a methyl group, an ethyl group, an n-propyl group, an i-propyl group, an n-butyl group, an i-butyl group, a tertiary butyl group, an n-pentyl group, an i-pentyl group, a neopentyl group, an n-hexyl group, a 1-methylpropyl group, a 1,2-dimethylpropyl group, a 1-ethylpropyl group, a 1-methyl-2-ethylpropyl group, a 1-ethyl-2-methylpropyl group, a 1,1,2-trimethylpropyl group, a 1-methylbutyl group, a 2-methylbutyl group, a 1,1-dimethylbutyl group, a 2,2-dimethylbutyl group, a 2-ethylbutyl group, a 1,3-dimethylbutyl group, a 2-methylpentyl group, and a 3-methylpentyl group.

The term "C1-6 alkoxy group" refers to an alkyl group having 1 to 6 carbon atoms in which a hydrogen atom is replaced with an oxygen atom, and preferred examples thereof include a methoxy group, an ethoxy group, an n-propoxy group, an i-propoxy group, an n-butoxy group, an i-butoxy group, a sec-butoxy group, a tertiary butoxy group, an n-pentoxy group, an i-pentoxy group, a sec-pentoxy group, a tertiary pentoxy group, an n-hexoxy group, an i-hexoxy group, a 1,2-dimethylpropoxy group, a 2-ethylpropoxy group, a 1-methyl-2-ethylpropoxy group, a 1-ethyl-2-methylpropoxy group, a 1,1,2-trimethylpropoxy group, a 1,1,2-trimethylpropoxy group, a 1,1-dimethylbutoxy group, a 2,2-dimethylbutoxy group, a 2-ethylbutoxy group, a 1,3-dimethylbutoxy group, a 2-methylpentoxy group, a 3-methylpentoxy group, and a hexyloxy group.

The term "amino group which may be substituted with 1 or 2 C1-6 alkyl groups" refers to an amino group in which a hydrogen atom(s) is replaced with 1 or 2 alkyl groups having 1 to 6 carbon atoms, and preferred examples thereof include a methylamino group, a dimethylamino group, an ethylamino group, a diethylamino group, an n-propylamino group, and a di-n-propylamino group.

The term "carbamoyl group which may be substituted with 1 or 2 C1-6 alkyl groups" refers to a carbamoyl group in which a hydrogen atom(s) is replaced with 1 or 2 alkyl groups having 1 to 6 carbon atoms, and preferred examples thereof include a methylcarbamoyl group, a dimethylcarbamoyl group, an ethylcarbamoyl group, a diethylcarbamoyl group, an n-propylcarbamoyl group, and a di-n-propylcarbamoyl group.

In the present specification, "pharmacologically acceptable salts" are not particularly limited so long as they are formed as a pharmacologically acceptable salt of the compound represented by the general formula (I) to be used as an agent for prophylactic or therapeutic treatment of diseases attributable to Aβ. Specific preferred examples thereof include hydrohalides (for example, hydrofluorides, hydrochlorides, hydrobromides, and hydroiodides), inorganic acid salts (for example, sulfates, nitrates, perchlorates, phosphates, carbonates, and bicarbonates), organic carboxylates (for example, acetates, oxalates, maleates, tartarates, fumarates, and citrates), organic sulfonates (for example, methanesulfonates, trifluoromethanesulfonates, ethanesulfonates, benzenesulfonates, toluenesulfonates, and camphor sulfonates), amino acid salts (for example, aspartates, and glutamates), quaternary amine salts, alkali metal salts (for example, sodium salts and potassium salts), and alkaline earth metal salts (for example, magnesium salts and calcium salts).

The compound represented by the formula (I) of the present invention will be explained below.

The compound represented by the formula (I) is preferably a compound in which (1) $R^1$ represents a C1-3 alkyl group, $R^2$ represents a hydrogen atom or a C1-3 alkyl group, or (2) $R^1$ and $R^2$ form, together with the carbon atom to which they are attached, a C3-6 cycloalkyl group, or a pharmacologically acceptable salt thereof; and the compound represented by the formula (I) is more preferably is a compound in which (1) $R^1$ represents a methyl group, $R^2$ represents a hydrogen atom or a methyl group, or (2) $R^1$ and $R^2$, together with the carbon atoms to which they are attached form a cyclopropyl group, or a pharmacologically acceptable salt thereof.

The compound represented by the formula (I) is preferably a compound in which Ar represents a phenyl group or a pyridinyl group which may be substituted with 1 to 3 substituents that are the same or different and selected from the substituent group A1, or a pharmacologically acceptable salt thereof; and the compound represented by the formula (I) is more preferably a compound in which Ar represents a phenyl group which may be substituted with 1 to 3 halogen atoms, or a pharmacologically acceptable salt thereof.

The compound represented by the formula (I) is preferably a compound in which X represents a methylene group or a vinylene group which may be substituted with 1 or 2 substituents selected from the substituent group A1, an oxygen atom, or an imino group which may be substituted with a C1-6 alkyl group or a C1-6 acyl group, and n and m are the same or different and integers of 0 to 2, or a pharmacologically acceptable salt thereof; and the compound represented by the formula (I) is more preferably (1) a compound in which X represents a methylene group (the methylene group may be substituted with 1 or 2 substituents that are the same or different and selected from the group consisting of C1-6 alkyl groups and hydroxyl group), and n and m are 1, or a pharmacologically acceptable salt thereof, (2) a compound in which X represents an oxygen atom, and n and m are 1, or a pharmacologically acceptable salt thereof, or (3) a compound in which X represents a methylene group, n is 1, and m is 0, or a pharmacologically acceptable salt thereof.

For example, a compound selected from the following group or a pharmacologically acceptable salt is particularly preferred and useful as an agent for therapeutic or prophylactic treatment of diseases attributable to amyloid beta such as, for example, Alzheimer's disease, senile dementia, Down's syndrome, and amyloidosis.

1) (Z)-(1R,6R,9aR)-3-[3-Methoxy-4-(4-methylimidazol-1-yl)benzylidene]-1-methyl-6-(3,4,5-trifluorophenyl)tetrahydro-[1,4]oxazino[3,4-c][1,4]oxazin-4-one,
2) (Z)-(1S,6R,9aR)-3-[3-Methoxy-4-(4-methylimidazol-1-yl)benzylidene]-1-methyl-6-(3,4,5-trifluorophenyl)tetrahydro-[1,4]oxazino[3,4-c][1,4]oxazin-4-one,
3) (Z)-(1S,6R,9aR)-6-(3,4-Difluoro-phenyl)-3-[3-methoxy-4-(4-methylimidazol-1-yl)benzylidene]-1-methyltetrahydro-[1,4]oxazino[3,4-c][1,4]oxazin-4-one,
4) (Z)-(6S,8aR)-6-(4-Fluorophenyl)-3-[3-methoxy-4-(4-methylimidazol-1-yl)benzylidene]-1,1-dimethyltetrahydropyrrolo[2,1-c][1,4]oxazin-4-one,
5) (Z)-(1S,6R,9aR)-3-[3-Methoxy-4-(4-methylimidazol-1-yl)benzylidene]-1-methyl-6-(4-chlorophenyl)hexahydropyrido[2,1-c][1,4]oxazin-4-one,
6) (Z)-(1S,6S,8aR)-6-(4-Fluorophenyl)-3-[3-methoxy-4-(4-methylimidazol-1-yl)benzylidene]-1-methyltetrahydropyrrolo[2,1-c][1,4]oxazin-4-one,
7) (Z)-(1R,6S,8aR)-6-(4-Fluorophenyl)-3-[3-methoxy-4-(4-methylimidazol-1-yl)benzylidene]-1-methyltetrahydropyrrolo[2,1-c][1,4]oxazin-4-one,
8) (Z)-(6S,8aR)-6-(4-Chlorophenyl)-3-[3-methyloxy-4-(4-methylimidazol-1-yl)benzylidene]-1,1-dimethyltetrahydropyrrolo[2,1-c][1,4]oxazin-4-one,
9) (Z)-(1S,6S,8aR)-6-(4-Chlorophenyl)-3-[3-methoxy-4-(4-methylimidazol-1-yl)benzylidene]-1-methyltetrahydropyrrolo[2,1-c][1,4]oxazin-4-one,
10) (Z)-(1R,6S,8aR)-6-(4-Chlorophenyl)-3-[3-methoxy-4-(4-methylimidazol-1-yl)benzylidene]-1-methyltetrahydropyrrolo[2,1-c][1,4]oxazin-4-one,
11) (Z)-(6S,8aR)-3-[3-Methoxy-4-(4-methylimidazol-1-yl)benzylidene]-1,1-dimethyl-6-(3,4,5-trifluorophenyl)tetrahydropyrrolo[2,1-c][1,4]oxazin-4-one,
12) (Z)-(1S,6S,8aR)-3-[3-Methoxy-4-(4-methylimidazol-1-yl)benzylidene]-1-methyl-6-(3,4,5-trifluorophenyl)tetrahydropyrrolo[2,1-c][1,4]oxazin-4-one,
13) (Z)-(1R,6S,8aR)-3-[3-Methoxy-4-(4-methylimidazol-1-yl)benzylidene]-1-methyl-6-(3,4,5-trifluorophenyl)tetrahydropyrrolo[2,1-c][1,4]oxazin-4-one,
14) (Z)-(6S,8aR)-6-(3,4-Difluoro-phenyl)-3-[3-methoxy-4-(4-methylimidazol-1-yl)benzylidene]-1,1-dimethyltetrahydropyrrolo[2,1-c][1,4]oxazin-4-one,
15) (Z)-(1S,6S,8aR)-6-(3,4-Difluoro-phenyl)-3-[3-methoxy-4-(4-methylimidazol-1-yl)benzylidene]-1-methyltetrahydropyrrolo[2,1-c][1,4]oxazin-4-one,
16) (Z)-(1R,6S,9aR)-3-[3-Methoxy-4-(4-methylimidazol-1-yl)benzylidene]-1-methyl-6-(3,4,5-trifluorophenyl) hexahydropyrido[2,1-c][1,4]oxazin-4-one,
17) (Z)-(1S,6S,9aR)-3-[3-Methoxy-4-(4-methylimidazol-1-yl)benzylidene]-1-methyl-6-(3,4,5-trifluorophenyl) hexahydropyrido[2,1-c][1,4]oxazin-4-one, 18) (Z)-(6S,8aR)-3-[3-Methoxy-4-(4-methylimidazol-1-yl)benzylidene]-1,1-cyclopropyl-6-(3,4,5-trifluorophenyl)tetrahydropyrrolo[2,1-c][1,4]oxazin-4-one, and
19) (6R,9aR)-3-[1-[3-methoxy-4-(4-methyl-1H-imidazol-1-yl)phenyl-(Z)-methylidene]-1,1-dimethyl-6-(3,4,5-trifluorophenyl)tetrahydro [1,4[oxazino[3,4-c][1,4]oxazin-4-one.

The above are preferred embodiments of the compound represented by the above-mentioned general formula (I). However, active ingredients of the medicament according to the present invention are not limited to specific compounds described in the present specification, but any embodiment encompassed within the scope of the compound represented by the general formula (I) can be selected to a maximum extent.

Hereafter, the method for producing the compound represented by the general formula (I) of the present invention will be explained.

The compound represented by the general formula (I):

[Formula 3]

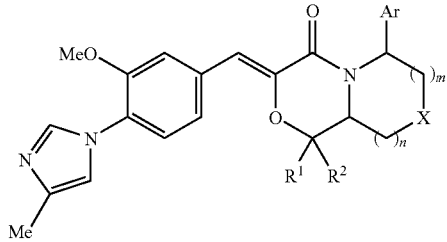

wherein $R^1$, $R^2$, X, and Ar have the same meanings as defined above is synthesized according to methods such as, for example, the general production method 1 or 2 described below. To produce the compound of the present invention conveniently, it will be obvious to select a preferred protection group known to those skilled in the art (for example, refer to Greene T, and others, "Protective Groups in Organic Synthesis," John Wiley & Sons. Inc., New York, 1981) at each step and suitably include a protection reaction step and a deprotection reaction step. Furthermore, to produce the compound of the present invention conveniently, it should be recognized that all isomers such as geometrical isomers, optical isomers based on asymmetric carbons, stereoisomers, and tautomers that exist based on the structure of the compound, and isomer mixtures can be produced as a single compound by techniques known to those skilled in the art such as preferable fractional recrystallization and column chromatography at each step.

General Production Method 1

A representative general production method 1 of the compound represented by the general formula (I) according to the present invention will be explained below.

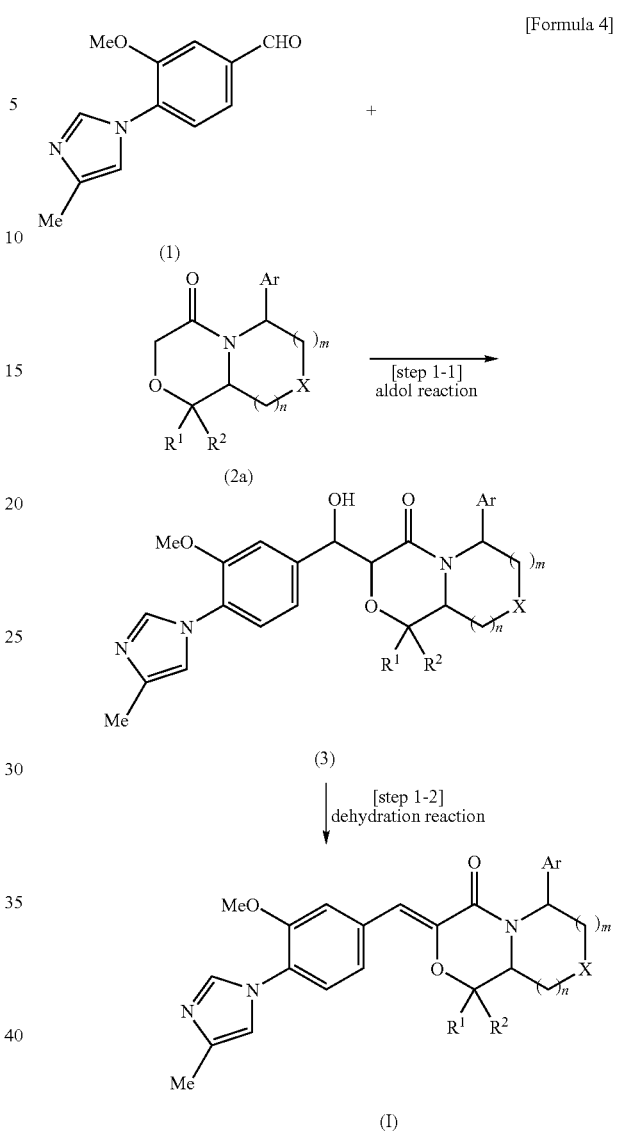

wherein $R^1$, $R^2$, X, m, n, and Ar have the same meanings as defined above.

The general production method 1 shown above is one example of methods for producing the compound represented by the general formula (I) comprising subjecting an aldehyde compound (1) and a lactam compound (2) to an aldol reaction at step 1-1 to convert them to an aldol adduct (3) and then subjecting it to a dehydration reaction.

Preparation of Compound Represented by the General Formula (I)

The compound represented by the general formula (I) can be prepared by subjecting an aldol adduct (3) to the reaction of step 1-2. That is, the dehydration reaction at step 1-2 varies depending on a starting material and is not particularly limited so long as it is performed under conditions like those of this reaction, and known techniques described in many publications can be used (for example, described in The Chemical Society of Japan, Ed., "Experimental Chemistry Lecture, Vol. 19, Organic Synthesis [I]," Maruzen Co., Ltd., June 1992, p. 194-226). Preferred examples thereof include i) a method comprising treating an aldol adduct (3) preferably with, for example, 0.1 to 100.0 equivalents of an acid (for example, described in The Chemical Society of Japan, Ed., "Experimental Chemistry Lecture, Vol. 19, Organic Synthesis [I]," Maruzen Co., Ltd., June 1992, p. 194-196) and ii) a method comprising converting an alcohol group of an aldol adduct (3) to a leaving group such as a carboxylic acid ester group such as acetyl group, sulfonic acid ester group, or an halogen atom and then treating the aldol adduct (3) preferably with, for example, 1.0 to 10.0 equivalents of a base (for example, described in The Chemical Society of Japan, Ed., "Experimental Chemistry Lecture, Vol. 19, Organic Synthesis [I]," Maruzen Co., Ltd., June 1992, p. 198-205).

In the method of i), the acid used, solvent and temperature condition vary depending on a starting material and are not particularly limited, but preferred examples thereof include hydrochloric acid, sulfuric acid, phosphoric acid, potassium hydrogensulfide, oxalic acid, paratoluenesulfonic acid, trifluoride boric acid ether complex, thionyl chloride, and alumina oxide. The reaction may be performed without using a solvent, but solvents that do not inhibit a reaction and dissolve the starting material to some extent or a mixture thereof are used. Preferred examples thereof include nonpolar solvents such as toluene and benzene, polar solvents such as acetone, dimethyl sulfoxide, and hexamethyl phosphoroamide, halogen solvents such as chloroform and methylene chloride, and water. Furthermore, in some cases, preferably, a combination of, for example, an acid and an organic base such as pyridine may improve the reaction rate and the reaction yield. The reaction temperature should be a temperature which is sufficient to complete a reaction without promoting formation of undesirable byproducts, and is preferably from room temperature to 200° C., for example. Under preferable reaction conditions, this reaction is preferably completed in, for example, 1 to 24 hours, and the progress of a reaction can be monitored by known chromatography techniques. Undesirable byproducts can be removed by techniques known to those skilled in the art such as commonly used chromatography techniques, extraction operation, or/and crystallization.

In the method of ii), preferred examples of the leaving group include acetyl group, methanesulfonic acid ester group, paratoluenesulfonic acid ester group, chlorine atom, bromine atom, and iodine atom. Techniques of converting to these leaving groups vary depending on a starting material and are not particularly limited, and methods known to those skilled in the art can be used. For example, halogen solvents such as methylene chloride and chloroform, nonpolar solvents such as toluene and benzene, ether solvents such as tetrahydrofuran and ethylene glycol dimethyl ether, or mixed solvents can be used. Preferred examples thereof include 1.0 to 10.0 equivalents of acetylating agents such as acetyl chloride and acetic anhydride, sulfonic acid esterifying agents such as methanesulfonic acid chloride and paratoluenesulfonic acid chloride, or halogenating agents such as thionyl chloride. Furthermore, a target compound may be obtained efficiently, when, for example, 1.0 to 10.0 equivalents of a base such as pyridine or triethylamine is preferably used at this step or used as a reaction solvent. The reaction temperature should be a temperature which is sufficient to complete a reaction without promoting formation of undesirable byproducts, and is preferably from −78 to 100° C., for example. Under preferable reaction conditions, this reaction is preferably completed in, for example, 1 to 24 hours, and the progress of a reaction can be monitored by known chromatography techniques. Undesirable byproducts can be removed by techniques known to those skilled in the art such as commonly used chromatography techniques, extraction operation, or/and crystallization. In the elimination reaction, the second step, for example, halogen solvents such as methylene chloride and chloroform, nonpolar solvents such as toluene and benzene, polar solvents such as acetonitrile, dimethylformamide, and dimethyl sulfoxide, ether solvents such as tetrahydrofuran and ethylene glycol dimethyl ether, or mixed solvents thereof can be preferably used. As bases, it is preferable to use, for example, 1.0 to 10.0 equivalents of organic bases such as diazabicycloundecene, pyridine, 4-dimethylaminopyridine, and triethylamine, quaternary ammonium salts such as tetrabutylammonium hydroxide, alkali metal salts of alcohols such as sodium methoxide and potassium tertiary butoxide, alkali metal hydroxides such as sodium hydroxide, alkali metal carbonates such as lithium carbonate and potassium carbonate, organic metal reagents such as lithium diisopropylamide. Furthermore, organic bases such as pyridine can be used as solvents. The reaction temperature should be a temperature which is sufficient to complete reactions without promoting formation of undesirable byproducts, and is preferably from −78 to 100° C., for example. Under preferable reaction conditions, this reaction is preferably completed in, for example, 1 to 24 hours, and the progress of a reaction can be monitored by known chromatography techniques. Undesirable byproducts can be removed by techniques known to those skilled in the art such as commonly used chromatography techniques, extraction operation, or/and crystallization.

Preparation of Aldol Adduct (3)

The aldol adduct (3) can be prepared, for example, from an aldehyde compound (1) and 1.0 to 5.0 equivalents of a lactam compound (2) based on the aldehyde compound (1) according to step 1-1. That is, the aldol reaction at step 1-1 varies depending on a starting material and is not particularly limited so long as it is performed under conditions like those for this reaction, and techniques known to those skilled in the art can be used (for example, described in The Chemical Society of Japan, Ed., "Experimental Chemistry Lecture, Vol. 20, Organic Synthesis [II]," Maruzen Co., Ltd., July 1992, p. 94-100). Preferred examples include i) a technique in which a lactam compound (2) is converted to an alkali metal enolate preferably using, for example, 1.0 to 5.0 equivalents of a base (preferred examples thereof include lithium diisopropylamide, butyl lithium, sodium amide, sodium hydride, sodium methoxide, and potassium tertiary butoxide) and then reacted with an aldehyde compound (1) (for example, described in The Chemical Society of Japan, Ed., "Experimental Chemistry Lecture, Vol. 20, Organic Synthesis [II]," Maruzen Co., Ltd., July 1992, p. 97-98) and ii) a technique in which a lactam compound (2) is converted to alkali metal enolate preferably using, for example, 1.0 to 5.0 equivalents of a base (preferred examples include lithium diisopropylamide, butyl lithium, sodium amide, sodium hydride, sodium methoxide, and potassium tertiary butoxide), reacted with a halogenated silicon reagent (preferred examples include trimethylchlorosilane and tertiary butyldimethylchlorosilane,) to be once converted to silyl enol ether, and then reacted with an aldehyde compound (1) preferably in the presence of, for example, 0.05 to 5.0 equivalents of Lewis acid (preferred examples include titanium tetrachloride and boron trifluoride) (for example, described in The Chemical Society of Japan, Ed., "Experimental Chemistry Lecture, Vol. 20, Organic Synthesis [II]," Maruzen Co., Ltd., July 1992, p. 96-97). The solvent and the reaction temperature used vary depending on a starting material and are not particularly limited, but solvents that do not inhibit a reaction and dissolve the starting material to some extent, or mixed solvents thereof can be used. Preferred examples thereof include ether solvents such as tetrahydrofuran, 1,4-dioxane, and diethyl ether, halogen solvents such as methylene chloride, 1,2-dichloroethane, and chloroform, and nonpolar solvents such as toluene and benzene. The reaction temperature should be a temperature which is sufficient to complete a reaction without promoting formation of undesirable byproducts, and is preferably from −78° C. to room temperature, for example. Under preferable reaction conditions, this reaction is preferably completed in, for example, 0.5 to 24 hours, and the progress of a reaction can be monitored by known chromatography techniques. Undesirable byproducts can be removed by techniques known to those skilled in the art such as commonly used chromatography techniques, extraction operation, or/and crystallization.

Preparation of Aldehyde Compound (1)

The aldehyde compound (1) can be produced by the known method described in WO2005/115990.

Preparation of Amide Compound (2a)

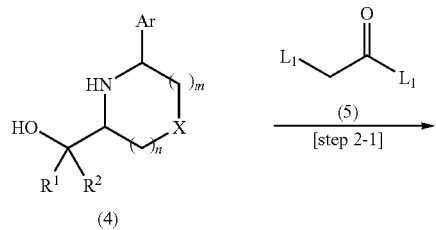 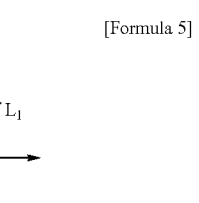

[Formula 5]

wherein $R^1$, $R^2$, X, m, n and Ar have the same meanings as defined above, and $L_1$ represents a fluorine atom, a chlorine atom, a bromine atom, an iodine atom, a sulfonate group such as triflate, a trialkyl tin group, a boronic acid or boronic ester group.

The above reaction formula is one example of a method for producing the amide compound (2a) comprising condensing an amino alcohol compound (4) and a compound (5) according to step 2-1 to construct an oxomorpholine ring.

Preparation of Compound (2a)

The reaction at step 2-1 varies depending on a starting material and is not particularly limited so long as it is performed under conditions like those of this reaction, and methods known to those skilled in the art can be used. The reaction is conveniently progressed preferably by, for example, vigorously stirring a compound (4) and 1.0 to 10 equivalents of a compound (5) based on the compound (4) with a two-phase reaction solvent consisting of an organic solvent and a basic aqueous solution. The solvent and the reaction temperature used vary depending on a starting material and are not particularly limited, but solvents that do not inhibit a reaction and dissolve the starting material to some extent or a mixture thereof can be preferably used. Preferred examples thereof include ether solvents such as diethyl ether, halogenated solvents such as methylene chloride, 1,2-dichloroethane, and chloroform, and nonpolar solvents such as toluene and xylene. Preferred examples of basic aqueous solutions that can be used include aqueous solutions of alkali metal salts such as sodium hydroxide, potassium hydroxide, sodium carbonate, potassium carbonate, cesium carbonate, and sodium hydrogencarbonate. The reaction temperature should be a temperature which is sufficient to complete a reaction without promoting formation of undesirable byproducts, and is preferably from −78° C. to room temperature, for example. Under preferable reaction conditions, this reaction is preferably completed in, for example, 0.5 to 24 hours, and the progress of a reaction can be monitored by known chromatography techniques. Undesirable byproducts can be removed by techniques known to those skilled in the art such as commonly used chromatography techniques, extraction operation, or/and crystallization.

Furthermore, preferably, the reaction may be progressed conveniently by mixing, for example, the compound (4) and 1.0 to 10 equivalents of the compound (5) based on compound (4) under a basic condition. The solvent and the reaction temperature used vary depending on a starting material and are not particularly limited, but solvents that do not inhibit a reaction and dissolve the starting material to some extent or a mixture thereof can be preferably used. Preferred examples thereof include ether solvents such as diethyl ether and tetrahydrofuran, halogenated solvents such as methylene chloride, 1,2-dichloroethane, and chloroform, and nonpolar solvents such as toluene and xylene. The base used varies depending on a starting material and is not particularly limited, but 1.0 to 10 equivalents thereof based on the compound (4) can be preferably used. Examples thereof include alkali metal salts such as sodium hydroxide, potassium hydroxide, sodium carbonate, potassium carbonate, cesium carbonate, and sodium hydrogencarbonate and organic bases such as diazabicycloundecene, pyridine, 4-dimethylaminopyridine, and triethylamine. The reaction temperature should be a temperature which is sufficient to complete a reaction without promoting formation of undesirable byproducts, and is preferably from −78° C. to room temperature, for example. Under preferable reaction conditions, this reaction is preferably completed in, for example, 0.5 to 24 hours, and the progress of a reaction can be monitored by known chromatography techniques. Undesirable byproducts can be removed by techniques known to those skilled in the art such as commonly used chromatography techniques, extraction operation, or/and crystallization.

Preparation of Compound (5)

The compound (5) is commercially available or can be prepared by methods known to those skilled in the art. Preferred examples thereof include chloroacetyl chloride, and bromoacetyl bromide.

Preparation of Compound (4)

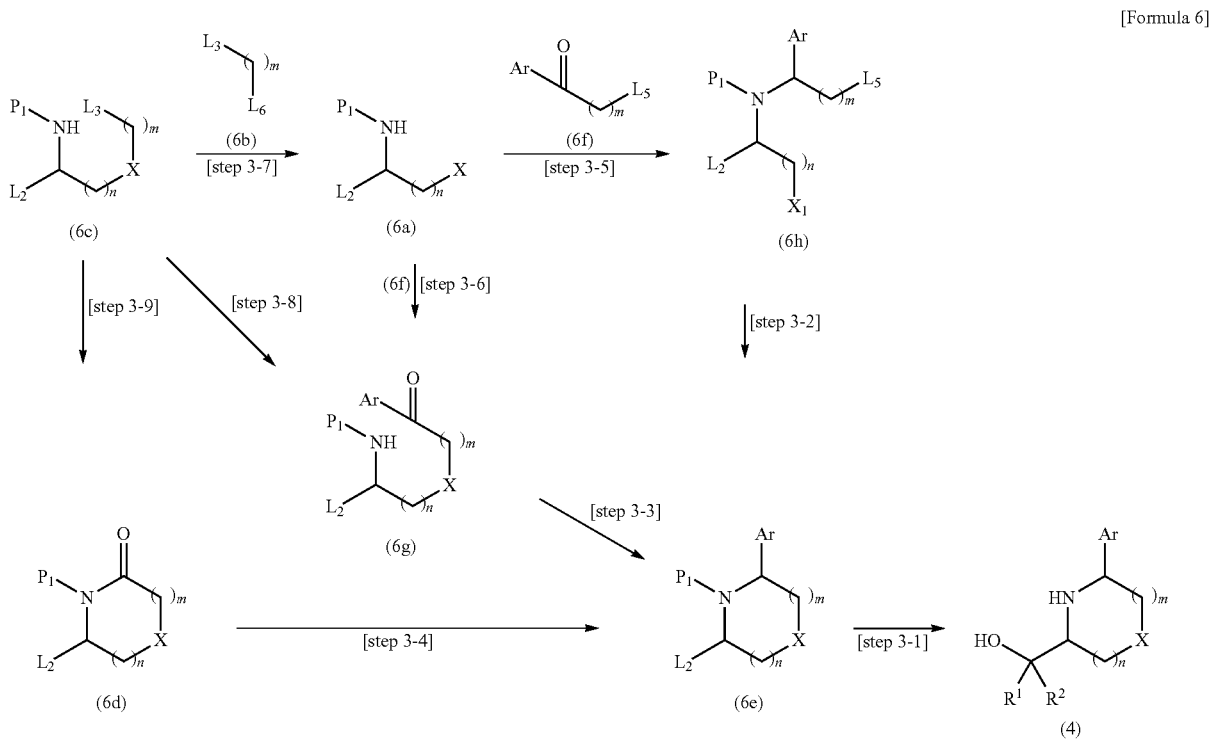

[Formula 6]

wherein $R^1$, $R^2$, X, m, n and Ar have the same meanings as defined above, $L_2$ represents a hydroxyl group that may have a protection group, an ester group such as methyl ester, ethyl ester, tertiary butyl ester, or benzyl ester, an aldehyde group, or a cyano group, $L_3$ represents carboxylic acid, an ester group such as methyl ester, ethyl ester, tertiary butyl ester, or benzyl ester, an aldehyde group, a carbamate group such as a methoxymethylamide group or a pyrrolidineamide group, or a cyano group, $L_4$ represents a fluorine atom, a chlorine atom, a bromine atom, an iodine atom, or a sulfonate group such as triflate, $L_5$ represents a fluorine atom, a chlorine atom, a bromine atom, an iodine atom, or a sulfonate group such as triflate, or a hydroxyl group that may have a protection group, $X_1$ represents an oxygen atom that may have a protection group, a sulfur atom, or a nitrogen atom, $P_1$ represents a carbamate protection group such as methyl carbamate, tertiary butyl carbamate, benzyl carbamate, or 9-fluorenylmethyl carbamate, an alkyl protection group such as benzyl group, an allyl group, or a trityl group, or an acyl protection group such as a formyl group, an acetyl group, or a benzoyl group.

Preparation of Compound (4)

The compound (4) can be prepared by subjecting a compound (6e) to i) a reduction reaction or ii) a reaction with an organic metal reagent according to step 3-1.

The reaction of i), that is, the reduction reaction at step 3-1 varies depending on a starting material and is not particularly limited so long as it is performed under conditions like those of this reaction, and known methods described in many publications can be used (for example, refer to The Chemical Society of Japan, Ed., "Experimental Chemistry Lecture, Vol. 26, Organic Synthesis [VIII]," Maruzen Co., Ltd., April 1992, p. 159-266). Preferred examples include a method comprising stirring the compound (6e) in a solvent in the presence of 1.0 to 10.0 equivalents of a reducing reagent based on the compound (6e). The reducing reagent used varies depending on a starting material and is not particularly limited, but preferred examples thereof include lithium borohydride, sodium borohydride, aluminium hydride, diisobutylaluminium hydride, and diborane. The solvent used varies depending on a starting material and is not particularly limited, but solvents that do not inhibit a reaction and dissolve the starting material to some extent or a mixture thereof can be preferably used. Preferred examples thereof include ether solvents such as diethyl ether, tetrahydrofuran, dimethoxyethane, and 1,4-dioxane and nonpolar solvents such as toluene and xylene. The reaction temperature should be a temperature which is sufficient to complete a reaction without promoting formation of undesirable byproducts, and is preferably from −78° C. to room temperature, for example. Under preferable reaction conditions, this reaction is preferably completed in, for example, 0.5 to 24 hours, and the progress of a reaction can be monitored by known chromatography techniques. Undesirable byproducts can be removed by techniques known to those skilled in the art such as commonly used chromatography techniques, extraction operation, or/and crystallization.

The reaction of ii), that is, the reaction with an organic metal reagent at step 3-1 varies depending on a starting material and is not particularly limited so long as it is performed under conditions like those of this reaction, and known methods described in many publications can be used (for example, refer to The Chemical Society of Japan, Ed., "Experimental Chemistry Lecture, Vol. 25, Organic Synthesis [VII]," Maruzen Co., Ltd., September 1991, p. 9-82). Preferred examples thereof include a method comprising stirring the compound (6e) in a solvent in the presence of 1.0 to 10.0 equivalents of an organic metal reagent based on the compound (6e). The organic metal reagent used varies depending on a starting material and is not particularly limited, but preferred examples thereof include organic lithium reagents such as methyllithium and ethyllithium, Grignard reagents such as methylmagnesium bromide and ethylmagnesium bromide, and organic zinc reagents such as dimethylzinc. Furthermore, in some cases, the reaction may be progressed conveniently by adding 0.1 to 1.0 equivalents of Lewis acid such as boron trifluoride, titanium tetraisopropoxide, or lithium perchlorate (for example, refer to Russian Journal of Organic Chemistry, 2005, 41, p. 70-74) based on the compound (6e). The solvent used varies depending on a starting material and is not particularly limited, but solvents that do not inhibit a reaction and dissolve the starting material to some extent or a mixture thereof can be preferably used. Preferred examples thereof include ether solvents such as diethyl ether, tetrahydrofuran, dimethoxyethane, and 1,4-dioxane and nonpolar solvents such as toluene and xylene. The reaction temperature should be a temperature which is sufficient to complete reactions without promoting formation of undesirable byproducts, and is preferably from −78° C. to room temperature, for example. Under preferable reaction conditions, this reaction is preferably completed in, for example, 0.5 to 24 hours, and the progress of a reaction can be monitored by known chromatography techniques. Undesirable byproducts can be removed by techniques known to those skilled in the art such as commonly used chromatography techniques, extraction operation, or/and crystallization.

Preparation of Compound (6e)

The compound (6e) can be prepared by subjecting a compound (6h) to a cyclization reaction according to step 3-2. Alternatively, the compound (6e) can be prepared by subjecting a compound (6g) to intramolecular a reducing amination according to step 3-3. Alternatively, the compound (6e) can be prepared by reacting an organic metal reagent with a compound (6d) and subjecting the product to a reduction reaction according to step 3-4.

The cyclization reaction at step 3-2 varies depending on a starting material and is not particularly limited so long as it is performed under conditions like those of this reaction, and methods described in many publications can be used, including i) an intramolecular nucleophilic substitution reaction (for example, refer to The Chemical Society of Japan, Ed., "Experimental Chemistry Lecture, Vol. 20, Organic Synthesis [II]," Maruzen Co., Ltd., July 1992, p. 187-194 and p. 284-288) and ii) a ring formation reaction from diol or aminoalcohol (for example, refer to Journal of Fluorine Chemistry, 1997, 2, p. 119; Scientia Pharmaceutica, 1996, 64, p. 3; Petrochemia, 1990, 30, p. 56, WO2003/076386; and Tetrahedron Letters, 1982, 23, p. 229).

The reaction of i), that is, the intramolecular nucleophilic substitution reaction at step 3-2 varies depending on a starting material and is not particularly limited so long as it is performed under conditions like those of this reaction, and methods known to those skilled in the art can be used. Preferred examples thereof include a method comprising stirring a compound (6h) suitably deprotected by a method known to those skilled in the art (refer to Greene T, and others, "Protective Groups in Organic Synthesis," John Wiley & Sons. Inc., New York, 1981) (here, $L_5$ represents a fluorine atom, a chlorine atom, a bromine atom, an iodine atom, or a sulfonate group such as triflate, and $X_1$ represents an oxygen atom, a sulfur atom, or a nitrogen atom) in a solvent in the presence of 1.0 to 10 equivalents of a base based on the compound (6h). The base used varies depending on a starting material and is not particularly limited, but preferred examples include triethylamine, diisopropylethylamine, diazabicycloundecene, pyridine, sodium hydride, sodium hydroxide, potassium hydroxide, potassium carbonate, sodium carbonate, cesium carbonate, barium carbonate, sodium hydride, lithium hydride, sodium azide, and lithium diisopropylamide. The solvent used varies depending on a starting material, and solvents are not particularly limited so long as they do not inhibit a reaction and dissolve the starting material to some extent. Preferred examples thereof include acetonitrile, tetrahydrofuran, dimethyl sulfoxide, N,N-dimethylformamide, N-methylpyrrolidine, chloroform, dichloromethane, water, and mixtures thereof. The reaction temperature should be a temperature which is sufficient to complete a reaction without promoting formation of undesirable byproducts, and is preferably from −78 to 150° C., for example. Under preferable reaction conditions, this reaction is preferably completed in, for example, 1 to 24 hours, and the progress of a reaction can be monitored by known chromatography techniques. Undesirable byproducts can be removed by techniques known to those skilled in the art such as commonly used chromatography techniques, extraction operation, or/and crystallization.

The reaction of ii), that is, the ring formation reaction from diol or aminoalcohol at step 3-2 varies depending on a starting material and is not particularly limited so long as it is performed under conditions like those of this reaction. Methods known to those skilled in the art can be used, and preferred examples thereof include a method comprising stirring a compound (6h) suitably deprotected by a method known to those skilled in the art (refer to Greene T, and others, "Protective Groups in Organic Synthesis," John Wiley & Sons. Inc., New York, 1981) (here, $L_5$ represents hydroxyl group, and $X_1$ represents an oxygen atom, sulfur atom, or nitrogen atom) in a solvent in the presence of 0.1 to 10 equivalents of an acid or an organic metal reagent based on the compound (6h). The acid used varies depending on a starting material and is not particularly limited, but preferred examples thereof include organic acids such as paratoluenesulfonic acid and camphor sulfonic acid and inorganic acids such as sulfuric acid and hydrochloric acid. The metal reagent used varies depending on a starting material and is not particularly limited, but preferred examples thereof include tetrakis(triphenylphosphine)palladium and tris(triphenylphosphine)ruthenium. The solvent used varies depending on a starting material and the reagent used, and solvents are not particularly limited so long as they do not inhibit a reaction and dissolve the starting material to some extent. Preferred examples thereof include methylene chloride, chloroform, 1,4-dioxane, 1,2-dimethoxyethane, dimethyl sulfoxide, toluene, tetrahydrofuran, dimethylformamide, ethanol, methanol, and water, and mixed solvents thereof. Furthermore, the above-mentioned acid may be used as a solvent. The reaction temperature should be a temperature which is sufficient to complete a reaction without promoting formation of undesirable byproducts, and is preferably ice cold to 100° C., for example. Under preferable reaction conditions, this reaction is preferably completed in, for example, 1 to 24 hours, and the progress of a reaction can be monitored by known chromatography techniques. Undesirable byproducts can be removed by techniques known to those skilled in the art such as commonly used chromatography techniques, extraction operation, or/and crystallization.

The intramolecular reducing amination at step 3-3 varies depending on a starting material and is not particularly limited so long as it is performed under conditions like those of this reaction. Methods described in many publications (for example, refer to The Chemical Society of Japan, Ed., "Experimental Chemistry Lecture, Vol. 20, Organic Synthesis [II]," Maruzen Co., Ltd., July 1992, p. 300-302) can be used, and preferred examples thereof include a method comprising stirring a compound (6g) suitably deprotected by a method known to those skilled in the art (refer to Greene T, and others, "Protective Groups in Organic Synthesis," John Wiley & Sons. Inc., New York, 1981) (here, $P_1$ represents a hydrogen atom or an alkyl protection group such as benzyl group, allyl group, and trityl group) with 1.0 to 10.0 equivalents of a reducing agent based on the compound (6g) in a solvent in the presence of 1.0 to 30.0 equivalents of an acid based on the compound (6g). The acid used varies depending on a starting material and is not particularly limited, but preferred examples thereof include organic acids such as hydrochloric acid, formic acid, and acetic acid and Lewis acids such as trifluoroborane ether complex and titanium tetrachloride. The reducing agent used varies depending on a starting material and is not particularly limited, but preferred examples thereof include sodium borohydride, sodium cyanoboron hydride, sodium triacetoxyborohydride, and lithium aluminium hydride. The solvent used varies depending on a starting material and the reagent used, and solvents are not particularly limited so long as they do not inhibit a reaction and dissolve the starting material to some extent. Preferred examples thereof include ether solvents such as diethyl ether and tetrahydrofuran, halogenated solvents such as methylene chloride, 1,2-dichloroethane, and chloroform, nonpolar solvents such as toluene and xylene, and alcohol solvents such as methanol and ethanol. Furthermore, an acid such as acetic acid may be used as a solvent. The reaction temperature should be a temperature which is sufficient to complete a reaction without promoting formation of undesirable byproducts, and is preferably from −78 to 150° C., for example. Under preferable reaction conditions, this reaction is preferably completed in, for example, 0.5 to 24 hours, and progress of the reaction can be monitored by a known chromatography technique. Undesirable byproducts can be removed by techniques known to those skilled in the art such as commonly used chromatography techniques, extraction operation, or/and crystallization.

Alternatively, the intramolecular reducing amination at step 3-3 can also be performed by a contact reduction method. Preferred examples thereof include a method comprising stirring a compound (6g) suitably deprotected by a method known to those skilled in the art (refer to Greene T, and others, "Protective Groups in Organic Synthesis," John Wiley & Sons. Inc., New York, 1981) (here, $P_1$ represents a hydrogen atom) with a hydrogen source in a solvent in the presence of 0.01 to 1.0 equivalent of a metal catalyst based on the compound (6g). The metal catalyst used varies depending on a starting material and is not particularly limited, but preferred examples thereof include palladium-carbon, rhodium-carbon, ruthenium-carbon, palladium hydroxide, platinum oxide, Raney nickel, and Wilkinson catalyst. The hydrogen source varies depending on a starting material and the metal catalyst used and is not particularly limited, but preferred examples thereof include a hydrogen gas, formic acid, ammonium formate, and cyclohexadiene. The solvent used varies depending on a starting material and the metal catalyst and is not particularly limited, but preferred examples thereof include methanol, ethanol, ethyl acetate, toluene, THF, 1,4-dioxane, chloroform, methylene chloride, water, and mixtures thereof. Furthermore, to progress a reaction efficiently, organic acids, inorganic acids, or organic bases may be suitably added. The reaction temperature should be a temperature which is sufficient to complete a reaction without promoting formation of undesirable byproducts, and is preferably from room temperature to 150° C., for example. Under preferable reaction conditions, this reaction is preferably completed in, for example, 1 to 24 hours, and the progress of a reaction can be monitored by known chromatography techniques. Undesirable byproducts can be removed by techniques known to those skilled in the art such as commonly used chromatography techniques, extraction operation, or/and crystallization.

The reaction at step 3-4 consists of an addition reaction of Ar group by an organic metal reagent and a subsequent reduction reaction of the product. The addition reaction of Ar group by an organic metal reagent varies depending on a starting material and is not particularly limited so long as it is performed under conditions like those of this reaction. Known methods described in many publications can be used (for example, refer to The Chemical Society of Japan, Ed., "Experimental Chemistry Lecture, Vol. 25, Organic Synthesis [VII]," Maruzen Co., Ltd., September 1991, p. 9-82), and preferred examples thereof include a method comprising stirring a compound (6d) with 1.0 to 5.0 equivalents of an organic metal reagent based on the compound (6d) in a solvent. The organic metal reagent used varies depending on a starting material and is not particularly limited, but preferred examples thereof include organic magnesium reagents such as phenylmagnesium bromide, organic lithium reagents such as phenyllithium, and organic zinc reagents such as phenylzinc bromide. The solvent used varies depending on a starting material and the metal catalyst and is not particularly limited, but preferred examples thereof include toluene, THF, 1,4-dioxane, ether, and mixtures thereof. Furthermore, to progress a reaction efficiently, Lewis acids such as trifluoroborane ether complex may be suitably added. The reaction temperature should be a temperature which is sufficient to complete a reaction without promoting formation of undesirable byproducts, and is preferably from −78 to 150° C., for example. Under preferable reaction conditions, this reaction is preferably completed in, for example, 1 to 24 hours, and the progress of a reaction can be monitored by known chromatography techniques. Undesirable byproducts can be removed by techniques known to those skilled in the art such as commonly used chromatography techniques, extraction operation, or/and crystallization. The second stage, the reduction reaction of the product of the first stage, can be performed by techniques similar to those used in the intramolecular reducing amination at step 3-3.

Preparation of Compound (6h)

The compound (6h) can be prepared by subjecting a compound (6a) and a compound (6f) to a reducing amination reaction according to step 3-5. That is, the reaction at step 3-5 can be performed by techniques similar to those in the above-described intramolecular reducing amination at step 3-3.

Preferred examples include a method comprising stirring a compound (6a) suitably deprotected by a method known to those skilled in the art (refer to Greene T, and others, "Protective Groups in Organic Synthesis" John Wiley & Sons. Inc., New York, 1981) (here, $P_1$ represents a hydrogen atom or an alkyl protection group such as benzyl group, allyl group, or trityl group) with 1.0 to 3.0 equivalents of a compound (6f) based on the compound (6a) and 1.0 to 10.0 equivalents of a reducing agent based on the compound (6a) in a solvent in the presence of 1.0 to 30.0 equivalents of an acid based on the compound (6a). The acid used varies depending on a starting material and is not particularly limited, but preferred examples thereof include organic acids such as hydrochloric acid, formic acid, and acetic acid and Lewis acids such as trifluoroborane ether complex and titanium tetrachloride. The reducing agent used varies depending on a starting material and is not particularly limited, but examples thereof include sodium borohydride, hydride cyanoboron sodium, sodium triacetoxyborohydride, and lithium aluminium hydride. The solvent used varies depending on a starting material and the reagent used, and solvents are not particularly limited so long as they do not inhibit a reaction and dissolve the starting material to some extent. Preferred examples thereof include ether solvents such as diethyl ether and tetrahydrofuran, halogenated solvents such as methylene chloride, 1,2-dichloroethane, and chloroform, nonpolar solvents such as toluene and xylene, and alcohol solvents such as methanol and ethanol. Furthermore, an acid such as acetic acid may be used as a solvent. The reaction temperature should be a temperature which is sufficient to complete reactions without promoting formation of undesirable byproducts, and is preferably from −78 to 150° C., for example. Under preferable reaction conditions, this reaction is preferably completed in, for example, 0.5 to 24 hours, and the progress of a reaction can be monitored by known chromatography techniques. Undesirable byproducts can be removed by techniques known to those skilled in the art such as commonly used chromatography techniques, extraction operation, or/and crystallization.

Alternatively, the reducing amination at step 3-5 can be performed by a contact reduction method. Preferred examples thereof include a method comprising stirring a compound (6a) suitably deprotected by a method known to those skilled in the art (refer to Greene T, and others, "Protective Groups in Organic Synthesis," John Wiley & Sons. Inc., New York, 1981) (here, $P_1$ represents a hydrogen atom) and 1.0 to 3.0 equivalents of a compound (6f) based on the compound (6a) together with a hydrogen source in a solvent in the presence of 0.01 to 1.0 equivalent of a metal catalyst based on the compound (6a). The metal catalyst used varies depending on a starting material and is not particularly limited, but preferred examples thereof include palladium-carbon, rhodium-carbon, ruthenium-carbon, palladium hydroxide, platinum oxide, Raney nickel, and Wilkinson catalyst. The hydrogen source varies depending on a starting material and the metal catalyst used and is not particularly limited, but preferred examples thereof include a hydrogen gas, formic acid, ammonium formate, and cyclohexadiene. The solvent used varies depending on a starting material and the metal catalyst and is not particularly limited, but preferred examples thereof include methanol, ethanol, ethyl acetate, toluene, THF, 1,4-dioxane, chloroform, methylene chloride, water, and mixtures thereof. Furthermore, to progress a reaction efficiently, organic acids, inorganic acids, or organic bases may be suitably added. The reaction temperature should be a temperature which is sufficient to complete a reaction without promoting formation of undesirable byproducts, and is preferably from room temperature to 150° C., for example. Under preferable reaction conditions, this reaction is preferably completed in, for example, 1 to 24 hours, and the progress of a reaction can be monitored by known chromatography techniques. Undesirable byproducts can be removed by techniques known to those skilled in the art such as commonly used chromatography techniques, extraction operation, or/and crystallization.

Preparation of Compound (6g)

The compound (6g) can be prepared by subjecting a compound (6a) and a compound (6f) to a condensation reaction according to step 3-6. Alternatively, the compound (6g) can be prepared by reacting an organic metal reagent with a compound (6c) according to step 3-8.

The reaction at step 3-6 can be performed by techniques similar to those used at step 3-2. That is, step 3-6 can be performed by i) nucleophilic substitution reaction or ii) a ring formation reaction from diol or aminoalcohol.

The reaction of i), that is, the nucleophilic substitution reaction at step 3-6 varies depending on a starting material and is not particularly limited so long as it is performed under conditions like those of this reaction. Methods known to those skilled in the art can be used, and preferred examples thereof include a method comprising stirring a compound (6a) (here, $X_1$ represents an oxygen atom, a sulfur atom, or a nitrogen atom) and a compound (6f) (here, $L_5$ represents a fluorine atom, a chlorine atom, a bromine atom, an iodine atom, or a sulfonate group such as triflate) in a solvent in the presence of 1.0 to 10 equivalents of a base based on the compound (6a). The base used varies depending on a starting material and is not particularly limited, but preferred examples thereof include triethylamine, diisopropylethylamine, diazabicycloundecene, pyridine, sodium hydride, sodium hydroxide, potassium hydroxide, potassium carbonate, sodium carbonate, cesium carbonate, barium carbonate, sodium hydride, lithium hydride, sodium azide, and lithium diisopropylamide. The solvent used varies depending on a starting material, and solvents are not particularly limited so long as they do not inhibit a reaction and dissolve the starting material to some extent. Preferred examples thereof include acetonitrile, tetrahydrofuran, dimethyl sulfoxide, N,N-dimethylformamide, N-methylpyrrolidine, chloroform, dichloromethane, water, and mixtures thereof. The reaction temperature should be a temperature which is sufficient to complete a reaction without promoting formation of undesirable byproducts, and is preferably from −78 to 150° C., for example. Under preferable reaction conditions, this reaction is preferably completed in, for example, 1 to 24 hours, and the progress of a reaction can be monitored by known chromatography techniques. Undesirable byproducts can be removed by techniques known to those skilled in the art such as commonly used chromatography techniques, extraction operation, or/and crystallization.

The reaction of ii), that is, the ring formation reaction from diol or aminoalcohol at step 3-6 varies depending on a starting material and is not particularly limited so long as it is performed under conditions like those of this reaction. Methods known to those skilled in the art can be used, and preferred examples thereof include a method comprising stirring a compound (6a) (here, $X_1$ represents an oxygen atom, a sulfur atom, or a nitrogen atom) and 1.0 to 3.0 equivalents of a compound (6f) based on the compound (6a) (here, $L_5$ represents a hydroxyl group) in a solvent in the presence of 0.1 to 10 equivalents of an acid based on the compound (6a) or an organic metal reagent. The acid used varies depending on a starting material and is not particularly limited, but preferred examples thereof include organic acids such as paratoluenesulfonic acid, camphor sulfonic acid and inorganic acids such as sulfuric acid and hydrochloric acid. The metal reagent used varies depending on a starting material and is not particularly limited, but preferred examples thereof include tetrakis(triphenylphosphine)palladium and tris(triphenylphosphine)ruthenium. The solvent used varies depending on a starting material and the reagent used, and solvents are not particularly limited so long as they do not inhibit a reaction and dissolve the starting material to some extent. Preferred examples thereof include methylene chloride, chloroform, 1,4-dioxane, 1,2-dimethoxyethane, dimethyl sulfoxide, toluene, tetrahydrofuran, dimethylformamide, ethanol, methanol, water, and mixed solvents thereof. Furthermore, the above-described acid may be used as a solvent. The reaction temperature should be a temperature which is sufficient to complete a reaction without promoting formation of undesirable byproducts, and is preferably from ice cold to 100° C., for example. Under preferable reaction conditions, this reaction is preferably completed in, for example, 1 to 24 hours, and the progress of a reaction can be monitored by known chromatography techniques. Undesirable byproducts can be removed by techniques known to those skilled in the art such as commonly used chromatography techniques, extraction operation, or/and crystallization.

The reaction at step 3-8 varies depending on a starting material and is not particularly limited so long as it is performed under conditions like those of this reaction. Known methods described in many publications can be used (for example, refer to The Chemical Society of Japan, Ed., "Experimental Chemistry Lecture, Vol. 25, Organic Synthesis [VII]," Maruzen Co., Ltd., September 1991, p. 9-82), and preferred examples thereof include a method comprising stirring a compound (6c) and 1.0 to 5.0 equivalents of an organic metal reagent based on the compound (6c) in a solvent. The organic metal reagent used varies depending on a starting material and is not particularly limited, but preferred examples thereof include organic magnesium reagents such as phenylmagnesium bromide, organic lithium reagents such as phenyllithium, and organic zinc reagents such as phenylzinc bromide. The solvent used varies depending on a starting material and the metal catalyst and is not particularly limited, but preferred examples thereof include toluene, THF, 1,4-dioxane, ether, and mixtures thereof. Furthermore, to progress a reaction efficiently, a Lewis acid such as a trifluoroborane ether complex may be suitably added. The reaction temperature should be a temperature which is sufficient to complete a reaction without promoting formation of undesirable byproducts, and is preferably from −78 to 150° C., for example. Under preferable reaction conditions, this reaction is preferably completed in, for example, 1 to 24 hours, and the progress of a reaction can be monitored by known chromatography techniques. Undesirable byproducts can be removed by techniques known to those skilled in the art such as commonly used chromatography techniques, extraction operation, or/and crystallization.

Furthermore, when $L_3$ of the compound (6c) is an aldehyde group, an oxidation reaction of the generated alcohol compound is performed as a second step. The oxidation reaction varies depending on a starting material and is not particularly limited. Known methods described in many publications can be used (for example, refer to The Chemical Society of Japan Ed., "Experimental Chemistry Lecture, Vol. 21, Organic Synthesis [III]," Maruzen Co., Ltd., February 1991, p. 196-240), and preferred examples thereof include a method comprising stirring the alcohol compound generated at the first step with 1.0 to 50.0 equivalents of an oxidizing agent based on the alcohol compound in a solvent. The oxidizing agent used varies depending on a solvent, reaction temperature, and starting material and is not particularly limited, but preferred examples thereof include chromic acid oxidizing agents such as chromium oxide and dichromic acid, active manganese dioxide, dimethyl sulfoxide, periodic acid oxidizing agents such as Dess-Martin periodinane, and a mixture of an organic amine N-oxide such as 4-methylmorpholine N-oxide and tetrapropylammonium perruthenate. As the solvent used, solvents that do not inhibit a reaction and dissolve the starting material to some extent or mixed solvents thereof can be used, and preferred examples thereof include ether solvents such as tetrahydrofuran, 1,4-dioxane, and diethyl ether, halogen solvents such as methylene chloride, 1,2-dichloroethane, and chloroform, and nonpolar solvents such as toluene and benzene. The reaction temperature should be a temperature which is sufficient to complete a reaction without promoting formation of undesirable byproducts, and is preferably from −78 to 150° C., for example. Under preferable reaction conditions, this reaction is preferably completed in, for example, 1 to 24 hours, and the progress of a reaction can be monitored by known chromatography techniques. Undesirable byproducts can be removed by techniques known to those skilled in the art such as commonly used chromatography techniques, extraction operation, or/and crystallization.

Preparation of Compound (6d)

The compound (6d) is commercially available or otherwise can be prepared by subjecting a compound (6c) to an intramolecular amidation reaction according to step 3-9. That is, the intramolecular amidation reaction at step 3-9 varies depending on a starting material and is not particularly limited so long as it is performed under conditions like those of this reaction. Known techniques described in many publications can be used (for example, described in The Chemical Society of Japan, Ed., "Experimental Chemistry Lecture, Vol. 14, Synthesis and Reaction of Organic Compounds [II]," Maruzen Co., Ltd., February 1978, p. 1136-1162), and preferred examples include i) a technique in which a compound (6c) suitably deprotected by a method known to those skilled in the art (refer to Greene T, and others, "Protective Groups in Organic Synthesis," John Wiley & Sons. Inc., New York, 1981) (here, $L_3$ represents carboxylic acid) is converted to an acid halide, and then the acid halide is reacted under a basic condition (for example, described in The Chemical Society of Japan, Ed., "Experimental Chemistry Lecture, Vol. 14, Synthesis and Reaction of Organic Compounds [II]," Maruzen Co., Ltd., February 1978, p. 1142-1145) and ii) a technique in which a compound (6c) suitably deprotected by a method known to those skilled in the art (refer to Greene T, and others, "Protective Groups in Organic Synthesis," John Wiley & Sons. Inc., New York, 1981) (here, $L_3$ represents carboxylic acid, an ester group such as methyl ester, ethyl ester, tertiary butyl ester, or benzyl ester, a carbamate group such as a methoxymethylamide group or a pyrrolidineamide group, or a cyano group) is reacted using a condensing agent (for example, described in "Experiment Manual for Organic Chemistry [4]," Kagaku-dojin Publishing Company, Inc., September 1990, p. 27-52).

In the technique of i), the conversion reaction from the compound (6c) to an acid halide can be performed preferably by, for example, a technique in which the compound (6c) is stirred in a solvent in the presence of 1.0 to 10.0 equivalents of a halogenating agent based on the compound (6c). The halogenating agent used varies depending on a starting material and is not particularly limited, but preferred examples thereof include thionyl chloride, phosphorus pentachloride, and oxalyl chloride. The solvent used varies depending on a starting material, and solvents are not particularly limited so long as they do not inhibit a reaction and dissolve the starting material to some extent, and preferred examples thereof include methylene chloride, chloroform, and toluene. Furthermore, suitable addition of 0.1 to 1.0 equivalent of an organic base such as pyridine or dimethylformamide based on the compound (6c) may efficiently progress the reaction. The reaction temperature should be a temperature which is sufficient to complete a reaction without promoting formation of undesirable byproducts, and is preferably from ice cold to 150° C., for example. Under preferable reaction conditions, this reaction is preferably completed in, for example, 1 to 24 hours, and the progress of a reaction can be monitored by known chromatography techniques. Undesirable byproducts can be removed by techniques known to those skilled in the art such as commonly used chromatography techniques, extraction operation, or/and crystallization.

The subsequent coupling reaction can be performed preferably by, for example, a technique in which the acid halide is stirred in a solvent in the presence of 1.0 to 100.0 equivalents of a base based on the halide. The base used varies depending on a starting material and is not particularly limited, but preferred examples thereof include pyridine, triethylamine, N,N-diisopropylethylamine, lutidine, quinoline, and isoquinoline. The solvent used varies depending on a starting material, and solvents are not particularly limited so long as they do not inhibit a reaction and dissolve the starting material to some extent. Preferred examples thereof include methylene chloride, chloroform, toluene, tetrahydrofuran, and 1,4-dioxane. Furthermore, a base may be used as a solvent. Alternatively, a two-layer partitioning system of an alkaline aqueous solution, preferably, for example, an aqueous solution of sodium hydroxide or potassium hydroxide as the base, and a halogen solvent such as methylene chloride or 1,2-dichloroethane can be used. The reaction temperature should be a temperature which is sufficient to complete a reaction without promoting formation of undesirable byproducts, and is preferably from ice cold to 100° C., for example. Under preferable reaction conditions, this reaction is preferably completed in, for example, 1 to 24 hours, and the progress of a reaction can be monitored by known chromatography techniques. Undesirable byproducts can be removed by techniques known to those skilled in the art such as commonly used chromatography techniques, extraction operation, or/and crystallization.

The reaction of ii) can be performed preferably by a technique in which, for example, a compound (6c) is stirred in a solvent in the presence of 1.0 to 5.0 equivalents of a condensing agent based on the compound (6c). The condensing agent used varies depending on a starting material and is not particularly limited, but preferred examples thereof include 1,3-dicyclohexylcarbodiimide, 1-ethyl-3-(3'-dimethylaminopropyl)carbodiimide, benzotriazol-1-yloxytris(dimethylamino)phosphonium hexafluorophosphate, diethylcyanophosphonate, and bis(2-oxo-3-oxazolidinyl)phosphinic chloride. To progress the reaction efficiently, for example, 1.0 to 2.0 equivalents of N-hydroxysuccinimide or N-hydroxybenzotriazole based on a compound (7) may be preferably added. Furthermore, an acid such as hydrochloric acid, sulfuric acid, or methanesulfonic acid may be used as a condensing agent. This reaction is preferably performed in the presence of a solvent in view of operability and stirring efficiency. The solvent used varies depending on a starting material and the condensing agent used, and solvents are not particularly limited so long as they do not inhibit a reaction and dissolve the starting material to some extent. Preferred examples thereof include halogen solvents such as methylene chloride and 1,2-dichloroethane and polar solvents such as tetrahydrofuran and N,N-dimethylformamide. The reaction temperature should be a temperature which is sufficient to complete a reaction without promoting formation of undesirable byproducts, and is preferably from ice cold to 100° C., for example. Under preferable reaction conditions, this reaction is preferably completed in, for example, 1 to 24 hours, and the progress of a reaction can be monitored by known chromatography techniques. Undesirable byproducts can be removed by techniques known to those skilled in the art such as commonly used chromatography techniques, extraction operation, or/and crystallization.

Preparation of Compound (6c)

The compound (6c) can be prepared by subjecting a compound (6a) and a compound (6b) to condensation reaction according to step 3-7. The reaction at step 3-7 can be performed by techniques similar to those used at step 3-2. That is, the reaction at step 3-7 can be performed by i) a nucleophilic substitution reaction or ii) a ring formation reaction from diol or aminoalcohol.

The reaction of i), that is, the nucleophilic substitution reaction at step 3-7 varies depending on a starting material and is not particularly limited so long as it is performed under conditions like those of this reaction. Methods known to those skilled in the art can be used, and preferred examples thereof include a method comprising stirring a compound (6a) (here, $X_1$ represents an oxygen atom, sulfur atom, or nitrogen atom) and 1.0 to 3.0 equivalents of a compound (6b) based on the compound (6a) (here, $L_6$ represents a fluorine atom, a chlorine atom, a bromine atom, an iodine atom, or a sulfonate group such as triflate) in a solvent in the presence of 1.0 to 10 equivalents of a base based on the compound (6a). The base used varies depending on a starting material and is not particularly limited, but preferred examples thereof include triethylamine, diisopropylethylamine, diazabicycloundecene, pyridine, sodium hydroxide, potassium hydroxide, potassium carbonate, sodium carbonate, cesium carbonate, barium carbonate, sodium hydride, lithium hydride, sodium azide, and lithium diisopropylamide. The solvent used varies depending on a starting material, and solvents are not particularly limited so long as they do not inhibit a reaction and dissolve the starting material to some extent. Preferred examples thereof include acetonitrile, tetrahydrofuran, dimethyl sulfoxide, N,N-dimethylformamide, N-methylpyrrolidine, chloroform, dichloromethane, water, and mixtures thereof. The reaction temperature should be a temperature which is sufficient to complete a reaction without promoting formation of undesirable byproducts, and is preferably −78 to 150° C., for example. Under preferable reaction conditions, this reaction is preferably completed in, for example, 1 to 24 hours, and the progress of a reaction can be monitored by a known chromatography techniques. Undesirable byproducts can be removed by techniques known to those skilled in the art such as commonly used chromatography techniques, extraction operation, or/and crystallization.

The reaction of ii), that is, the ring formation reaction from diol or aminoalcohol at step 3-7 varies depending on a starting material and is not particularly limited so long as it is performed under conditions like those of this reaction. Methods known to those skilled in the art can be used, and preferred examples thereof include a method comprising stirring a compound (6a) (here, $X_1$ represents an oxygen atom, a sulfur atom, or a nitrogen atom) and 1.0 to 3.0 equivalents of a compound (6b) based on the compound (6a) (here, $L_6$ represents a hydroxyl group) in a solvent in the presence of 0.1 to 10 equivalents of an acid or an organic metal reagent based on the compound (6a). The acid used varies depending on the starting material and is not particularly limited, but preferred examples thereof include organic acids such as paratoluenesulfonic acid and camphor sulfonic acid and inorganic acids such as sulfuric acid and hydrochloric acid. The metal reagent used varies depending on a starting material and is not particularly limited, but preferred examples thereof include tetrakis(triphenylphosphine)palladium and tris(triphenylphosphine)ruthenium. The solvent used varies depending on a starting material and the reagent used, and solvents are not particularly limited so long as do not inhibit a reaction and dissolve the starting material to some extent. Preferred examples thereof include methylene chloride, chloroform, 1,4-dioxane, 1,2-dimethoxyethane, dimethyl sulfoxide, toluene, tetrahydrofuran, dimethylformamide, ethanol, methanol, water, and mixed solvents thereof. Furthermore, the above-mentioned acid may be used as a solvent. The reaction temperature should be a temperature which is sufficient to complete a reaction without promoting formation of undesirable byproducts, and is preferably from ice cold to 100° C., for example. Under preferable reaction conditions, this reaction is preferably completed in, for example, 1 to 24 hours, and the progress of a reaction can be monitored by known chromatography techniques. Undesirable byproducts can be removed by techniques known to those skilled in the art such as commonly used chromatography techniques, extraction operation, or/and crystallization.

Preparation of Compound (6a)

The compound (6a) is commercially available or otherwise can be prepared by methods known to those skilled in the art (for example, refer to Tetrahedron Letters, 1993, 34, p. 6513 or Tetrahedron Letters, 1995, 36, p. 1223).

Preparation of Compound (6b)

The compound (6b) is commercially available or otherwise can be prepared by methods known to those skilled in the art. Preferred examples thereof include bromoacetate ester derivatives.

Preparation of Compound (6f)

The compound (6f) is commercially available or otherwise can be prepared by methods known to those skilled in the art. Preferred examples thereof include phenacyl bromide derivatives.

General Production Method 2

The representative general production method 2 of the compound represented by the general formula (I) according to the present invention will be explained below.

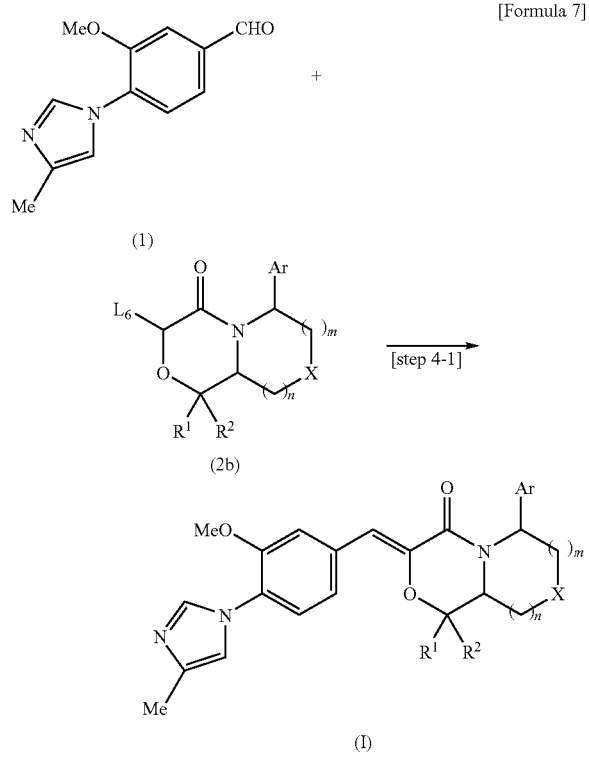

[Formula 7]

wherein Ar, $R^2$, m, $n^4$, and X have the same meanings as defined above, and $L_6$ represents a triphenylphosphonium group, a phosphite ester group, or a silyl group.

The above-shown general production method 2 is one example of a method for producing the compound represented by the general formula (I) by subjecting an aldehyde compound (1) and an amide compound (2b) to a condensation reaction at step 4-1.

Step 4-1

The condensation reaction at step 4-1 varies depending on a starting material and is not particularly limited so long as it is performed under conditions like those of this reaction. Known techniques described in many publications can be used, and examples thereof include Wittig reaction, Horner-Emmons reaction, and Peterson reaction (for example, described in The Chemical Society of Japan, Ed., "Experimental Chemistry Lecture, Vol. 19, Organic Synthesis [I]," Maruzen Co., Ltd., June 1992, p. 57-85).

The Wittig reaction is performed preferably by stirring, for example, a compound (2b) (here, $L_6$ represents triphenylphosphonium halide) and 0.8 to 1.5 equivalents of an aldehyde compound (1) based on the compound (2b) in a solvent in the presence of 1.0 to 5.0 equivalents of a base based on the compound (2b). This reaction is performed by i) a method comprising treating a compound (2b) and a base first to form phosphorus ylide and then adding an aldehyde compound (1) or ii) a method comprising adding a base with coexistence of a compound (2b) and an aldehyde compound (1). The solvent used varies depending on the starting material and the base used, and solvents are not particularly limited so long as they do not inhibit a reaction and dissolve the starting material to some extent. Preferred examples thereof include polar solvents such as nitromethane, acetonitrile, 1-methyl-2-pyrrolidone, N,N-dimethylformamide, and dimethyl sulfoxide, ether solvents such as tetrahydrofuran, 1,4-dioxane, and 1,2-dimethoxyethane, nonpolar solvents such as benzene, toluene, and xylene, alcohol solvents such as ethanol and methanol, halogen solvents such as chloroform and dichloromethane, water, and mixed solvents thereof. The base used varies depending on a starting material and the solvent, but preferred examples thereof include alkali metal hydroxides such as sodium hydroxide, potassium hydroxide, and lithium hydroxide, alkali metal carbonates such as sodium carbonate, sodium carbonate, and sodium hydrogencarbonate, alkali metal salts of alcohols such as sodium methoxide and potassium tertiary butoxide, organic bases such as triethylamine, pyridine, and diazabicyclononene, organic metals such as butyllithium and lithium diisobutylamide, and alkali metal hydrides such as sodium hydride. The reaction temperature should be a temperature which is sufficient to complete a reaction without promoting formation of undesirable byproducts, and is preferably from −78 to 150° C., for example. Under preferable reaction conditions, this reaction is preferably completed in, for example, 1 to 24 hours, and the progress of a reaction can be monitored by known chromatography techniques. Undesirable byproducts can be removed by techniques known to those skilled in the art such as commonly used chromatography techniques, extraction operation, or/and crystallization.

The Horner-Emmons reaction is preferably performed by, for example, stirring a compound (2b) (here, $L_5$ represents a phosphite ester) and 0.8 to 1.5 equivalents of an aldehyde compound (1) based on the compound (2b) in a solvent in the presence of 1.0 to 5.0 equivalents of a base based on the compound (2b). This reaction is performed by i) a method comprising treating a compound (2b) and a base first to form a carbanion and then adding an aldehyde compound (1) or ii) a method comprising adding a base with coexistence of a compound (2b) and an aldehyde compound (1). The solvent used varies depending on a starting material and the base used, and solvents are not particularly limited so long as they do not inhibit a reaction and dissolve the starting material to some extent. Preferred examples thereof include polar solvents such as 1-methyl-2-pyrrolidone, N,N-dimethylformamide, and dimethyl sulfoxide, ether solvents such as tetrahydrofuran, 1,4-dioxane, and 1,2-dimethoxyethane, nonpolar solvents such as benzene, toluene, and xylene, alcohol solvents such as ethanol and methanol, water, and mixed solvents thereof. The base used varies depending on a starting material and the solvent, but preferred examples include alkali metal hydroxides such as sodium hydroxide, potassium hydroxide, and lithium hydroxide, alkali metal carbonates such as sodium carbonate, potassium carbonate, and sodium hydrogencarbonate, alkali metal salts of alcohols such as sodium methoxide and potassium tertiary butoxide, organic bases such as triethylamine, pyridine, and diazabicyclononene, organic metals such as butyllithium and lithium diisobutylamide, alkali metal hydrides such as sodium hydride, and alkali metal ammonia salts such as sodium amide. The reaction temperature should be a temperature which is sufficient to complete a reaction without promoting formation of undesirable byproducts, and is preferably −78 to 150° C., for example. Under preferable reaction conditions, this reaction is preferably completed in, for example, 1 to 24 hours, and the progress of a reaction can be monitored by known chromatography techniques. Undesirable byproducts can be removed by techniques known to those skilled in the art such as commonly used chromatography techniques, extraction operation, or/and crystallization.

The Peterson reaction is preferably performed by stirring, for example, a compound (2b) (here, $L_6$ represents a silyl group) and 0.8 to 1.5 equivalents of an aldehyde compound (1) based on the compound (2b) in a solvent in the presence of 1.0 to 5.0 equivalents of a base based on the compound (2b). This reaction is performed by i) a method comprising treating a compound (2b) or a base first to form a carbanion and then adding an aldehyde compound (1) or ii) a method comprising adding a base with coexistence of a compound (2b) and an aldehyde compound (1). The solvent used vary depending on a starting material and the base used, and solvents are not particularly limited so long as they do not inhibit a reaction and dissolve the starting material to some extent. Preferred examples thereof include polar solvents such as 1-methyl-2-pyrrolidone, N,N-dimethylformamide, and dimethyl sulfoxide, ether solvents such as tetrahydrofuran, 1,4-dioxane, and 1,2-dimethoxyethane, nonpolar solvents such as benzene, toluene, and xylene, alcohol solvents such as ethanol and methanol, water, and mixed solvents thereof. The base used varies depending on a starting material and the solvent, but preferred examples thereof include alkali metal hydroxides such as sodium hydroxide, potassium hydroxide, and lithium hydroxide, alkali metal carbonates such as sodium carbonate, potassium carbonate, and sodium hydrogencarbonate, alkali metal salts of alcohols such as sodium methoxide and potassium tert-butoxide, organic bases such as triethylamine, pyridine, and diazabicyclononene, organic metals such as butyllithium and lithium diisobutylamide, alkali metal hydrides such as sodium hydride, and alkali metal ammonia salts such as sodium amide. The reaction temperature should be a temperature which is sufficient to complete a reaction without promoting formation of undesirable byproducts, and is preferably −78 to 150° C., for example. Under preferable reaction conditions, this reaction is preferably completed in, for example, 1 to 24 hours, and the progress of a reaction can be monitored by known chromatography techniques. Undesirable byproducts can be removed by techniques known to those skilled in the art such as commonly used chromatography techniques, extraction operation, or/and crystallization.

Preparation of Amide Compound (2b)

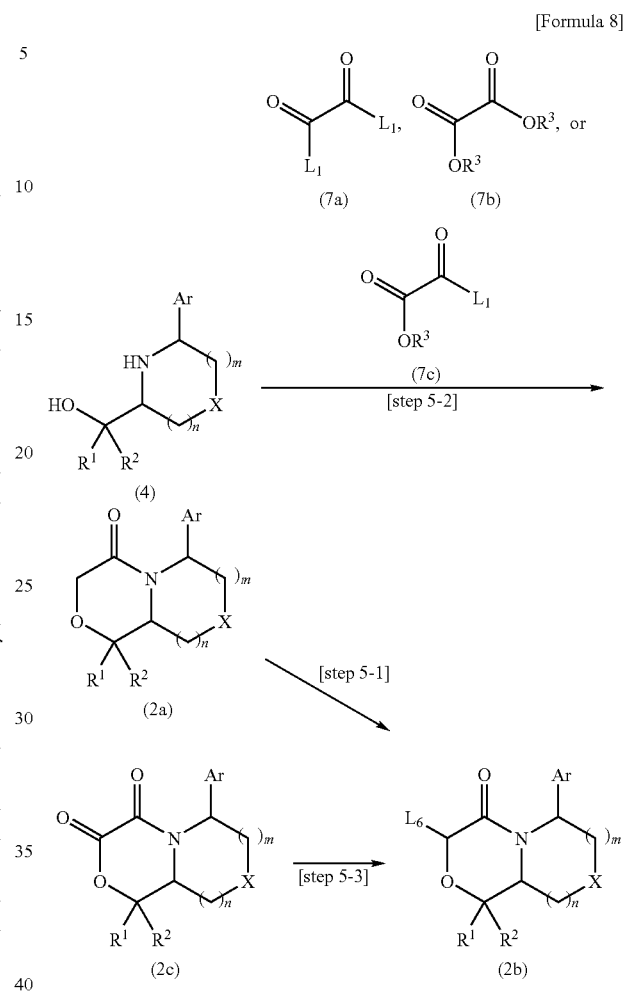

[Formula 8]

wherein Ar, $L_1$, $R^1$, $R^2$, m, n, and $L_6$ have the same meanings as defined above, and $R^3$ represents a lower alkyl group.

The above-shown reaction formula shows one example of methods for preparing an amide compound (2b). That is, the amide compound (2b) varies depending on a starting material and can be prepared by techniques known to those skilled in the art. Preferred examples thereof include a technique in which the amide compound (2b) is prepared according to step 5-1 using amide compound (2a) as a starting material and a technique in which compound (4) as a starting material is converted to compound (2c) at step 5-2, and then the amide compound (2b) is prepared at step 5-3.

Conversion from Amide Compound (2a) to Amide Compound (2b)

The reaction at step 5-1 varies depending on a starting material and is not particularly limited so long as it is performed under conditions like those of this reaction. Methods known to those skilled in the art can be used, and preferred examples of step 5-1 include i) Wittig reaction (here, $L_6$ represents triphenylphosphonium group), a technique in which an amide compound (2a) is halogenated by a method known to those skilled in the art (for example, described in The Chemical Society of Japan, Ed., "Experimental Chemistry Lecture, Vol. 19, Organic Synthesis [I]," Maruzen Co., Ltd., June 1992, p. 430-438) and reacted with triphenylphosphine (for example, refer to Organic Reaction, 1965, 14, p.

270). Alternatively, the reaction at step 5-1 is ii) Horner-Emmons reaction (here, $L_6$ represents a phosphite ester), a technique in which an amide compound (2a) is halogenated by a method known to those skilled in the art (for example, described in The Chemical Society of Japan, Ed., "Experimental Chemistry Lecture, Vol. 19, Organic Synthesis [I]," Maruzen Co., Ltd., June 1992, p. 430-438), and then the amide compound (2b) is prepared by Arbuzov reaction using an alkyl phosphinite (for example, refer to Chemical Review, 1981, 81, p. 415) or Becker reaction using a metal phosphonite (for example, refer to Journal of the American Chemical Society, 1945, 67, p. 1180). Alternatively, the reaction at step 5-1 can also be performed by a technique in which an amide compound (2b) is prepared from an amide compound (2a) and chlorophosphate in the presence of a base (for example, refer to Journal of Organic Chemistry, 1989, 54, p. 4750). Alternatively, the reaction at step 5-1 is iii) Peterson reaction (here, $L_6$ represents a silyl group), a technique in which an amide compound (2b) is prepared from an amide compound (2a) and trialkylsilyl chloride in the presence of a base (for example, refer to Journal of Organometallic Chemistry, 1983, 248, p. 51).

Conversion from an Amide Compound (2c) to an Amide Compound (2b)

The reaction at step 5-3 varies depending on a starting material and is not particularly limited so long as it is performed under conditions like those of this reaction, and methods known to those skilled in the art can be used. For example, the reaction at step 5-3 is preferably performed by a technique in which the carbonyl site of an ester is reduced to an alcohol compound (for example, described in The Chemical Society of Japan, Ed., "Experimental Chemistry Lecture, Vol. 26, Organic Synthesis [VIII]," Maruzen Co., Ltd., April 1992, p. 159-266), then converted to a halogen compound (for example, described in The Chemical Society of Japan, Ed., "Experimental Chemistry Lecture, Vol. 14, Syntheses and Reactions of Organic Compounds [I]," Maruzen Co., Ltd., November 1977, p. 331-450), subjected to a Wittig reagent (2b) (here, $L_6$ represents triphenylphosphonium group) (for example, refer to Organic Reaction, 1965, 14, p. 270) or Arbuzov reaction (for example, refer to Chemical Review, 1981, 81, p. 415) to obtain a Horner-Emmons reagent (2b) (here, $L_6$ represents a phosphite ester). Alternatively, an alcohol compound can be reacted with triallylphosphorus hydrobromide to be converted to the Wittig reagent (2b) (here, $L_6$ represents triphenylphosphonium group) (for example, refer to Synth. Commun., 1996, 26, p. 3091-3095 or Tetrahedron Lett., 2001, 42, p. 1309-1331).

Preparation of Amide Compound (2c)

The amide compound (2c) varies depending on a starting material and can be prepared by techniques known to those skilled in the art. For example, the amide compound (2c) can be preferably prepared according to step 5-2 using a compound (4) as a starting material. This step is preferably performed by, for example, vigorously stirring a compound (4) and 1.0 to 10 equivalents of a compound (7a) based on the compound (4) in a two-phase reaction solvent consisting of an organic solvent and a basic aqueous solution. The organic solvent used varies depending on a starting material and is not particularly limited, but solvents that do not inhibit a reaction and dissolve the starting material to some extent, or mixed solvents thereof can be preferably used. Preferred examples thereof include ether solvents such as diethyl ether, halogenated solvents such as methylene chloride, 1,2-dichloroethane, and chloroform, and nonpolar solvents such as toluene and xylene. The basic aqueous solution is preferably used in 1.0 or more equivalents based on the compound (4), and preferred examples include aqueous solutions of alkali metal salts such as sodium hydroxide, potassium hydroxide, sodium carbonate, potassium carbonate, cesium carbonate, and sodium hydrogencarbonate. The reaction temperature should be a temperature which is sufficient to complete a reaction without promoting formation of undesirable byproducts, and is preferably from −78° C. to room temperature, for example. Under preferable reaction conditions, this reaction is preferably completed in, for example, 0.5 to 24 hours, and the progress of a reaction can be monitored by known chromatography techniques. Undesirable byproducts can be removed by techniques known to those skilled in the art such as commonly used chromatography techniques, extraction operation, or/and crystallization.

Alternatively, the reaction at step 5-2 is preferably performed by, for example, stirring a compound (4) and 1.0 to 5.0 equivalents of a compound (7a) based on the compound (4) in a solvent in the presence of 1.0 to 5.0 equivalents of a base based on the compound (4). Preferred examples of the base used include organic amines such as triethylamine, isopropyl ethylamine, and pyridine. The solvent used varies depending on a starting material and is not particularly limited, but solvents that do not inhibit a reaction and dissolve the starting material to some extent are preferred. Preferred examples of organic solvents include ether solvents such as diethyl ether, halogenated solvents such as methylene chloride, 1,2-dichloroethane, and chloroform, and nonpolar solvents such as toluene and xylene. The reaction temperature should be a temperature which is sufficient to complete a reaction without promoting formation of undesirable byproducts, and is preferably −78 to 100° C., for example. Under preferable reaction conditions, this reaction is preferably completed in, for example, 0.5 to 24 hours, and the progress of a reaction can be monitored by known chromatography techniques. Undesirable byproducts can be removed by techniques known to those skilled in the art such as commonly used chromatography techniques, extraction operation, or/and crystallization.

Alternatively, the reaction at step 5-2 is preferably performed by, for example, stirring a compound (4) and 1.0 to 20 equivalents of a compound (7b) based on the compound (4) in a solvent. The solvent used varies depending on a starting material, and is not particularly limited. Solvents are not particularly limited so long as they do not inhibit a reaction and dissolve the starting material to some extent, and preferred examples thereof include ether solvents such as diethyl ether, halogenated solvents such as methylene chloride, 1,2-dichloroethane, and 1,2-dichlorobenzene, nonpolar solvents such as toluene and xylene, polar solvents such as dimethylformamide and N-methylpyrrolidone, and alcohol solvents such as methanol, ethanol, 2-propanol, and tertiary butanol. Alternatively, the reaction may be progressed conveniently without a solvent. The reaction temperature should be a temperature which is sufficient to complete a reaction without promoting formation of undesirable byproducts, and is preferably 50 to 200° C., for example. Under preferable reaction conditions, this reaction is preferably completed in, for example, 0.5 to 24 hours, and the progress of a reaction can be monitored by known chromatography techniques. Undesirable byproducts can be removed by techniques known to those skilled in the art such as commonly used chromatography techniques, extraction operation, or/and crystallization.

Alternatively, the reaction at step 5-2 is preferably performed by, for example, stirring a compound (5c) and 1.0 to 5.0 equivalents of a compound (7c) based on the compound (5c) in a solvent under the above-described reaction conditions or a combination thereof. Furthermore, for example, the reaction may be progressed conveniently by a phase-transfer catalyst, for example, quaternary ammonium salts such as tetrabutylammonium chloride and benzyltriethylammonium chloride or acidic compounds such as, for example, paratoluenesulfonic acid and camphor sulfonic acid.

Preparation of Compounds (7a), (7b), and (7c)

Compounds (7a), (7b), and (7c) are commercially available or otherwise can be prepared by methods known to those skilled in the art. If they are not commercially available, these compounds can be prepared by esterifying or halogenating corresponding oxalic acid derivatives by techniques known to those skilled in the art.

Since the compound represented by the general formula (I) of the present invention or a pharmacologically acceptable salt has an action of decreasing production of Aβ40 and Aβ42, it is effective as an agent for prophylactic or therapeutic treatment of diseases attributable to amyloid beta, in particular, as an agent for prophylactic or therapeutic treatment of neurodegenerative diseases attributable to Aβ such as Alzheimer's disease and Down's syndrome.

Furthermore, compounds included in the present invention are excellent in usefulness as drugs such as, for example, in vitro activity, in vivo activity, solubility, stability, pharmacokinetics, and toxicity.

The agent for prophylactic or therapeutic treatment of diseases attributable to Aβ according to the present invention can be formulated by usual methods, and preferred examples of the dosage form include tablets, powders, subtilized granules, granules, coated tablets, capsules, syrups, lozenges, inhalants, suppositories, injections, ointments, eye drops, eye ointments, nasal drops, ear drops, adhesive skin patches, and lotions. For formulation, for example, excipients, binders, lubricants, coloring materials, and flavoring agents that are usually used can be used, and stabilizers, emulsifiers, sorbefacients, surfactants, pH modulators, preservatives, antioxidant, and the like can be used, if necessary. The agent can be formulated by usual methods using ingredients commonly used as raw materials for drug formulation. Examples of these ingredients include animal and plant oils such as soybean oil, tallow, and synthetic glyceride; for example, hydrocarbons such as liquid paraffin, squalane, and solid paraffin; for example, ester oils such as octyldodecyl myristate and isopropyl myristate; for example, higher alcohols such as cetostearyl alcohol and behenyl alcohol; silicon resins; for example, silicon oil; surfactants such as polyoxyethylene fatty acid esters, sorbitan fatty acid esters, glycerine fatty acid esters, polyoxyethylene sorbitan fatty acid esters, hardened polyoxyethylene castor oil, and polyoxyethylene-polyoxypropylene block copolymers; for example, water-soluble polymers such as hydroxyethylcellulose, polyacrylic acids, carboxyvinyl polymers, polyethylene glycol, polyvinylpyrrolidone, and methylcellulose; for example, lower alcohols such as ethanol and isopropanol; for example, polyhydric alcohols such as glycerine, propylene glycol, dipropylene glycol, and sorbitol; sugars such as glucose and sucrose; for example, inorganic powders such as anhydrous silicic acid, aluminium silicate magnesium, and aluminium silicate, and purified water. Examples of excipients include lactose, corn starch, sucrose, glucose, mannitol, sorbit, crystalline cellulose, and silicon dioxide. Examples of binders include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, polypropylene glycol-polyoxyethylene-block polymers, and meglumine. Examples of disintegrating agents include starch, agar, gelatin powder, crystalline cellulose, calcium carbonate, sodium hydrogencarbonate, calcium citrate, dextrin, pectin, and carboxymethylcellulose-calcium. Examples of lubricants include magnesium stearate, talc, polyethylene glycol, silica, and hydrogenated vegetable oil. Examples of coloring materials include compounds permitted to add to drugs. As flavoring agents, cocoa powder, menthol, aromatic powder, peppermint oil, borneol, cinnamon powder, and the like are used.

For example, an oral preparation is prepared by a usual method as, for example, powders, subtilized granules, granules, tablets, coated tablets, or capsules, by adding a compound, an active ingredient, or a salt thereof or a hydrate thereof, excipients, and further, for example, binders, disintegrating agents, lubricants, coloring materials, and flavoring agents, if necessary. Tablet or granule may be suitably coated by sugar-coating, for example. Syrup, a preparation for injection, or the like is formulated by a usual method by adding, for example, pH modulators, solubilizing agents, and isotonizing agent, and, if necessary, dissolving aids, stabilizers, and the like. Furthermore, agents for external use can be prepared by usual methods, and production methods are not particularly limited. Various raw materials usually used in drugs, quasi-drugs, cosmetics, and the like can be used as vehicle raw materials. Examples thereof include raw materials such as animal and plant oils, mineral oils, ester oils, waxes, higher alcohols, fatty acids, silicon oil, surfactants, phospholipids, alcohols, polyhydric alcohols, water-soluble polymers, clay minerals, and purified water, and, if necessary, pH modulators, antioxidants, chelating agents, antiseptic-fungicide, artificial colors, flavors, and the like can be added. Furthermore, if necessary, ingredients having a differentiation inducing action such as ingredients of, for example, blood flow promoting agents, disinfectants, antiphlogistics, cell activating agents, vitamins, amino acids, moisturizing agents, and keratolytic agents can be added. The dose of the agent for therapeutic or prophylactic treatment according to the present invention depends on, for example, the severity of symptoms, age, sex, body weight, administration route, type of a salt, and specific disease type, but the usual daily dose for adults for oral administration is about 30 μg to 10 g, preferably 100 μg to 5 g, more preferably 100 μg to 100 mg of the compound represented by the general formula (I) of the present invention or a pharmacologically acceptable salt thereof, and that for injection is about 30 μg to 1 g, preferably 100 μg to 500 mg, more preferably 100 μg to 30 mg. The dose is administered once daily or divided into several times.

BEST MODE FOR CARRYING OUT THE INVENTION

Hereafter, the present invention will be explained more specifically with reference to the following examples and test examples. However, these examples are construed as examples, and the agent for prophylactic or therapeutic treatment of diseases attributable to Aβ of the present invention should be in no way limited to the following specific examples. Those skilled in the art can make various changes in not only the following examples and test examples, but also the claims defined by the present specification to make the best of the present invention, and such changes are encompassed in the scope of the claims defined by the present specification.

In the following Examples, the following abbreviations are used.
DMF: dimethylformamide
THF: tetrahydrofuran
LAH: lithium aluminum hydride
WSC: 1-ethyl-3-(3-dimethylaminopropyl)carbodiimide hydrochloride HOBT: 1-hydroxybenzotriazole
DIEA: diisopropylethylamine
TEA: triethylamine
TBAF: tetrabutylammonium fluoride
DBU: 1,8-diazabicyclo[5,4,0]undec-7-ene
t: tertiary

EXAMPLE 1 AND EXAMPLE 2

Synthesis of (Z)-(1R,6R,9aR)-3-[3-methoxy-4-(4-methylimidazol-1-yl)benzylidene]-1-methyl-6-(3,4,5-trifluorophenyl)tetrahydro-[1,4]oxazino[3,4-c][1,4]oxazin-4-one and (Z)-(1S,6R,9aR)-3-[3-methoxy-4-(4-methylimidazol-1-yl)benzylidene]-1-methyl-6-(3,4,5-trifluorophenyl)tetrahydro-[1,4]oxazino[3,4-c][1,4]oxazin-4-one

[Formula 9]

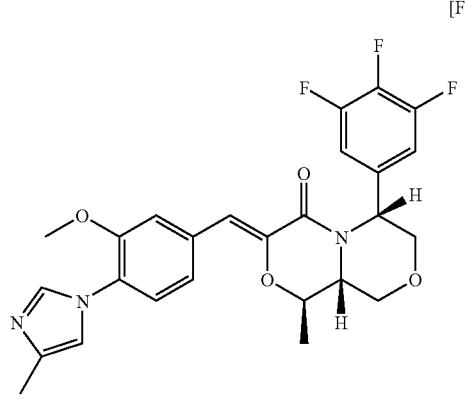

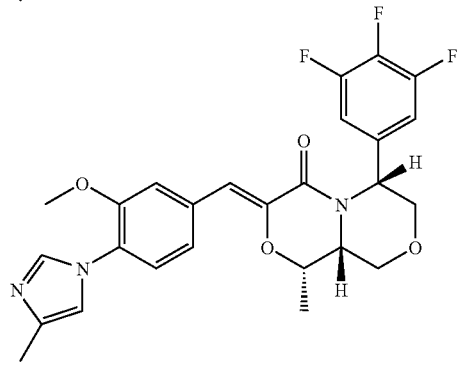

Synthesis of
(S)-3-benzloxy-2-t-butoxycarbonylaminopropoxy)
acetic acid t-butyl ester A 50% sodium hydroxide solution (350 ML) was added to a toluene (350 ML) solution containing boc-O-benzyl-L-serinol (89.5 g, CAS#120349-75-9). Under ice-cooling, tetrabutylammonium hydrogen sulfate (27 g) was added, and t-butyl bromoacetate ester (141 mL) was added dropwise at 15° C. or lower. After stirring for two hours at the same temperature, the temperature was raised to room temperature, and stirring was continued for 30 minutes. The resultant was diluted in ice cold water (350 ML) and toluene (350 ML). Water (300 ML) and toluene (300 ML) were further added, and the organic layer was partitioned. After the organic layer was washed with brine, it was dried over anhydrous magnesium sulfate. After removing the solvent under a vacuum, the partial purification product (136.8 g) containing the title compound was obtained. The physical property values are as follows.

ESI-MS; m/z 418 [M$^+$+Na]. $^1$H-NMR (CDCl$_3$) δ (ppm): 1.43 (s, 9H), 1.47 (s, 9H), 3.54-3.69 (m, 4H), 3.90-3.95 (m, 1H), 3.95 (d, J=3.6 Hz, 2H), 4.53 (s, 2H), 7.24-7.32 (m, 5H).

Synthesis of
(S)-5-benzyloxymethyl-morpholin-3-one

Trifluoroacetic acid (350 mL) was added to a dichloromethane (350 mL) solution containing (S)-3-benzyloxy-2-t-butoxycarbonylaminopropoxy)acetic acid t-butyl ester (126 g). The resultant was stirred at room temperature for 1.5 hours. After removing the solvent under a vacuum, the resultant was diluted in methanol (350 mL). Under ice cold conditions, thionyl chloride (117 mL) was added dropwise. The ice bath was removed and stirring was continued for 30 minutes at room temperature. The solvent was removed under a vacuum, and the resultant was diluted in methanol (350 mL). Under ice-cooling, sodium methoxide (196 mL, 28% methanol solution) was added dropwise. The ice bath was removed, and stirring was continued for 12 hours at room temperature. The solvent was removed under a vacuum, and the resultant was diluted in ethyl acetate (1 L) and washed with water (500 mL). Ethyl acetate (300 mL) was added to the aqueous layer, and the organic layer was partitioned. The organic layers were combined and washed with 2 N hydrochloric acid (500 mL). Ethyl acetate (300 mL) was added to the aqueous layer, and the organic layer was partitioned. The organic layers were combined and washed with brine. Ethyl acetate was added to the aqueous layer, the organic layer was partitioned, and the organic layers were combined and dried over anhydrous magnesium sulfate. The solvent was removed under a vacuum, and the title compound (64.15 g) was obtained. The physical property values are as follows.

ESI-MS; m/z 222 [M$^+$+H]. $^1$H-NMR (CDCl$_3$) δ (ppm): 3.43 (dd, J=9.2, 8.4 Hz, 1H), 3.55 (dd, J=9.2, 8.0 Hz, 1H), 3.63 (dd, J=11.6, 6.0 Hz, 1H), 3.73-3.77 (m, 1H), 3.87 (dd, J=11.6, 8.0 Hz, 1H), 4.11-4.21 (m, 2H), 4.51-4.57 (m, 2H), 6.41 (brs, 1H), 7.30-7.39 (m, 5H).

Synthesis of
(S)-3-benzyloxymethyl-5-oxomorpholine-4-carboxylic acid t-butyl ester Di-t-butyl dicarbonate (95.2 g), triethylamine (81.1 mL) and dimethyl amino pyridine (1.78 g) were added to an acetonitrile (600 mL) solution containing (S)-5-benzyloxymethyl-morpholin-3-one (64.15 g). Stirring was continued for 3 hours at room temperature. Imidazole (13.9 g) was added to the reaction solution, stirring was continued for 30 minutes at room temperature, and the solvent was removed under a vacuum. The resultant was diluted in ethyl acetate (700 mL), and the resultant was washed four times with cold 0.1 N hydrochloric acid (300 mL). The resultant was further washed in saturated sodium bicarbonate aqueous solution (400 mL) and brine (300 mL) in sequence. The organic layer was dried over anhydrous magnesium sulfate, and the solvent was removed under a vacuum, and the residue was passed through a silica pad (carrier: Chromatrex™ NH 700 cc, eluting solvent: ethyl acetate 2 L), and the solvent was removed under a vacuum, and the title compound (82.8 g) was obtained. The physical property values are as follows.

$^1$H-NMR (CDCl$_3$) δ (ppm): 1.50 (s, 9H), 3.57 (ddd, J=8.8, 4.8, 0.8 Hz, 1H), 3.65-3.75 (m, 2H), 4.10-4.28 (m, 4H), 4.52-4.59 (m, 2H), 7.25-7.38 (m, 5H).

Synthesis of {(S)-1-benzyloxymethyl-2-[2-oxo-2-(3, 4,5-trifluorophenyl)ethoxy]ethyl}carbamic acid t-butyl ester Under a nitrogen atmosphere, 1-bromo-3,4,5-trifluorobenzene (2 mL) was added to a diethyl ether (200 mL) suspension of magnesium (6.87 g) and iodine (trace amount) and the resultant was heated by heatgun until reaction started. 1-bromo-3,4,5-trifluorobenzene (31.7 mL) was further added dropwise. Once reflux has stopped, stirring was continued for 1.5 hours at room temperature. Under a nitrogen atmosphere, previously prepared 3,4,5-trifluorophenyl magnesium bromide was added dropwise at −35° C. or less into a tetrahydrofuran (800 mL) solution of (S)-3-benzyloxymethyl-5-oxomorpholine-4-carboxylic acid t-butyl ester (82.8 g) that was cooled to −40° C. Stirring was continued for 2 hours at −40° C., saturated ammonium chloride aqueous solution (200 mL) and water (300 mL) were added, and the temperature was raised to room temperature. Toluene (500 mL) was added, and the organic layer was partitioned. The organic layer was washed with brine. The aqueous layers were combined, ethyl acetate (400 mL) was added, and the organic layer was partitioned. The organic layers were combined and dried over anhydrous magnesium sulfate, and the solvent was removed under a vacuum. The residue was purified with silica gel column chromatography (heptane/ethyl acetate 9/1→8/2→3/1), and the title compound was obtained (82.6 g). The physical property values are as follows.

ESI-MS; m/z 476 [M$^+$+Na]. $^1$H-NMR (CDCl$_3$) δ (ppm): 1.43 (s, 9H), 3.52-3.72 (m, 4H), 3.92-4.01 (brm, 1H), 4.51 (s, 2H), 4.61 (s, 2H), 5.00-5.06 (brm, 1H), 7.26-7.35 (m, 5H), 7.58 (dd, J=7.6, 6.8 Hz, 2H).

Synthesis of [(3S,5R)-5-(3,4,5-trifluorophenyl)morpholin-3-yl]methanol

{(S)-1-benzyloxymethyl-2-[2-oxo-2-(3,4,5-trifluorophenyl)ethoxy]ethyl}carbamic acid t-butyl ester (82.6 g) was diluted with 4 N hydrochloric acid-ethyl acetate solution (500 mL), and the resultant was stirred at room temperature for 12 hours. The solvent was removed under a vacuum, and the resultant was dissolved in methanol (500 mL). 10% palladium on carbon (8.5 g, 50% water content) was added, and under a hydrogen atmosphere, stirring was continued for 22 hours. The catalyst was filtered off on celite, and the filtrate was concentrated under a vacuum. The residue was diluted with methanol (500 mL), and 20% palladium hydroxide on carbon (8 g, 50% water content) was added, and under a hydrogen atmosphere, stirring was continued for 4 hours. The catalyst was filtered off on celite, and the solvent was removed under a vacuum. Ethyl acetate (600 mL) and 1 N sodium hydroxide solution (250 mL) was added, and the organic layer was partitioned. The organic layer was washed with brine and dried over anhydrous magnesium sulfate. The residue was suspended in ether (80 mL) and the resultant was filtered, and the title compound (22.34 g) was obtained. The physical property values are as follows.

ESI-MS; m/z 248 [M$^+$+H]. $^1$H-NMR (CDCl$_3$) δ (ppm): 3.13-3.22 (m, 2H), 3.33 (dd, J=10.4, 10.4 Hz, 1H), 3.52 (dd, J=10.8, 6.4 Hz, 1H), 3.67 (dd, J=10.8, 4.0 Hz, 1H), 3.77 (dd, J=10.8, 3.2 Hz, 1H), 3.85 (dd, J=10.8, 3.2 Hz, 1H), 3.96 (dd, J=10.4, 3.2 Hz, 1H), 7.01-7.09 (m, 2H).

Synthesis of (3S,5R)-3-hydroxymethyl-5-(3,4,5-trifluorophenyl)morpholin-4-carboxylic acid 9H-fluoren-9-yl methyl ester Saturated sodium bicarbonate aqueous solution (290 mL) was added to a tetrahydrofuran (290 mL) solution of [(3S,5R)-5-(3,4,5-trifluorophenyl)morpholin-3-yl]methanol (21 g). Under ice-cooling, 9-fluorenyl methyl chloroformate (27.6 g) was added. Stirring was continued for 10 minutes at the same temperature and for 15 hours at room temperature. Toluene (300 mL) and water (250 mL) was added to the reaction solution, and the organic layer was partitioned. The organic layer was washed with brine and dried over anhydrous magnesium sulfate, and the solvent was removed under a vacuum. The residue was dissolved in ethyl acetate (160 mL), and while stirring, the resultant was heated to 60° C. Afterwards, the resultant was cooled gradually, and (3S,5R)-3-hydroxymethyl-5-(3,4,5-trifluorophenyl)morpholin-4-carboxylic acid 9H-fluoren-9-yl methyl ester (2 microspatulafulls) was added, and stirring was continued for 1 hour at room temperature. 800 mL of heptane was added dropwise, and stirring was continued for 1 hour at room temperature and 2 hours under ice-cooling. The resulting solid was collected by filtration, and the title compound (37.8 g) was obtained. The physical property values are as follows.

$^1$H-NMR (CDCl$_3$) δ (ppm): 2.80 (brs, 1H), 3.14 (q, J=8.0 Hz, 1H), 3.45 (dd, J=12.0, 4.0 Hz, 1H), 3.59-3.63 (m, 2H), 3.89 (d, J=11.6 Hz, 1H), 4.22-4.27 (m, 2H), 4.67 (dd, J=10.8, 4.4 Hz, 1H), 4.73 (brs, 1H), 4.89 (dd, J=10.8, 4.4 Hz, 1H), 6.97-7.01 (brm, 2H), 7.31-7.41 (m, 4H), 7.57 (d, J=7.2 Hz, 2H), 7.73 (d, J=7.6 Hz, 2H).

Synthesis of 1-[(3S,5R)-5-(3,4,5-trifluorophenyl)morpholin-3-yl]ethanol

Under a nitrogen atmosphere, a tetrahydrofuran (12.5 mL) solution containing dimethylsulfoxide (212 µL) was cooled to −78° C. Oxalyl chloride (243 µL) was added dropwise into the reaction solution, and stirring was continued for 5 minutes at the same temperature. A tetrahydrofuran (10 mL) solution containing (3S,5R)-3-hydroxymethyl-5-(3,4,5-trifluorophenyl)morpholin-4-carboxylic acid 9H-fluoren-9-yl methyl ester (1 g) was added dropwise into the reaction solution, and stirring was continued for 30 minutes at the same temperature. Triethylamine (1.48 mL) was added to the reaction solution. Stirring was continued for 30 minutes at the same temperature and for 1 hour at room temperature. Saturated ammonium chloride aqueous solution was added, and the resultant was extracted with toluene. The organic layer was dried over anhydrous magnesium sulfate, and the solvent was removed under a vacuum. The resulting residue was diluted with tetrahydrofuran (15 mL) and was cooled to −78° C. Methyl magnesium bromide (3.33 mL, 0.96 M tetrahydrofuran solution) was added dropwise into the reaction solution. Stirring was continued for 1 hour at the same temperature. Saturated ammonium chloride aqueous solution and ethyl acetate was added, and the organic layer was partitioned. The organic layer was washed with brine and dried over anhydrous magnesium sulfate. The solvent was removed under a vacuum, and tetrahydrofuran (10 mL) was added. Under ice-cooling, tetrabutyl ammonium fluoride (2.56 mL, 1 M tetrahydrofuran solution) was added dropwise, and stirring was continued for 2 hours at the same temperature. Water and ethyl acetate were added, and the organic layer was partitioned. The organic layer was washed with brine, and the resultant was dried over anhydrous magnesium sulfate. The solvent was removed under a vacuum, and the residue was purified with silica gel column chromatography (heptane/ethyl acetate system), and the title compound (269 mg) was obtained. The physical property values are as follows.

$^1$H-NMR (CDCl$_3$) δ (ppm): 1.22 (d, J=6.4 Hz, 0.75H), 1.23 (d, J=6.0 Hz, 2.25H), 2.88 (ddd, J=9.6, 6.4, 3.6 Hz, 0.25H), 3.03 (ddd, J=10.4, 3.6, 3.6 Hz, 0.75H), 3.11-3.17 (m, 1H), 3.31 (dd, J=10.4, 10.4 Hz, 0.25H), 3.42 (dd, J=10.8, 10.8 Hz, 0.75 Hz), 3.62-3.65 (m, 0.25H), 3.73-3.80 (m, 1.5H), 3.74-3.93 (m, 0.75H) 3.94-4.01 (m, 1.5H), 7.02-7.07 (m, 2H).

Synthesis of (6R,9aR)-1-methyl-6-(3,4,5-trifluorophenyl)tetrahydro-[1,4]oxazino[3,4-c][1,4]oxazin-3,4-dione Under ice-cooling, oxalyl chloride (0.27 mL) was added dropwise into a dichloromethane (5 mL) solution containing 1-[(3S,5R)-5-(3,4,5-trifluorophenyl)morpholin-3-yl]ethanol (269 mg) and pyridine (5 mL). Stirring was continued for 30 minutes at the same temperature and for 1 hour at room temperature. Water was added, and the organic layer was partitioned, and the resultant was dried over anhydrous magnesium sulfate. The solvent was removed under a vacuum, and the resultant was purified by silica gel column chromatography (heptane/ethyl acetate→ethyl acetate), and the title compound (136 mg) was obtained. The physical property values are as follows.
ESI-MS; m/z 316 [M$^+$+H]. $^1$H-NMR (CDCl$_3$) δ (ppm): 1.45 (d, J=6.4 Hz, 1H), 1.55 (d, J=6.8 Hz, 2H), 3.48-3.56 (m, 1H), 3.62-3.72 (m, 1H), 4.04-4.21 (m, 2H), 4.50 (ddd, J=11.2, 4.0, 3.6 Hz, 0.67H), 4.63-4.81 (m, 2.33H), 6.94-7.05 (m, 2H).

Synthesis of (Z)-(1R,6R,9aR)-3-[3-methoxy-4-(4-methylimidazol-1-yl)benzylidene]-1-methyl-6-(3,4,5-trifluorophenyl)tetrahydro-[1,4]oxazino[3,4-c][1,4]oxazin-4-one and (Z)-(1S,6R,9aR)-3-[3-methoxy-4-(4-methylimidozol-1-yl)benzylidene]-1-methyl-6-(3,4,5-trifluorophenyl)tetrahydro-[1,4]oxazino[3,4-c][1,4]oxazin-4-one A tetrahydrofuran (15 mL) solution containing (6R,9aR)-1-methyl-6-(3,4,5-trifluorophenyl)tetrahydro-[1,4]oxazino[3,4-c][1,4]oxazin-3,4-dione (536 mg) was cooled to −30° C. L-selectride (2.35 mL, 1.06 M tetrahydrofuran solution) was added dropwise, and stirring was continued for 2 hours at −20° C. to −30° C. A 5 N sodium hydroxide solution (356 µL) was added to the reaction solution, and stirring was continued for 20 minutes at −20° C. to 0° C. Next, hydrogen peroxide solution (173 µl, 35% aqueous solution) was added, and stirring was continued for 20 minutes at 0° C. Sodium bisulfite (186 mg) was added, and after stirring for 20 minutes at room temperature, ethyl acetate and brine were added, and the organic layer was partitioned. The organic layer was dried over anhydrous magnesium sulfate, and the solvent was removed under vacuum. Acetonitrile (15 mL) and triphenyl phosphonium bromide (624 mg) were added to the residue. The resultant was heated under reflux for 2 hours. The resultant was cooled to room temperature, and 3-methoxy-4-(4-methyl-1H-imidazol-1-yl)benzaldehyde (425 mg) and triethylamine (494 µl) were added, and stirring was continued for 12 hours at room temperature. The solvent was removed under a vacuum, and ethyl acetate and brine were added, and the organic layer was partitioned. The solvent was removed under a vacuum, and the residue was purified twice with silica gel column chromatography (carrier: Chromatrex™ NH, eluting solvent: hexane/ethyl acetate→ethyl acetate, and carrier: Chromatrex™ NH, eluting solvent: hexane/ethyl acetate→ethyl acetate→ethyl acetate/methanol). A diastereomixture of the title compound (404 mg) was obtained. The physical property values are as follows.
ESI-MS; m/z 500 [M$^+$+H].
The resulting diastereomixture (18.5 mg) was fractionated with ChiralPak™ IB made by Daicel (2 cm×25 cm: transition layer; hexane/ethanol 8/2), and an optically active title compound (4 mg) with a retention time of 82 minutes and an optically active title compound with a retention time of 92 minutes (8.3 mg) were obtained. The physical property values of the optically active title compound with retention time of 82 minutes are as follows.
$^1$H-NMR (CDCl$_3$) δ (ppm): 1.48 (d, J=6.4 Hz, 3H), 2.29 (s, 3H), 3.56 (dd, J=11.2, 11.2 Hz, 1H), 3.68 (dd, J=12.4, 6.8 Hz, 1H), 3.85 (s, 3H), 3.96-4.02 (m, 1H), 4.07 (dd, J=10.8, 4.4 Hz, 1H), 4.20 (dd, J=12.4, 4.4 Hz, 1H), 4.29 (dq, J=9.2, 6.4 Hz, 1H), 4.81 (dd, J=6.8, 4.4 Hz, 1H), 6.76 (s, 1H), 6.93 (s, 1H), 6.98 (dd, J=7.6, 6.8 Hz, 2H), 7.21 (d, J=8.0 Hz, 1H), 7.30 (dd, J=8.0, 1.2 Hz, 1H), 7.49 (d, J=1.2 Hz, 1H), 7.74 (s, 1H).

The physical property values of the optically active title compound with retention time of 92 minutes are as follows.
$^1$H-NMR (CDCl$_3$) δ (ppm): 1.49 (d, J=6.4 Hz, 3H), 2.29 (s, 3H), 3.50 (dd, J=11.6, 11.6 Hz, 1H), 3.68 (dd, J=12.4, 8.0 Hz, 1H), 3.84 (s, 3H), 4.03 (dd, J=11.2, 4.0 Hz, 1H), 4.19 (dd, J=12.0, 4.8 Hz, 1H), 4.41 (ddd, J=11.6, 3.6, 3.6 Hz, 1H), 4.54 (dq, J=13.2, 3.2 Hz, 1H), 4.79 (dd, J=8.0, 4.8 Hz, 1H), 6.83 (s, 1H), 6.92 (s, 1H), 7.03 (dd, J=8.0, 6.4 Hz, 2H), 7.20 (d, J=8.8 Hz, 1H), 7.35 (s, 1H), 7.36 (d, J=6, 8 Hz, 1H), 7.72 (s, 1H).

EXAMPLE 3

Synthesis of (Z)-(1S,6R,9aR)-6-(3,4-difluorophenyl)-3-[3-methoxy-4-(4-methylimidazol-1-yl)benzylidene]-1-methyl tetrahydro-[1,4]oxazino[3,4-c][1,4]oxazin-4-one

[Formula 10]

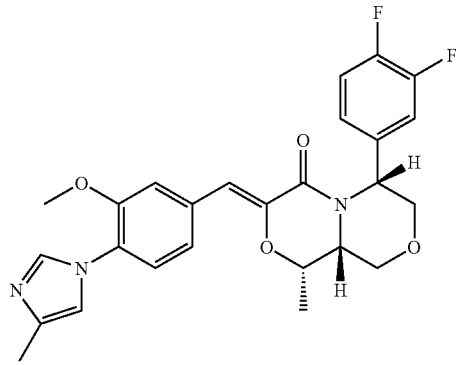

Synthesis of {(S)-2-benzyloxymethyl-1-[2-(3,4-difluorophenyl)-2-oxoethoxymethyl]ethyl}carbamic acid t-butyl ester Under a nitrogen atmosphere, 1-bromo-3,4-difluorobenzene (1.46 mL) was added dropwise into a tetrahydrofuran suspension containing magnesium (1.47 g) and iodine (trace amount), and the resultant was heated by heatgun. Once the reaction began, 1-bromo-3,4-difluorobenzene (10.2 mL) was added dropwise, and the resultant was further stirred for one hour at room temperature.

Under a nitrogen atmosphere, a tetrahydrofuran (100 mL) solution of (S)-3-benzyloxymethyl-5-oxomorpholine-4-carboxylic acid-t-butyl ester (16.2 g) obtained in Example 1 and Example 2 was cooled to −40° C., and the 3,4-difluorophenyl magnesium bromide prepared previously was added dropwise. After stirring for 30 minutes at the same temperature, a saturated ammonium chloride aqueous solution was added, and the resultant was extracted with ethyl acetate. After washing the organic layer with brine, the resultant was dried over anhydrous magnesium sulfate. The solvent was removed under a vacuum, and the title compound (22.2 g) was obtained. The physical property values are as follows.

ESI-MS; m/z 458 [M$^+$+Na].

Synthesis of (3R,5S)-3-(3,4-difluoronhenyl)-5-hydroxymethylmorpholin-4-carboxylic acid 9H-fluoren-9-yl methyl ester A 4 N hydrochloric acid/ethyl acetate solution (100 mL) was added to an ethyl acetate (50 mL) solution of {(S)-2-benzyloxymethyl-1-[2-(3,4-difluorophenyl)-2-oxoethoxymethyl]ethyl}carbamic acid t-butyl ester (26.8 g). Stirring was continued for 2.5 hours at room temperature. The solvent was removed under a vacuum, and azeotropic distillation with toluene was conducted twice. Ether/heptane mixture solution (1/1, 300 mL) was added to the residue, and the insoluble material was stimulated with a spatula and solidified. The supernatant was decanted out, and the residue was dried under vacuum. Methanol (200 mL) and 10% palladium on carbon (9.1 g, 50% water content) were added to the residue. Under a hydrogen atmosphere, stirring was continued for 18 hours. The catalyst was removed by filtration, and the solvent was removed under a vacuum. Ethyl acetate and saturated sodium bicarbonate aqueous solution were added, the organic layer was partitioned, and the resultant was washed with brine. The resultant was dried over anhydrous magnesium sulfate, and the solvent was removed under a vacuum. Tetrahydrofuran (120 mL) and saturated sodium bicarbonate aqueous solution (120 mL) were added to the resulting residue. Under ice-cooling, 9-fluorenylmethyl chloroformate (16.6 g) was added, and the resultant was raised to room temperature and was stirred for 14 hours. Ethyl acetate and water were added to the reaction solution, and the organic layer was partitioned, and after washing with brine, the resultant was dried over anhydrous magnesium sulfate. The solvent was removed under a vacuum, and the residue was diluted with ethyl acetate (50 mL). Heptane (5 mL) was added, and the resultant was left for 4 days at 4° C., The precipitated solid was collected by filtration, and the title compound (7.19 g) was obtained. The filtrate was purified by silica gel column chromatography (hexane/ethyl acetate 4/1→1/1), and again, the resultant was solidified with ethyl acetate. Through filtration, the title compound (3.69 g) was obtained. The physical property values are as follows.

ESI-MS; m/z 452 [M$^+$+H].

Synthesis of (3R,5R)-3-(3,4-difluorophenyl)-5-(1-hydroxyethyl)morpholine 4-carboxylic acid 9H-fluoren-9-yl methyl ester Under a nitrogen atmosphere, a tetrahydrofuran (35 mL) solution containing dimethyl sulfoxide (530 µL) was cooled to −78° C. Oxalyl chloride (608 µL) was added dropwise into the reaction solution, and stirring was continued for 5 minutes at the same temperature. A tetrahydrofuran (25 mL) solution containing (3R,5S)-3-(3,4-difluorophenyl)-5-hydroxymethyl morpholin-4-carboxylic acid 9H-fluoren-9-yl methyl ester (2.5 g) was added dropwise into the reaction solution. Stirring was continued for 30 minutes at the same temperature. Triethylamine (3.7 mL) was added to the reaction solution. Stirring was continued for 30 minutes at the same temperature and for 1 hour at room temperature. Saturated ammonium chloride aqueous solution was added, and extraction with ethyl acetate was conducted. The organic layer was dried over anhydrous magnesium sulfate, and the solvent was removed under a vacuum. The resulting residue was diluted with tetrahydrofuran (15 mL) and cooled to −78° C. Methylmagnesium bromide (8.33 mL, 0.97 M tetrahydrofuran solution) was added dropwise into the reaction solution, and stirring was continued for 1 hour at the same temperature. Saturated ammonium chloride aqueous solution and ethyl acetate was added, and the organic layer was partitioned. The organic layer was washed with brine and dried over anhydrous magnesium sulfate. The solvent was removed under a vacuum, and the residue was purified by silica gel column chromatography (heptane/ethyl acetate 95/5→1/1), and the title compound (950 mg) was obtained. The physical property values are as follows.

ESI-MS; m/z 488 [M$^+$+Na].

Synthesis of 1-[(3R,5R)-5-(3,4-difluorophenyl)morpholin-3-yl]ethanol

Diethylamine (4 mL) was added to an acetonitrile (16 mL) solution of (3R,5R)-3-(3,4-difluorophenyl)-5-(1-hydroxyethyl)morpholin 4-carboxylic acid 9H-fluoren-9-yl methyl ester (950 mg). Stirring was continued for 1 hour at room temperature. Toluene (20 mL) was added to the reaction solution, and the solvent was removed under a vacuum. The residue was purified by silica gel column chromatography (heptane/ethyl acetate 4/1→1/1), and the title compound (424 mg) was obtained. The physical property values are as follows.

ESI-MS; m/z 244 [M$^+$+H]. $^1$H-NMR (CDCl$_3$) δ (ppm): 1.22 (d, J=6.4 Hz, 3H), 3.00-3.48 (m, 3H), 3.73-3.80 (m, 2H), 3.90-4.03 (m, 2H), 7.08-7.12 (m, 2H), 7.24-7.29 (m, 1H).

Synthesis of (1S,6R,9aR)-6-(3,4-difluorophenyl)-1-methyl tetrahydro-[1,4]oxazino[3,4-c][1,4]oxazine-3,4-dione Under ice-cooling, oxalyl chloride (417 µL) was added dropwise into a dichloromethane (8 mL) solution of 1-[(3R,5R)-5-(3,4-difluorophenyl)morpholin-3-yl]ethanol (424 mg) and pyridine (2 mL). Stirring was continued for 30 minutes at the same temperature. Water was added to the reaction solution, and the organic layer was partitioned, and the resultant was dried with magnesium sulfate, and the solvent was removed under a vacuum. The residue was purified with silica gel column chromatography (heptane/ethyl acetate 9/1→1/4), and the title compound (353 mg) was obtained. The physical property values are as follows.

ESI-MS; m/z 298 [M$^+$+H]. $^1$H-NMR (CDCl$_3$) δ (ppm): 1.52 (d, J=6.4 Hz, 3H), 3.51 (dd, J=11.6, 11.6 Hz, 1H), 3.74 (dd, J=10.8, 8.4 Hz, 1H), 4.05 (dd, J=11.2, 4.4 Hz, 1H), 4, 18 (dd, J=12.4, 4.0 Hz, 1H), 4.54 (ddd, J=11.6, 4.0, 4.0 Hz, 1H), 4.66 (dq, J=13.2, 3.2 Hz, 1H), 4.86 (dd, J=7.2, 5.6 Hz, 1H), 7.13-7.23 (m, 3H).

Synthesis of (Z)-(1S,6R,9aR)-6-(3,4-difluorophenyl)-3-[3-methoxy-4-(4-methylimidazol-1-yl)benzylidene]-1-methyl tetrahydro-[1,4]oxazino[3,4-c][1,4]oxazin-4-one A tetrahydrofuran (10 mL) solution containing (1S,6R,9aR)-6-(3,4-difluorophenyl)-1-methyl tetrahydro-[1,4]oxazino[3,4-c][1,4]oxazine-3,4-dione (353 mg) was cooled to −30° C. L-selectride (1.55 mL, 1.06 M tetrahydrofuran solution) was added dropwise, and stirring was continued for 2 hours at −20° C. to −30° C. A 5 N sodium hydroxide aqueous solution (235 µL) was added to the reaction solution. Stirring was continued for 20 minutes at −20° C. to 0° C. Next, hydrogen peroxide solution (114 μL, 35% aqueous solution) was added, and stirring was continued for 20 minutes at 0° C. Sodium bisulfite (122 mg) was added, and after stirring for 20 minutes at room temperature, ethyl acetate and brine were added, and the organic layer was partitioned. The organic layer was dried over anhydrous magnesium sulfate, and the solvent was removed under vacuum Acetonitrile (10 mL) and triphenyl phosphonium bromide (410 mg) was added to the residue, and the resultant was heated under reflux for 2 hours. The resultant was cooled to room temperature, and 3-methoxy-4-(4-methyl-1H-imidazol-1-yl) benzaldehyde (280 mg) and triethylamine (326 μL) were added, and stirring was continued for 12 hours at room temperature. The solvent was removed under vacuum, and ethyl acetate and brine were added, and the organic layer was partitioned. The solvent was removed under vacuum, and the residue was purified by silica gel column chromatography (carrier: Chromatrex NH, eluting solvent: hexane/ethyl acetate→ethyl acetate), and the title compound (270 mg) was obtained. The physical property values are as follows.

ESI-MS; m/z 482 [M$^+$+H]. $^1$H-NMR (CDCl$_3$) δ (ppm): 1.48 (d, J=6.4 Hz, 3H), 2.29 (s, 3H), 3.51 (dd, J=11.2, 11.2 Hz, 1H), 3.73 (dd, J=12.4, 8.4 z, 1H), 3.83 (s, 3H), 4.00 (dd, J=11.6, 4.0 Hz, 1H), 4.19 (dd, J=12.0, 4.8 Hz, 1H), 4.41 (ddd, J=11.6, 3.6, 3.6 Hz, 1H), 4.53 (dq, J=13.2, 2.8 Hz, 1H), 4.85 (dd, J=8.4, 4.4 Hz, 1H), 6.82 (s, 1H), 6.91 (s, 1H), 7.10-7.23 (m, 4H), 7.33-7.36 (m, 2H), 7.69 (d, J=1.6 Hz, 1H).

EXAMPLE 4

Synthesis of (Z)-(6S,8aR)-6-(4-fluorophenyl)-3-[3-methoxy-4-(4-methylimidazol-1-yl)benzylidene]-1,1-dimethyltetrahydropyrrolo[2,1-c][1,4]oxazin-4-one

[Formula 11]

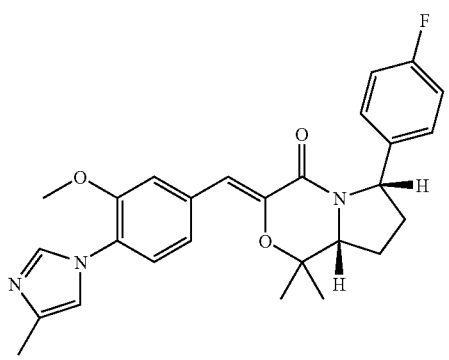

Synthesis of (R)-5-oxopyrrolidine-1,2-dicarboxylic acid 1-t-butyl ester 2-ethyl ester 4-dimethylaminopyridine (1.55 g) was added to a tetrahydrofuran (200 mL) solution containing D-pyroglutamic acid ethyl ester (20 g), triethylamine (35.2 mL) and di-t-butyl dicarbonate (30.5 g). Stirring was continued for 5 hours at room temperature. Imidazole (1.3 g) was added, and stirring was continued for 30 minutes at room temperature. The solvent was removed under a vacuum. The resultant was diluted with ethyl acetate, and the resultant was washed with 0.2 N hydrochloric acid three times and with brine, in sequence. The organic layer was dried over anhydrous magnesium sulfate, and the solvent was removed under a vacuum, and the title compound (31.08 g) was obtained. The physical property values are as follows.

$^1$H-NMR (CDCl$_3$) δ (ppm): 1.30 (t, J=7.2 Hz, 3H), 1.49 (s, 9H), 1.99-2.06 (m, 1H), 2.26-2.37 (m, 1H), 2.44-2.52 (m, 1H), 2.58-2.68 (m, 1H), 4.23 (q, J=7.2 Hz, 2H), 4.59 (dd, J=9.6, 3.2 Hz, 1H).

Synthesis of (R)-2-t-butoxycarbonylamino-5-(4-fluorophenyl)-5-oxovaleric acid ethyl ester Under a nitrogen atmosphere, 4-fluorophenyl magnesium bromide (25.6 mL, 1 M tetrahydrofuran solution) was added dropwise at −40° C. into a tetrahydrofuran (100 mL) solution containing (R)-5-oxopyrrolidine-1,2-dicarboxylic acid 1-t-butyl ester 2-ethyl ester (6 g). After stirring for 1 hour at the same temperature, saturated ammonium chloride aqueous solution was added, and the resultant was extracted with ethyl acetate. After washing the organic layer with brine, the resultant was dried over anhydrous magnesium sulfate. After removing the solvent under a vacuum, the residue was purified with silica gel column chromatography, and the title compound (6.33 g) was obtained. The physical property values are as follows.

ESI-MS; m/z 376 [M$^+$+Na]

Synthesis of (2R,5S)-5-(4-fluorophenyl)pyrrolidine-2-carboxylic acid ethyl ester A 4 N hydrochloric acid/ethyl acetate solution (90 mL) was added to (R)-2-t-butoxycarbonylamino-5-(4-fluorophenyl)-5-oxovaleric acid ethyl ester (6.33 g), and the resultant was stirred at room temperature for 2 hours. The solvent was removed under a vacuum, and ethanol (50 mL) and 10% palladium on carbon (6 g, 50% water content) was added, and under a hydrogen atmosphere, stirring was continued for 20 hours at room temperature. The catalyst was filtered off on celite, and the solvent was removed under vacuum. The resultant was diluted in ethyl acetate and washed with sodium bicarbonate aqueous solution and brine, in sequence. The solvent was removed under vacuum, and the resultant was purified with silica gel column chromatography (heptane/ethyl acetate), and the title compound (3.11 g) was obtained. The physical property values are as follows.

$^1$H-NMR (CDCl$_3$) δ (ppm): 1.30 (t, J=11.2 Hz, 3H), 1.62-1.72 (m, 1H), 2.04-2.24 (m, 3H), 3.90 (dd, J=8.8, 4.8 Hz, 1H), 4.18 (dd, J=9.2, 6.0 Hz, 1H), 4.22 (q, J=7.2 Hz, 2H), 6.97-7.02 (m, 2H), 7.38-7.42 (m, 2H).

Synthesis of (2R,5S)-5-(4-fluorophenyl)pyrrolidine-1,2-dicarboxylic acid 1-t-butyl ester 2-ethyl ester A dimethylformamide (30 mL) solution containing (2R, 5S)-5-(4-fluorophenyl)pyrrolidine-2-carboxylic acid ethyl ester (3.11 g), triethylamine (2.91 mL), and di-t-butyl dicarbonate (3.72 g) was stirred for 13 hours at room temperature. Imidazole (446 mg) was added to the reaction mixture, and stirring was continued for 30 minutes at room temperature, and the solvent was removed under a vacuum. Ethyl acetate was added to the residue, and the resultant was washed with 0.1 N hydrochloric acid, saturated sodium bicarbonate aqueous solution, brine, in sequence. The organic layer was dried over anhydrous magnesium sulfate. The solvent was removed under a vacuum, and the title compound (4.42 g) was obtained. The physical property values are as follows.

¹H-NMR (CDCl₃) δ (ppm): 1.15 (s, 4.5H), 1.32 (t, J=6.8 Hz, 1.5H), 1.34 (t, J=7.2 Hz, 1.5H), 1.40 (s, 4.5H), 1.84-1.96 (m, 1H), 1.96-2.08 (m, 1H), 2.18-2.24 (m, 1H), 2.25-2.33 (m, 1H), 4.25 (q, J=7.2 Hz, 2H), 4.33 (dd, J=6.8, 6.8 Hz, 0.5H), 4.46 (dd, J=8.4, 4.8 Hz, 0.5H), 4.71 (dd, J=8.0, 8.0 Hz, 0.5H), 4.91-4.97 (m, 0.5H), 6.97-7.01 (m, 2H), 7.50-7.54 (m, 2H).

Synthesis of 2-[(2R,5S)-5-(4-fluorophenyl)pyrrolidin-2-yl]propan-2-ol

Under ice-cooling, methylmagnesium bromide (16 mL, 0.97 M tetrahydrofuran solution) was added dropwise in a tetrahydrofuran (30 mL) solution containing (2R,5S)-5-(4-fluorophyenyl)pyrrolidine-1,2-dicarboxylic acid 1-t-butyl ester 2-ethyl ester (1.5 g). Stirring was continued for 30 minutes at the same temperature, and ammonium chloride aqueous solution and ethyl acetate were added, and the organic layer was partitioned. The organic layer was washed with brine, and the resultant was dried with magnesium sulfate, and the solvent was removed under a vacuum. 4 N hydrochloric acid/ethyl acetate (20 mL) was added to the residue, and stirring was continued for 3 hours. The solvent was removed under a vacuum, and ethyl acetate and sodium bicarbonate aqueous solution was added, and the organic layer was partitioned. The organic layer was washed with brine, and the resultant was dried over anhydrous magnesium sulfate, and the solvent was removed under a vacuum, and the title compound was obtained (994 mg). The physical property values are as follows.

ESI-MS; m/z 224 [M⁺+H]. ¹H-NMR (CDCl₃) δ (ppm): 1.19 (s, 3H), 1.20 (s, 3H), 1.53-1.63 (m, 1H), 1.77-184 (m, 1H), 1.86-1.94 (m, 1H), 2.03-2.14 (m, 1H), 3.18 (dd, J=8.4, 6.4 Hz, 1H), 4.22 (dd, J=8.8, 7.2 Hz, 1H), 6.96-7.01 (m, 2H), 7.32-7.37 (m, 2H).

Synthesis of (4R,6S)-6-(4-fluorophenyl)-1,1-dimethyltetrahydropyrrolo[2,1-c][1,4]oxazine-3,4-dione Under ice-cooling, oxalyl chloride (890 μL) was added dropwise into a dichloromethane (15 mL) solution containing 2-[(2R,5S)-5-(4-fluorophenyl)pyrrolidin-2-yl]propan-2-ol (1.16 g) and pyridine (5 mL). Stirring was continued for 1 hour at the same temperature. Water was added, and the organic layer was partitioned, and the resultant was dried over anhydrous magnesium sulfate. The solvent was removed under a vacuum, and the residue was purified by silica gel column chromatography (heptane/ethyl acetate), and the title compound (1.03 g) was obtained. The physical property values are as follows.

ESI-MS; m/z 278 [M⁺+H]. ¹H-NMR (CDCl₃) δ (ppm): 1.49 (s, 3H), 1.53 (s, 3H), 1.89-2.00 (m, 1H), 2.14-2.24 (m, 2H), 2.39-2.50 (m, 1H), 4.11 (dd, J=11.2, 5.6 Hz, 1H), 5.17 (d, J=9.2 Hz, 1H), 6.99-7.05 (m, 2H), 7.29-7.33 (m, 2H).

Synthesis of (Z)-(6S,8aR)-6-(4-fluorophenyl)-3-[3-methoxy-4-(4-methylimidazol-1-yl)benzylidene]-1,1-dimethyltetrahydropyrrolo[2,1-c][1,4]oxazin-4-one Under ice-cooling, L-selectride (4.52 mL, 1.02 M tetrahydrofuran solution) was added dropwise into a tetrahydrofuran (30 mL) solution containing (4R,6S)-6-(4-fluorophenyl)-1,1-dimethyltetrahydropyrrolo[2,1-c][1,4]oxazine-3,4-dione (1.03 g). Stirring was continued for 1 hour at the same temperature. A 5 N sodium hydroxide aqueous solution (686 μL) was added to the reaction solution, and stirring was continued for 20 minutes at 0° C., and next hydrogen peroxide solution (333 μL, 35% aqueous solution) was added, and stirring was continued for 20 minutes at 0° C. Sodium bisulfite (356 mg) was added, and after stirring for 20 minutes at room temperature, ethyl acetate and brine was added, and the organic layer was partitioned. The organic layer was dried over anhydrous magnesium sulfate, and the solvent was removed under a vacuum. Acetonitrile (30 mL) and triphenyl phosphonium bromide (1.2 g) were added to the residue, and the resultant was heated under reflux for 1 hour. The resultant was cooled to room temperature, and 3-methoxy-4-(4-methyl-1H-imidazol-1-yl)benzaldehyde (817 mg) and triethylamine (951 μL) was added, and stirring was continued for 10 hours at room temperature. The solvent was removed under a vacuum, and ethyl acetate and brine were added, and the organic layer was partitioned. The resultant was dried over anhydrous magnesium sulfate, and the solvent was removed under vacuum. Crude purification of the residue was conducted by silica gel column chromatography (carrier: Chromatrex NH, eluting solvent: hexane/ethyl acetate→ethyl acetate→ethyl acetate/methanol). The resulting solid was suspended in ethyl acetate, and diethyl ether was added, and the resultant was left overnight at 4° C. By filtering, the title compound (860 mg) was obtained. The physical property values are as follows.

ESI-MS; m/z 462 [M⁺+H]. ¹H-NMR (CDCl₃) δ (ppm): 1.45 (s, 3H), 1.58 (s, 3H), 1.82-1.93 (m, 1H), 2.02-2.14 (m, 2H), 2.29 (s, 3H), 2.33-2.44 (m, 1H), 3.84 (s, 3H), 3.94 (dd, J=12.0, 5.2 Hz, 1H), 5.16 (d, J=9.6 Hz, 1H), 6.77 (s, 1H), 6.91 (dd, J=1.2, 1.2 Hz, 1H), 6.98-7.03 (m, 2H), 7.17 (d, J=8.4 Hz, 1H), 7.28-7.31 (m, 3H), 7.53 (d, J=2.0 Hz, 1H), 7.69 (d, J=1.2 Hz, 1H).

EXAMPLE 5

Synthesis of (Z)-(1S,6R,9aR)-3-[3-methoxy-4-(4-methylimidazol-1-yl)benzylidene]-1-methyl-6-(4-chlorophenyl)hexahydropyrido[2,1-c][1,4]oxazin-4-one

[Formula 12]

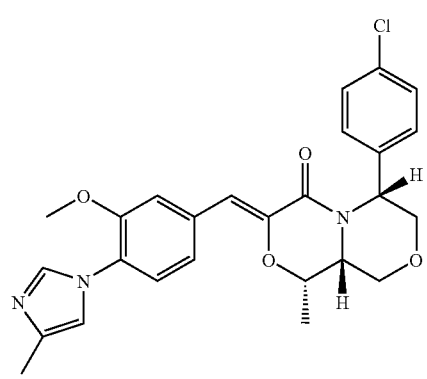

Synthesis of (R)-5-((R)-1-benzyloxyethyl)morpholin-3-one

A 50% sodium hydroxide solution (400 mL) and tetrabutylammoniumbisulfate (24.1 g) were added to a toluene (400 mL) solution of ((1R,2R)-2-benzyloxy-1-hydroxymethylpropyl) carbamic acid t-butyl ester (83.1 g, CAS#133565-43-2). Under ice-cooling, t-butyl bromoacetic acid ester (125 mL) was added dropwise, and stirring was continued for 3 hours at the same temperature. Water (500 mL) and toluene (500 mL) were added, and the organic layer was partitioned, and the resultant was washed with brine. The organic layer was dried over anhydrous magnesium sulfate, and the solvent was removed under a vacuum, and a crude material (122.5 g) containing ((2R,3R)-3-benzyloxy-2-t-butoxycarbonylaminobutoxy)acetic acid t-butyl ester was obtained. Dichloromethane (315 mL) and trifluoroacetic acid (315 mL) were added to the obtained crude material (118 q), and stirring was continued for 2 hours at room temperature. The solvent was removed under a vacuum, and methanol (350 mL) was added. Under ice-cooling, thionyl chloride (96.9 mL) was added dropwise, and the resultant was stirred at room temperature for 1 hour. The solvent was removed under a vacuum, and methanol (315 mL) was added, and under ice-cooling, sodium methoxide (165 mL, 28% methanol solution) was added dropwise. The solvent was removed under a vacuum, and ethyl acetate and water were added, and the organic layer was partitioned. The organic layer was washed with 1 N hydrochloric acid and brine in sequence, and the organic layer was dried over anhydrous magnesium sulfate. The solvent was removed under a vacuum, and the resultant was purified by silica gel column chromatography (ethyl acetate), and the title compound (61.57 g) was obtained. The physical property values are as follows.

ESI-MS; m/z 236 [M$^+$+H]. $^1$H-NMR (CDCl$_3$) δ (ppm): 1.21 (d, J=5.6 Hz, 3H), 3.44-3.52 (m, 3H), 3.90-4.95 (m, 1H), 4.04-4.21 (m, 2H), 4.40 (d, J=11.2 Hz, 1H), 4.66 (d, J=11.2 Hz, 1H), 6.51 (brs, 1H), 7.28-7.38 (m, 5H).

Synthesis of (R)-3-((R)-1-benzyloxyethyl)-5-oxomorpholine-4-carboxylic acid t-butyl ester Di-t-butyl dicarbonate (74.4 g), triethylamine (72.6 mL) and 4-dimethyl amino pyridine (1.6 g) were added in sequence to an acetonitrile (600 mL) solution of (R)-5-((R)-1-benzyloxyethyl)morpholin-3-one (61.6 g), and stirring was continued for 4 hours at room temperature. Imidazole (8.92 g) was added, and stirring was continued for 30 minutes at room temperature. The solvent was removed under a vacuum, and the resultant was diluted in ethyl acetate. The ethyl acetate solution was washed three times with cooled 0.1 N hydrochloric acid. Next, the resultant was washed with brine. The organic layer was dried over anhydrous magnesium sulfate, and the solvent was removed under a vacuum. The resulting solid was washed with hexane, and the title compound (69.97 g) was obtained. The physical property values are as follows.

$^1$H-NMR (CDCl$_3$) δ (ppm): 1.27 (d, J=6.0 Hz, 3H), 1.46 (s, 9H), 3.74 (dd, J=12.4, 3.2 Hz, 1H), 3.77-3.84 (m, 1H), 4.09-4.22 (m, 4H), 4.49 (d, J=12.0 Hz, 1H), 4.60 (d, J=12.0 Hz, 1H), 7.25-7.34 (m, 5H).

Synthesis of ((2R,3R)-3-benzyloxy-2-t-butoxycarbonylaminobutoxy)acetic acid

A 2 N sodium hydroxide solution (250 mL) was added to a methanol (250 mL) solution of (R)-3-((R)-1-benzyloxyethyl)-5-oxomorpholine-4-carboxylic acid t-butyl ester (40 g), and stirring was continued for 3 hours at room temperature. The methanol was removed under a vacuum, and ether was added, and the aqueous layer was partitioned. The aqueous layer was washed with ether, and the pH was adjusted to approximately pH 4 with a 5% citric acid solution. The resultant was extracted twice with ethyl acetate and washed twice with water. The organic layer was dried over anhydrous magnesium sulfate, and the solvent was removed under a vacuum, and the title compound (42.1 g) was obtained. The physical property values are as follows.

ESI-MS; m/z 376 [M$^+$+Na]. $^1$H-NMR (CDCl$_3$) δ (ppm): 1.24 (d, J=6.4 Hz, 3H), 1.44 (s, 9H), 3.54-3.63 (m, 2H), 3.77-3.80 (brm, 2H), 4.04 (s, 1H), 4.04 (s, 1H), 4.38 (d, J=11.6 Hz, 1H), 4.61 (d, J=11.2 Hz, 1H), 4.98 (brd, J=3.6 Hz, 1H), 7.25-7.36 (m, 5H).

Synthesis of {(1R,2R)-2-benzyloxy-1-{(methoxymethylcarbamoyl)methoxylmethyl]propyl}carbamic acid t-butyl ester N,N-diisopropylethylamine (41 mL), N,O-dimethylhydroxyamine hydrochloride (17.4 g), EDCI (34.3 g), HOBt (24.1 g) were added in sequence to a DMF (400 mL) solution of ((2R,3R)-3-benzyloxy-2-t-butoxycarbonylaminobutoxy) acetic acid (42.1 g), and stirring was continued for 16 hours at room temperature. The solvent was removed under a vacuum, and ethyl acetate and water were added, and the organic layer was partitioned. The organic layer was washed with brine and dried over anhydrous magnesium sulfate, and the solvent was removed under a vacuum. After passing the residue through a silica pad (silica gel 500 cc), the solvent was removed under a vacuum, and the title compound (46.0 g) was obtained. The physical property values are as follows.

ESI-MS; m/z 419 [M$^+$+Na]. $^1$H-NMR (CDCl$_3$) δ (ppm): 1.23 (d, J=6.4 Hz, 3H), 1.43 (s, 9H), 3.17 (s, 3H), 3.58 (dd, J=9.6, 5.6 Hz, 1H), 3.63-3.64 (m, 1H), 3.66 (s, 3H), 3.78-3.84 (m, 1H), 3.90-3.98 (m, 1H), 4.24 (s, 2H), 4.48 (d, J=11.2 Hz, 1H), 4.61 (d, J=11.2 Hz, 1H), 5.02 (d, J=8.4 Hz, 1H), 7.25-7.33 (m, 5H).

Synthesis of {(1R,2R)-2-benzyloxy-1-[2-(4-chlorophenyl)-2-oxoethoxymethyl]propyl}carbamic acid t-butyl ester A tetrahydrofuran (50 mL) solution of {(1R,2R)-2-benzyloxy-1-[(methoxymethylcarbomoyl)methoxymethyl] propyl}carbamic acid t-butyl ester (2.42 g) was cooled to −40° C., and 4-chlorophenyl magnesium bromide (18.3 mL, 1 M tetrahydrofuran solution) was added dropwise. Stirring was continued for 1 hour at −40° C., and afterwards, the temperature was gradually raised to 0° C., and saturated ammonium chloride aqueous solution was added. Extraction with ethyl acetate was conducted, and after washing the organic layer with brine, the resultant was dried over anhydrous magnesium sulfate. The solvent was removed under a vacuum, and the residue was purified by silica gel column chromatography (heptane/ethyl acetate 9/1→1/1), and the title compound (2.61 g) was obtained. The physical property values are as follows.

ESI-MS; m/z 470 [M$^+$+Na]. $^1$H-NMR (CDCl$_3$) δ (ppm): 1.23 (d, J=6.4 Hz, 3H), 1.43 (s, 9H), 3.55-3.65 (m, 2H), 3.79-3.86 (m, 2H), 4.39 (d, J=11.2 Hz, 1H), 4.58-4.64 (m, 3H), 4.92 (brd, J=9.2 Hz, 1H), 7.25-7.32 (m, 5H), 7.41 (d, J=8.4 Hz, 2H), 7.84 (d, J=8.4 z, 2H).

Synthesis of (3R,5R)-3-((R)-1-benzyloxyethyl)-5-(4-chlorophenyl)morpholin

A 4 N hydrochloric acid/ethyl acetate solution (40 mL) of {(1R,2R)-2-benzyloxy-1-[2-(4-chlorophenyl)-2-oxoethoxymethyl]propyl}carbamic acid t-butyl ester (2.61 g) was stirred for 1 hour at room temperature. The solvent was removed under a vacuum, and methanol (30 mL) was added. Under ice-cooling, sodium cyanoborohydride (733 mg) was added, and the resultant was stirred overnight at room temperature. The solvent was removed under a vacuum, and the resultant was diluted with ethyl acetate and washed with saturated sodium bicarbonate aqueous solution and brine in sequence, and the organic layer was dried over anhydrous magnesium sulfate. The solvent was removed under a vacuum, and the residue was purified with silica gel column chromatography (heptane/ethyl acetate 95/5→3/2), and the title compound (1.435 g) was obtained. The physical property values are as follows.

ESI-MS; m/z 332 [M$^+$+H]. $^1$H-NMR (CDCl$_3$) δ (ppm): 1.20 (d, J=6.4 Hz, 3H), 2.97 (ddd, J=10.4, 8.4, 3.2 Hz, 1H), 3.18 (dd, J=10.4, 10.4 Hz, 1H), 3.24 (dd, J=10.8, 10.8 Hz, 1H), 3.37-3.44 (m, 1H), 3.74 (dd, J=10.8, 3.2 Hz, 1H), 3.85 (m, 2H), 4.42 (d, J=11.2 Hz, 1H), 4.64 (d, J=11.2 Hz, 1H), 7.26-7.31 (m, 9H).

Synthesis of (R)-1-[(3R,5R)-5-(4-chlorophenyl)morpholin-3 yl]ethanol

Trimethylsilyl iodide (3.07 mL) was added to a dichloromethane (20 mL) solution of (3R,5R)-3-((R)-1-benzyloxyethyl)-5-(4-chlorophenyl)morpholin (1.44 g). Stirring was continued for 10 hours at room temperature. Additional trimethylsilyl iodide (3.07 mL) was added, and the resultant was stirred at room temperature for 4 days. Additional trimethylsilyl iodide (3.07 mL) was further added, and stirring was continued for 1 day. Additional trimethylsilyl iodide (3.07 mL) was further added, and stirring was continued for 10 hours at room temperature. A 5 N sodium hydroxide solution was added, and the organic layer was partitioned. The organic layer was dried over anhydrous magnesium sulfate. The resultant was purified with silica gel column chromatography (heptane/ethyl acetate). The title compound (903 mg) was obtained. The physical property values are as follows.

$^1$H-NMR (CDCl$_3$) δ (ppm): 1.21 (d, J=6.0 Hz, 3H), 2.90 (ddd, J=10.0, 5.6, 2.4 Hz, 1H), 3.22 (dd, J=10.4, 10.4 Hz, 1H), 3.36 (dd, J=10.8, 10.8 Hz, 1H), 3.60-3.67 (m, 1H), 3.77 (dd, J=10.8, 3.2 Hz, 1H), 3.86 (dd, J=10.8, 3.2 Hz, 1H), 3.96 (dd, J=10.4 z, 3.2 Hz, 1H), 7.26-7.36 (m, 4H).

Synthesis of 4-nitrobenzoic acid (S)-1-[(3R,5R)-5-(4-chlorophenyl)morpholin-3-yl]ethyl ester Under a nitrogen atmosphere and under ice-cooling, diisopropylazodicarboxylate (1.36 mL) was added dropwise in a tetrahydrofuran solution containing (R)-1-[(3R,5R)-5-(4-chlorophenyl)morpholin-3-yl]ethanol (903 mg), triphenylphosphine (1.81 g), and 4-nitrobenzoic acid (1.16 g). Stirring was continued for 30 minutes at the same temperature and for 2 hours at room temperature. Water and ethyl acetate was added to the reaction solution, and the organic layer was partitioned. The organic layer was washed with brine and was dried over anhydrous magnesium sulfate. The solvent was removed under a vacuum, and the residue was purified by silica gel column chromatography (heptane/ethyl acetate 9/1→8/2→7/3), and the title compound (1.46 g) was obtained. The physical property values are as follows.

$^1$H-NMR (CDCl$_3$) δ (ppm): 1.44 (d, J=6.4 Hz, 3H), 3.21 (dd, J=10.8, 10.8 Hz, 1H), 3.32 (ddd, J=10.0, 4.8, 2.4 Hz, 1H), 3.40 (dd, J=10.4, 10.4 Hz, 1H), 3.78 (dd, J=10.8, 3.2 Hz, 1H), 3.97-4.02 (m, 2H), 5.18-5.24 (m, 1H), 7.28 (d, J=8.4 Hz, 2H), 7.33 (d, J=8.4 Hz, 2H), 8.19 (d, J=8.8 Hz, 2H), 8.30 (d, J=8.8 Hz, 2H).

Synthesis of (S)-1-[(3R,5R)-5-(4-chlorophenyl)morpholin-3 yl]ethanol

Sodium methoxide (1.9 mL, 28% methanol solution) was added to a methanol (40 mL) solution of 4-nitrobenzoic acid (S)-1-[(3R,5R)-5-(4-chlorophenyl)morpholin-3 yl]ethyl ester (1.46 g). Stirring was continued for 1 hour at room temperature. The solvent was removed under a vacuum, and ethyl acetate and water were added, and the organic layer was partitioned. The organic layer was washed with brine, and the resultant was dried over anhydrous magnesium sulfate. The solvent was removed under a vacuum, and the residue was purified by silica gel column chromatography (heptane/ethyl acetate 9/1→1/3), and the title compound (833 mg) was obtained. The physical property values are as follows.

ESI-MS; m/z 242 [M$^+$+H]. $^1$H-NMR (CDCl$_3$) δ (ppm): 1.22 (d, J=6.8 Hz, 3H), 2.49 (brs, 1H), 3.03 (ddd, J=10.0, 3.2, 3.2 Hz, 1H), 3.20 (dd, J=10.4, 10.4 Hz, 1H), 3.46 (dd, J=3.2, 3.2 Hz, 1H), 3.74-3.79 (m, 2H), 3.96 (dd, J=11.2, 3.2 Hz, 1H), 4.03 (dd, J=10.0, 3.2 Hz, 1H), 7.28-7.35 (m, 4H).

Synthesis of (1S,6R,9aR)-6-(4-chlorophenyl)-1-methyltetrahydro-[1,4]oxazino[3,4-c][1,4]oxazine-3,4-dione Under ice-cooling, oxalyl chloride (833 µL) was added dropwise into a dichloromethane (15 mL) solution of (S)-1-[(3R,5R)-5-(4-chlorophenyl)morpholin-3 yl]ethanol (833 mg) and pyridine (4 mL). Stirring was continued for 30 minutes at the same temperature and for 1 hour at room temperature. Water was added to the reaction solution, and the organic layer was partitioned. The resultant was dried over anhydrous magnesium sulfate, and the solvent was removed under a vacuum. The residue was purified by silica gel column chromatography (heptane/ethyl acetate→ethyl acetate), and the title compound (686 mg) was obtained. The physical property values are as follows.

ESI-MS; m/z 296 [M$^+$+H]. $^1$H-NMR (CDCl$_3$) δ (ppm): 1.51 (d, J=6.4 Hz, 3H), 3.52 (dd, J=12.0, 12.0 Hz, 1H), 3.78 (dd, J=12.4, 8.0 Hz, 1H), 4.02 (dd, J=11.6, 4.4 Hz, 1H), 4.18 (dd, J=12.4, 4.8 Hz, 1H), 4.51 (ddd, J=11.2, 4.0, 4.0 Hz, 1H), 4.61-4.67 (m, 1H), 4.89 (dd, J=8.0, 4.8 Hz, 1H), 7.32 (s, 4H).

Synthesis of (Z)-(1S,6R,9aR)-3-[3-methoxy-4-(4-methylimidazol-1-yl)benzylidene]-1-methyl-6-(4-chlorophenyl)hexahydropyrido[2,1-c][1,4]oxazin-4-one A tetrahydrofuran (20 mL) solution containing (1S,6R, 9aR)-6-(4-chlorophenyl)-1-methyltetrahydro-[1,4]oxazino [3,4-c][1,4]oxazine-3,4-dione (685 mg) was cooled to −30° C. L-selectride (3.01 mL, 1.02 M tetrahydrofuran solution) was added dropwise, and stirring was continued for 2 hours at −20° C. to −30° C. 5 N sodium hydroxide solution (40 was added to the reaction solution, and stirring was continued for 20 minutes at −20° C. to 0° C. Next, hydrogen peroxide solution (221 µL, 35% solution) was added, and stirring was continued for 20 minutes at 0° C. Sodium bisulfite (237 mg) was added, and after stirring at room temperature for 20 minutes, ethyl acetate and brine were added, and the organic layer was partitioned. The organic layer was dried over anhydrous magnesium sulfate, and the solvent was removed under a vacuum. Acetonitrile (19.4 mL) and triphenylphosphonium bromide (796 mg) was added to the residue, and the resultant was heated under reflux for 2 hours. The resultant was returned to room temperature, and 3-methoxy-4-(4-methyl-1H-imidazol-1-yl) benzaldehyde (543 mg) and triethylamine (633 µL) were added, and stirring was continued for 12 hours at room temperature. The solvent was removed under a vacuum, and ethyl acetate and brine were added, and the organic layer was partitioned. The organic layer was dried over anhydrous magnesium sulfate, and the solvent was removed under vacuum, and the residue was purified by silica gel column chromatography (carrier: Chromatrex NH, eluting solvent: hexane/ethyl acetate→ethyl acetate), and the title compound (640 mg) was obtained. The physical property values are as follows.

ESI-MS; m/z 480 [M$^+$+H]. $^1$H-NMR (CDCl$_3$) δ (ppm): 1.48 (d, J=6.4 Hz, 3H), 2.29 (s, 3H), 3.51 (dd, J=11.2, 11.2 Hz, 1H), 3.74 (dd, J=12.0, 8.0 Hz, 1H), 3.83 (s, 3H), 3.99 (dd, J=11.2, 4.0 Hz, 1H), 4.18 (dd, J=12.4, 4.8 Hz, 1H), 4.41 (ddd, J=11.6, 4.0, 4.0 Hz, 1H), 4.50-4.56 (m, 1H), 4, 86 (dd, J=8.0, 4.4 Hz, 1H), 7.82 (s, 1H), 6.91 (s, 1H), 7.18 (d, J=8.8 Hz, 1H), 7.32-7.35 (m, 6H), 7.69 (s, 1H).

EXAMPLE 6 AND EXAMPLE 7

Synthesis of (Z)-(1S,6S,8aR)-6-(4-fluorophenyl)-3-[3-methoxy]-4-(4-methylimidazol-1-yl)ben-zylidene]-1-methyltetrahydropyrrolo[2,1-c][1,4]oxazin-4-one and synthesis of (Z)-(1R,6S,8aR)-6-(4-fluorophenyl)-3-[3-methoxy-4-(4-methylimidazol-1-yl)benzylidene]-1-methyltetrahydropyrrolo[2,1-c][1,4]oxazin-4-one

[Formula 13]

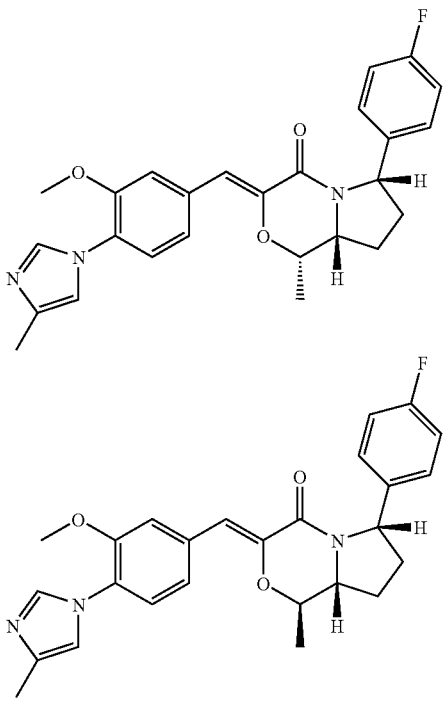

Synthesis of (2S,5R)-2-(4-fluorophenyl)-5-hydroxymethyl-pyrrolidine-1-carboxylic acid t-butyl ester Ice-cold lithium borohydride (256 mg) was added to a tetrahydrofuran (30 mL) solution of (2R,5S)-5-(4-fluorophenyl)pyrrolidine-1,2-dicarboxylic acid 1-t-butyl ester 2-ethyl ester (2.64 g) obtained in Example 4. Stirring was continued for 30 minutes at the same temperature and for 14 hours at room temperature. Water and ethyl acetate were added, and the organic layer was partitioned. The organic layer was washed with brine, and the resultant was dried over anhy-drous magnesium sulfate. The solvent was removed under a vacuum, and the title compound (2.31 g) was obtained. The physical property values are as follows.

ESI-MS; m/z 318 [M$^+$+Na]. $^1$H-NMR (CDCl$_3$) δ (ppm): 1.21 (s, 9H), 1.56-1.70 (m, 1H), 1.78-1.87 (m, 1H), 1.98-2.07 (m, 1H), 2.22-2.30 (m, 1H), 3.77-3.80 (m, 2H), 4.12-4.20 (m, 1H), 4.80 (dd, J=6.8, 6.8 Hz, 1H), 6.97-7.02 (m, 2H), 7.17-7.21 (m, 2H).

Synthesis of (2S,5R)-2-(4-fluorophenyl)-5-((R)-1-hydroxyethyl)-pyrrolidine-1-carboxylic acid t-butyl ester and (2S,5R)-2-(4-fluorophenyl)-5-((S)-1-hy-droxyethyl)-pyrrolidine-1-carboxylic acid t-butyl ester A dichloromethane (25 mL) solution containing oxalyl chloride (752 μL) was cooled to –78° C., and dimethyl sul-foxide (670 μL, dichloromethane 1 mL solution) was added dropwise. After stirring for 5 minutes at the same tempera-ture, a dichloromethane (4 mL) solution of (2S,5R)-2-(4-fluorophenyl)-5-hydroxymethyl-pyrrolidine-1-carboxylic acid t-butyl ester (1.86 g) was added dropwise. After stirring for 30 minutes at the same temperature, triethylamine (3.48 mL) was added, and stirring was continued for 30 minutes from –78° C. to room temperature. Ammonium chloride aqueous solution was added to the reaction solution, and the organic layer was partitioned. The organic layer was washed with brine and dried over anhydrous magnesium sulfate. The solvent was removed under a vacuum, and tetrahydrofuran (40 mL) was added to the residue, and the resultant was cooled to –78° C. Methyl magnesium bromide (8.43 mL, 0.97 M tetrahydrofuran solution) was added dropwise into the reaction solution, and stirring was continued for 1 hour at the same temperature. Ammonium chloride aqueous solution and ethyl acetate were added to the reaction solution, and the organic layer was partitioned. The organic layer was washed with brine, and the resultant was dried with magnesium sul-fate, and the solvent was removed under a vacuum. The resi-due was purified by silica gel column chromatography (hep-tane/ethyl acetate). The low polarity title compound (920 mg) and the high polarity title compound (560 mg) were obtained. The physical property values are as follows.
Low Polarity Title Compound
$^1$H-NMR (CDCl$_3$) δ (ppm): 1.21 (s, 9H), 1.23 (d, J=6.4 Hz, 3H), 1.64-1.71 (m, 1H), 1.78-1.87 (m, 1H), 1.96-2.05 (m, 1H), 2.21-2.28 (m, 1H), 3.77-3.84 (m, 1H), 3.85-3.91 (m, 1H), 4.79 (dd, J=7.2, 7.2 Hz, 1H), 5.12 (brs, 1H), 6.96-7.02 (m, 2H), 7.22-7.26 (m, 2H).
High Polarity Title Compound
$^1$H-NMR (CDCl$_3$) δ (ppm): 1.22 (d, J=6.4 Hz, 3H), 1.27 (s, 9H), 1.88-1.99 (m, 3H), 2.16-2.26 (m, 1H), 3.92-4.0 (brm, 1H), 4.08-4.16 (m, 1H), 4.74-4.82 (m, 1H), 6.95-7.01 (m, 2H), 7.26-7.30 (m, 2H).

Synthesis of (S)-1-[(2R,5S)-5-(4-fluorophenyl)pyrro-lidine-2-yl]ethanol

A 4 N hydrochloric acid/ethyl acetate (6.8 mL) solution of (2S,5R)-2-(4-fluorophenyl)-5-((S)-1-hydroxyethyl)-pyrroli-dine-1-carboxylic acid t-butyl ester (708 mg, high polarity compound) was stirred for 1 hour at room temperature. The solvent was removed under a vacuum, and 5 N sodium hydroxide was added, and extraction was conducted twice with dichloromethane. The organic layer was dried over anhydrous magnesium sulfate, and the solvent was removed under a vacuum, and the title compound (479 mg) was obtained. The physical property values are as follows.
ESI-MS; m/z 210 [M$^+$+H].

Synthesis of (1S,6S,8aR)-6-(4-fluorophenyl)-1-methyltetrahyropyrrolo[2,1-c][1,4]oxazine-3,4-dione Under ice-cooling, oxalyl chloride (392 μL) was added dropwise into a dichloromethane (4 mL) solution containing (S)-1-[(2R,5S)-5-(4-fluorophenyl)pyrrolidine-2-yl]ethanol (479 mg) and pyridine (1 mL). Stirring was continued for 1 hour at the same temperature and for 1 hour at room temperature. Water was added, and the organic layer was partitioned, and the resultant was dried over anhydrous magnesium sulfate. The solvent was removed under a vacuum, and the residue was purified by silica gel column chromatography (heptane/ethyl acetate→ethyl acetate), and the title compound (130 mg) was obtained. The physical property values are as follows.

$^1$H-NMR (CDCl$_3$) δ (ppm): 1.51 (d, J=6.8 Hz, 3H), 1.89-2.00 (m, 1H), 2.15-2.25 (m, 2H), 2.41-2.52 (m, 1H), 4.38-4.44 (m, 1H), 4.85-4.91 (m, 1H), 5.17 (d, J=9.2 Hz, 1H), 7.00-7.05 (m, 2H), 7.25-7.33 (m, 2H).

Synthesis of (Z)-(1S,6S,8aR)-6-(4-fluorophenyl)-3-[3-methoxy-4-(4-methylimidazol-1-yl)benzylidene]-1-methyltetrahydropyrrolo[2,1-c][1,4]oxazin-4-one Under ice-cooling, L-selectride (0.57 mL, 1.02 M tetrahydrofuran solution) was added dropwise into a tetrahydrofuran (5 mL) solution containing (1S,6S,8aR)-6-(4-fluorophenyl)-1-methyltetrahyropyrrolo[2,1-c][1,4]oxazine-3,4-dione (130 mg). Stirring was continued for 1 hour at the same temperature. A 5 N sodium hydroxide solution (86.7 μL) was added to the reaction solution, and stirring was continued for 20 minutes at 0° C. Next, hydrogen peroxide solution (42 μL, 35% solution) was added, and stirring was continued for 20 minutes at 0° C. Sodium bisulfite (45 mg) was added, and after stirring for 20 minutes at room temperature, ethyl acetate and brine were added, and organic layer was partitioned. The organic layer was dried over anhydrous magnesium sulfate, and the solvent was removed under a vacuum. Acetonitrile (5 mL) and triphenyl phosphonium bromide (151 mg) were added to the residue, and heating under reflux was conducted for 1 hour. The resultant was returned to room temperature, and 3-methoxy-4-(4-methyl-1H-imidazol-1-yl)benzaldehyde (103 mg) and triethylamine (120 μL) were added, and stirring was continued for 10 hours at room temperature. The solvent was removed under a vacuum, and ethyl acetate and brine were added, and the organic layer was partitioned. The resultant was dried over anhydrous magnesium sulfate, and the solvent was removed under a vacuum. The residue was purified by a silica gel column chromatography (carrier: Chromatrex NH, eluting solvent: hexane/ethyl acetate→ethyl acetate→ethyl acetate/methanol), and the title compound (106 mg) was obtained. The physical property values are as follows.

ESI-MS; m/z 448 [M$^+$+H]. $^1$H-NMR (CDCl$_3$) δ (ppm): 1.46 (d, J=6.8 Hz, 3H), 1.82-1.94 (m, 1H), 2.04-2.15 (m, 2H), 2.29 (s, 3H), 2.34-2.45 (m, 1H), 3.84 (s, 3H), 4.22-4.28 (m, 1H), 4.77-4.83 (m, 1H), 5.16 (d, J=9.2 Hz, 1H), 6.80 (s, 1H), 6.91 (dd, J=1.6, 0.8 Hz, 1H), 6.98-7.04 (m, 2H), 7.18 (d, J=8.8 Hz, 1H), 7.28-7.31 (m, 2H), 7.38 (s, 1H), 7.38-7.40 (m, 1H), 7.69 (d, J=1.2 Hz, 1H).

Synthesis of (Z)-(1R,6S,8aR)-6-(4-fluorophenyl)-3-[3-methoxy-4-(4-methylimidazol-1-yl)benzylidene]-1-methyltetrahydropyrrolo[2,1-c][1,4]oxazin-4-one In the same manner as in Example 6, the title compound (250 mg) was obtained from (2S,5R)-2-(4-fluorophenyl)-5-((R)-1-hydroxyethyl)-pyrrolidine-1-carboxylic acid t-butyl ester (1.04 g, low polarity compound). The physical property values are as follows.

ESI-MS; m/z 448 [M$^+$+H]. $^1$H-NMR (CDCl$_3$) δ (ppm): 1.56 (d, J=6.4 Hz, 3H), 1.73-1.84 (m, 1H), 1.92-1.97 (m, 1H), 2.04-2.10 (m, 1H), 2.29 (s, 3H), 2.33-2.42 (m, 1H), 3.72-3.79 (m, 1H), 3.85 (s, 3H), 4.23-4.31 (m, 1H), 5.24 (d, J=8.8 Hz, 1H), 6.71 (s, 1H), 6.92 (dd, J=0.8, 0.8 Hz, 1H), 6.98-7.02 (m, 2H), 7.13-7.18 (m, 3H), 7.32 (dd, J=8.0, 1.6 Hz, 1H), 7.54 (d, J=1.6 Hz, 1H), 7.70 (d, J=0.8 Hz, 1H).

EXAMPLE 8

Synthesis of (Z)-(6S,8aR)-6-(4-chlorophenyl)-3-[3-methoxy-4-(4-methylimidazol-1-yl)benzylidene]-1,1-dimethyltetrahydropyrrolo[2,1-c][1,4]oxazine-4-one

[Formula 14]

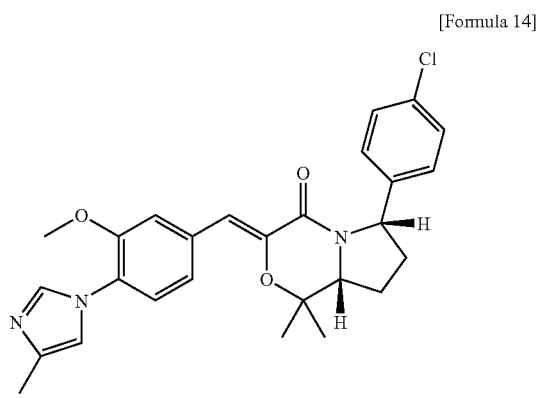

Synthesis of (R)-2-t-butoxycarbonylamino-5-(4-chlorophenyl)-5-oxovaleric acid ethyl ester Under a nitrogen atmosphere, 4-chlorophenyl magnesium bromide (64.1 mL, 1 M tetrahydrofuran solution) was added dropwise at −40° C. into a tetrahydrofuran (300 mL) solution of (R)-5-oxopyrrolidine-1,2-dicarboxylic acid 1-t-butyl ester 2-ethyl ester (15 g) obtained in Example 4. After stirring for 1 hour at the same temperature, saturated ammonium chloride aqueous solution was added, and extraction with ethyl acetate was conducted. After washing the organic layer with brine, the resultant was dried over anhydrous magnesium sulfate. The solvent was removed under a vacuum, and the residue was purified by silica gel column chromatography (heptane→heptane/ethyl acetate), and the title compound (17.38 g) was obtained. The physical property values are as follows.

ESI-MS; m/z 392 [M$^+$+Na].

Synthesis of (2R,5S)-5-(4-chlorophenyl)pyrrolidine-2-carboxylic acid ethyl ester A 4 N hydrochloric acid/ethyl acetate solution (120 mL) was added to (R)-2-t-butoxycarbonylamino-5-(4-chlorophenyl)-5-oxovaleric acid ethyl ester (17.4 g). Stirring was continued for 3 hours at room temperature. The solvent was removed under a vacuum, and ethyl acetate and saturated sodium bicarbonate solution was added, and the organic layer was partitioned. The organic layer was washed with brine and was dried with magnesium sulfate. The solvent was removed under a vacuum, and methanol (200 mL) and acetic acid (50 mL) were added to the residue. The reaction solution was cooled to −50° C., and sodium borohydride (1.07 g) was added over 20 minutes. After stirring for 4 hours at −50° C. to room temperature, the resultant was stirred overnight at room temperature. Disodium hydrogenphosphate solution was added to the reaction solution, and the solvent was removed under a vacuum, Water and ethyl acetate were added, and the organic layer was partitioned. Saturated sodium bicarbonate solution was added to the organic layer, and stirring was continued for 1 hour at room temperature, and the organic layer was partitioned. The organic layer was washed with brine and was dried over anhydrous magnesium sulfate. The solvent was removed under a vacuum, and the residue was purified by silica gel column chromatography (heptane/ethyl acetate), and the title compound (4.71 g) was obtained.

ESI-MS; m/z 254 [M$^+$+H]. $^1$H-NMR (CDCl$_3$) δ (ppm): 1.30 (t, J=7.2 Hz, 3H), 1.62-1.69 (m, 1H), 2.07-2.24 (m, 3H), 3.90 (dd, J=8.4, 4.8 Hz, 1H), 4.18 (dd, J=8.4, 6.4 Hz, 1H), 4.22 (q, J=7.2 Hz, 2H), 7.27-7.30 (m, 2H), 7.36-7.39 (m, 2H).

Synthesis of (2R,5S)-5-(4-chlorophenyl)pyrrolidine-1,2-dicarboxylic acid 1-t-butyl ester 2-ethyl ester A dimethyl formamide (50 mL) solution containing (2R,5S)-5-(4-chlorophenyl)pyrrolidine-2-carboxylic acid ethyl ester (4.71 g), triethylamine (4.13 mL) and di-t-butyl dicarbonate (5.28 g) was stirred for 14 hours at room temperature. Imidazole was added to the reaction mixture, and stirring was continued for 20 minutes at room temperature. Ethyl acetate was added to the reaction solution, and the resultant was washed with 0.2 N hydrochloric acid (twice) and brine in sequence, and the organic layer was dried over anhydrous magnesium sulfate. The solvent was removed under a vacuum, and the title compound (6.58 g) was obtained. The physical property values are as follows.

$^1$H-NMR (CDCl$_3$) δ (ppm): 1.17 (s, 4.5H), 1.32 (t, J=6.8 Hz, 1.5H), 1.34 (t, J=7.2 Hz, 1.5H), 1.41 (s, 4.5H), 1.84-1.96 (m, 1H), 1.96-2.07 (m, 1H), 2.18-2.35 (m, 2H), 4.25 (q, J=7.2 Hz, 2H), 4.33 (dd, J=8.0, 8.0 Hz, 0.5H), 4.46 (dd, J=8.4, 4.0 Hz, 0.5H), 4.72 (dd, J=6.8, 6.8 Hz, 0.5H), 4.82-4.95 (m, 0.5H), 7.28 (d, J=8.4 Hz, 2H), 7.50-7.54 (brm, 2H).

Synthesis of 2-[(2R,5S)-5-(4-chlorophenyl)pyridin-2-yl]propan-2-ol

Under a nitrogen atmosphere and under ice-cooling, methyl magnesium bromide (21.2 mL, 0.97 M tetrahydrofuran solution) was added dropwise into a tetrahydrofuran (30.5 mL) solution containing (2R,5S)-5-(4-chlorophenyl)pyrrolidine-1,2-dicarboxylic acid 1-t-butyl ester 2-ethyl ester (2 g). After stirring for 2 hours at the same temperature, ammonium chloride aqueous solution and ethyl acetate were added, and the organic layer was partitioned. The organic layer was washed with brine and was dried over anhydrous magnesium sulfate, and the solvent was removed under a vacuum. The residue was dissolved in ethyl acetate (7 mL), and 4 N hydrochloric acid/ethyl acetate (14.7 mL) was added, and stirring was continued for 1 hour. The solvent was removed under a vacuum, and ethyl acetate and saturated sodium bicarbonate solution were added, and the organic layer was partitioned. The organic layer was washed with brine and dried over anhydrous magnesium sulfate, and the solvent was removed under a vacuum, and the title compound (1.36 g) was obtained. The physical property values are as follows.

ESI-MS; m/z 240 [M$^+$+H]. $^1$H-NMR (CDCl$_3$) δ (ppm): 1.19 (s, 3H), 1.20 (s, 3H), 1.76-1.94 (m, 3H), 2.07-2.19 (m, 1H), 3.19 (dd, J=8.8, 8.8 Hz, 1H), 4.22 (dd, J=8.4, 7.2 Hz, 1H), 7.25-7.28 (m, 2H), 7.31-7.34 (m, 2H).

Synthesis of (4R,6S)-6-(4-chlorophenyl)-1,1-dimethyltetrahydropyrrolo[2,1-c][1,4]oxazine-3,4-dione Under ice-cooling, oxalyl chloride (585 μL) was added dropwise into a dichloromethane (20 mL) solution containing 2-[(2R,5S)-5-(4-chlorophenyl)pyridin-2-yl]propan-2-ol (1.36 g) and pyridine (5 mL). Stirring was continued for 30 minutes at the same temperature. Water and ethyl acetate were added, and the organic layer was partitioned. After washing the organic layer with brine, the resultant was dried over anhydrous magnesium sulfate. The solvent was removed under a vacuum, and the residue was purified by silica gel column chromatography (heptane/ethyl acetate), and the title compound (857 mg) was obtained. The physical property values are as follows.

ESI-MS; m/z 294 [M$^+$+H]. $^1$H-NMR (CDCl$_3$) δ (ppm): 1.50 (s, 3H), 1.53 (s, 3H), 1.87-1.98 (m, 1H), 2.14-2.23 (m, 2H), 2.39-2.50 (m, 1H), 4.10 (dd, J=11.2, 5.6 Hz, 1H), 5.16 (d, J=9.2 Hz, 1H), 7.25-7.32 (m, 4H).

Synthesis of (Z)-(6S,8aR)-6-(4-chlorophenyl)-3-[3-methoxy-4-(4-methylimidazol-1-yl)benzylidene]-1,1-dimethyltetrahydropyrrolo[2,1-c][1,4]oxazin-4-one Under ice-cooling, L-selectride (3.73 mL, 1.02 M tetrahydrofuran solution) was added dropwise into a tetrahydrofuran (25 mL) solution containing (4R,6S)-6-(4-chlorophenyl)-1,1-dimethyltetrahydropyrrolo[2,1-c][1,4]oxazine-3,4-dione (850 mg). Stirring was continued for 1 hour at the same temperature. A 5 N sodium hydroxide solution (566 μL) was added to the reaction solution, and stirring was continued for 20 minutes at 0° C. Next, hydrogen peroxide solution (275 μL, 35% solution) was added, and stirring was continued for 20 minutes at 0° C. Sodium bisulfite (294 mg) was added, and after stirring for 20 minutes at room temperature, ethyl acetate and brine were added, and the organic layer was partitioned. The organic layer was dried over anhydrous magnesium sulfate, and the solvent was removed under a vacuum. Acetonitrile (25 mL) and triphenyl phosphonium bromide (990 mg) was added to the residue, and the resultant was heated under reflux for 1 hour. The resultant was returned to room temperature, and 3-methoxy-4-(4-methyl-1H-imidazol-1-yl) benzaldehyde (674 mg) and triethylamine (781 μL) were added, and stirring was continued for 10 hours at room temperature. Ethyl acetate and brine were added, and the organic layer was partitioned. The resultant was dried over anhydrous magnesium sulfate, and the solvent was removed under a vacuum, and ethyl acetate (1 mL) was added to the residue, and diethyl ether (15 mL) was added gradually, and the precipitated solid was collected by filtration, and the title compound (790 mg) was obtained. The physical property values are as follows.

ESI-MS; m/z 478 [M$^+$+H]. $^1$H-NMR (CDCl$_3$) δ (ppm): 1.45 (s, 3H), 1.58 (s, 3H), 1.81-1.92 (m, 1H), 2.02-2.14 (m, 2H), 2.29 (s, 3H), 2.34-2.45 (m, 1H), 3.85 (s, 3H), 3.94 (dd, J=11.6, 5.2 Hz, 1H), 5.14 (d, J=9.2 Hz, 1H), 6.78 (s, 1H), 6.91

(s, 1H), 7.18 (d, J=8.0 Hz, 1H), 7.24-7.32 (m, 5H), 0.53 (d, J=9.6 Hz, 1H), 7.69 (d, J=1.6 Hz, 1H).

EXAMPLE 9 AND EXAMPLE 10

Synthesis of (Z)-(1S,6S,8aR)-6-(4-chlorophenyl)-3-[3-methoxy-4-(4-methylimidazol-1-yl)benzylidene]-1-methyltetrahydropyrrolo[2,1-c][1,4]oxazin-4-one and (Z)-(1R,6S,8aR)-6-(4-chlorophenyl)-3-[3-methoxy-4-(4-methylimidazol-1-yl)benzylidene]-1-methyltetrahydropyrrolo[2,1-c][1,4]oxazin-4-one

[Formula 15]

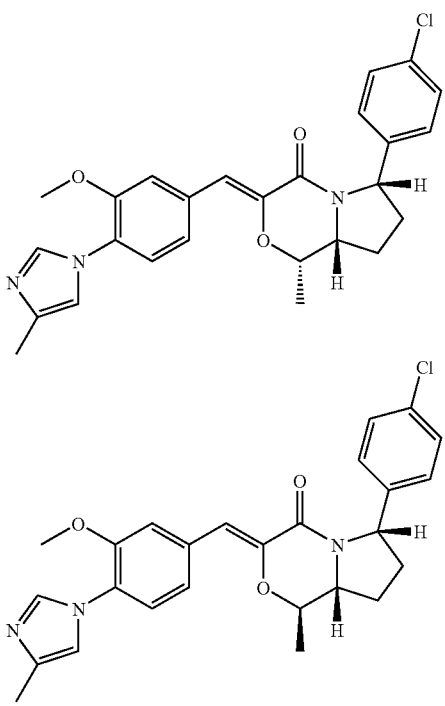

Synthesis of (2S,5R)-2-(4-chlorophenyl)-5-hydroxymethyl-pyrrolidine-1-carboxylic acid t-butyl ester Ice-cold lithium borohydride (277 mg) was added to a tetrahydrofuran (40 mL) solution of (2R,5S)-5-(4-chlorophenyl)pyrrolidine-1,2-dicarboxylic acid 1-t-butyl ester 2-ethyl ester (3 g) obtained in Example 8. Stirring was continued for 30 minutes at the same temperature and for 13 hours at room temperature. Water and ethyl acetate were added, and the organic layer was partitioned. The organic layer was washed with brine and was dried over anhydrous magnesium sulfate. The solvent was removed under a vacuum, and the title compound (2.64 g) was obtained. The physical property values are as follows.

ESI-MS; m/z 318 [M$^+$+Na]. $^1$H-NMR (CDCl$_3$) δ (ppm): 1.21 (s, 9H), 1.56-1.64 (m, 1H), 1.77-1.85 (m, 1H), 1.98-2.07 (m, 1H), 2.22-2.31 (m, 1H), 3.78 (dd, J=6.4, 4.4 Hz, 2H), 4.11-4.20 (m, 1H), 4.80 (dd, J=6.4, 6.4 Hz, 1H), 7.17 (d, J=8.4 Hz, 2H), 7.25-7.29 (m, 2H).

Synthesis of (2S,5R)-2-(4-chlorophenyl)-5-((R)-1-hydroxyethyl)-pyrrolidine-1-carboxylic acid t-butyl ester and (2S,5R)-2-(4-chlorophenyl)-5-((S)-1-hydroxyethyl)-pyrrolidine-1-carboxylic acid t-butyl ester A dichloromethane (45 mL) solution containing oxalyl chloride (1.07 mL) was cooled to −78° C., and dimethyl sulfoxide (951 μL, dichloromethane 1 mL solution) was added dropwise. After stirring for 5 minutes at the same temperature, a dichloromethane (4 mL) solution of (2S,5R)-2-(4-chlorophenyl)-5-hydroxymethyl-pyrrolidine-1-carboxylic acid t-butyl ester (2.64 g) was added dropwise. After stirring for 30 minutes at the same temperature, triethylamine (4.94 mL) was added, and stirring was continued for 30 minutes from −78° C. to room temperature. Ammonium chloride aqueous solution was added to the reaction solution, and the organic layer was partitioned. The organic layer was washed with brine and dried over anhydrous magnesium sulfate. The solvent was removed under a vacuum, and tetrahydrofuran (55 mL) was added to the residue, and the resultant was cooled to −78° C. Methyl magnesium bromide (12 mL, 0.97 M tetrahydrofuran solution) was added dropwise into the reaction solution, and stirring was continued for 1 hour at the same temperature. Ammonium chloride aqueous solution and ethyl acetate were added to the reaction solution, and the organic layer was partitioned. The organic layer was washed with brine and dried with magnesium sulfate, and the solvent was removed under a vacuum. The residue was purified by silica gel column chromatography (carrier: Chromatrex amino, heptane/ethyl acetate), and a low polarity title compound (550 mg) and a high polarity title compound (850 mg) were obtained. Their physical property values are as follows.

Low Polarity Title Compound $^1$H-NMR (CDCl$_3$) δ (ppm): 1.22 (d, J=6.8 Hz, 3H), 1.22 (s, 9H), 1.62-1.71 (m, 1H), 1.77-1.86 (m, 1H), 1.97-2.06 (m, 1H), 2.21-2.30 (m, 1H), 3.75-3.82 (m, 1H), 3.86-3.91 (m, 1H), 4.78 (dd, J=7.6, 7.6 Hz, 1H), 5.11 (m, 1H), 7.21-7.29 (m, 4H).

High Polarity Title Compound $^1$H-NMR (CDCl$_3$) δ (ppm): 1.23 (d, J=6.4 Hz, 3H), 1.27 (s, 9H), 1.90-2.00 (m, 3H), 2.18-2.28 (m, 1H), 3.92-4.00 (m, 1H), 4.11-4.96 (m, 1H), 4.73-4.81 (m, 1H), 7.25-7.26 (m, 4H).

Synthesis of (S)-1-[(2R,5S)-5-(4-chlorophenyl)pyrrolidine-2-yl]ethanol

4 N hydrochloric acid/ethyl acetate (7.5 mL) was added to an ethyl acetate (7.5 mL) solution of (2S,5R)-2-(4-fluorophenyl)-5-((S)-1-hydroxyethyl)-pyrrolidine-1-carboxylic acid t-butyl ester (850 mg, high polarity compound). Stirring was continued for 3 hours at room temperature. The solvent was removed under a vacuum, and sodium bicarbonate aqueous solution was added, and the resultant was extracted with chloroform. The organic layer was dried over anhydrous magnesium sulfate, and the solvent was removed under a vacuum, and the title compound (580 mg) was obtained. The physical property values are as follows.

ESI-MS; m/z 226 [M$^+$+H]. $^1$H-NMR (CDCl$_3$) δ (ppm): 1.18 (d, J=6.4 Hz, 1H), 1.51-1.61 (m, 1H), 1.71-1.80 (m, 1H), 1.85-1.93 (m, 1H), 2.04-2.16 (m, 1H), 3.26-3.31 (m, 1H), 3.79-3.84 (m, 1H), 4.19 (dd, J=9.2, 3.2 Hz, 1H), 7.25-7.32 (m, 4H).

Synthesis of (1S,6S,8aR)-6-(4-chlorophenyl)-1-methyltetrahydropyrrolo[2,1-c][1,4]oxazine-3,4-dione Diethyl oxalate (5 mL) was added to (S)-1-[(2R,5S)-5-(4-chlorophenyl)pyrrolidine-2-yl]ethanol (570 mg). Stirring was continued for 2 hours at 120° C. The solvent was removed under a vacuum, and the residue was purified by silica gel column chromatography (heptane/ethyl acetate→ethyl acetate), and the title compound (470 mg) was obtained. The physical property values are as follows.

ESI-MS; m/z 280 [M$^+$+H]. $^1$H-NMR (CDCl$_3$) δ (ppm): 1.51 (d, J=7.2 Hz, 3H), 1.88-1.98 (m, 1H), 2.15-2.24 (m, 2H), 2.42-2.53 (m, 1H), 4.39-4.44 (m, 1H), 4.86-4.92 (m, 1H), 5.16 (d, J=9.6 Hz, 1H), 7.25-7.33 (m, 4H).

Synthesis of (Z)-(1S,6S,8aR)-6-(4-chlorophenyl)-3-[3-methoxy-4-(4-methylimidazol-1-yl)benzylidene]-1-methyltetrahydropyrrolo[2,1-c][1,4]oxazin-4-one Under ice-cooling, L-selectride (2.06 mL, 1.02 M tetrahydrofuran solution) was added dropwise into a tetrahydrofuran (15 mL) solution containing (1S,6S,8aR)-6-(4-chlorophenyl)-1-methyltetrahydropyrrolo[2,1-c][1,4]oxazine-3,4-dione (470 mg). Stirring was continued for 1 hour at the same temperature. A 5 N sodium hydroxide solution (313 μl) was added to the reaction solution, and stirring was continued for 20 minutes at 0° C., and next a hydrogen peroxide solution (152 μL, 35% solution) was added, and stirring was continued for 20 minutes at 0° C. Sodium bisulfite (163 mg) was added, and after stirring for 20 minutes at room temperature, ethyl acetate and brine were added, and the organic layer was partitioned. The organic layer was dried over anhydrous magnesium sulfate, and the solvent was removed under a vacuum. Acetonitrile (15 mL) and triphenyl phosphonium bromide (547 mg) were added to the residue, and the resultant was heated under reflux for 1 hour. The resultant was returned to room temperature, and 3-methoxy-4-(4-methyl-1H-imidazol-1-yl) benzaldehyde (373 mg) and triethylamine (434 μL) were added, and stirring was continued for 10 hours at room temperature. Ethyl acetate and brine were added to the reaction solution, and the organic layer was partitioned. The resultant was dried over anhydrous magnesium sulfate, and the solvent was removed under a vacuum, and the residue was passed through a silica gel pad (carrier: Chromatrex NH, eluting solvent: ethyl acetate), and the solvent was removed under a vacuum. The resulting solid was suspended in dichloromethane (1 mL), and diethyl ether (5 mL) was added, and the solid was collected by filtration, and the title compound (220 mg) was obtained. The physical property values are as follows.

ESI-MS; m/z 464 [M$^+$+H]. $^1$H-NMR (CDCl$_3$) δ (ppm): 1.47 (d, J=6.8 Hz, 3H), 1.81-1.90 (m, 1H), 2.03-2.16 (m, 2H), 2.29 (s, 3H), 2.35-2.46 (m, 1H), 3.84 (s, 3H), 4.23-4.28 (m, 1H), 4.77-4.83 (m, 1H), 5.14 (d, J=9.2 Hz, 1H), 6.80 (s, 1H), 6.91 (s, 1H), 7.18 (d, J=8.8 Hz, 1H), 7.25-7.32 (m, 4H), 7.38 (s, 1H), 7.38-7.41 (m, 1H), 7.69 (d, J=1.2 Hz, 1H).

Synthesis of (Z)-(1R,6S,8aR)-6-(4-chlorophenyl)-3-[3-methoxy-4-(4-methylimidazol-1-yl)benzylidene]-1-methyltetrahydropyrrolo[2,1-c][1,4]oxazin-4-one In the same manner as in Example 9, the title compound (93 mg) was obtained from (2S,5R)-2-(4-chlorophenyl)-5-((R)-1-hydroxyethyl)-pyrrolidine-1-carboxylic acid t-butyl ester (550 mg, low polarity compound). The physical property values are as follows.

ESI-MS; m/z 464 [M$^+$+H]. $^1$H-NMR (CDCl$_3$) δ (ppm): 1.57 (d, J=6.4 Hz, 3H), 1.73-1.81 (m, 1H), 1.94 (dd, J=12.8, 6.4 Hz, 1H), 2.04-2.11 (m, 1H), 2.30 (s, 3H), 2.34-2.45 (m, 1H), 3.73-3.80 (m, 1H), 3.86 (s, 3H), 4.24-4.31 (m, 1H), 5.23 (d, J=8.8 Hz, 1H), 6.73 (s, 1H), 6.93 (s, 1H), 7.13 (d, J=8.4 z, 2H), 7.20 (d, J=8.0 Hz, 1H), 7.30 (d, J=8.4 Hz, 2H), 7.33 (dd, J=8.0, 1.2 Hz, 1H), 7.55 (d, J=1.2 Hz, 1H), 7.72 (d, J=0.8 Hz, 1H).

EXAMPLE 11

Synthesis of (Z)-(6S,8aR)-3-[3-methoxy-4-(4-methylimidazol-1-1)benzylidene]-1,1-dimethyl-6-(3,4,5-trifluorophenyl)tetrahydropyrrolo[2,1-c][1,4]oxazine-4 one

[Formula 16]

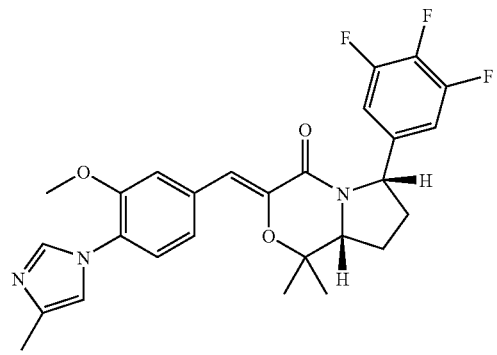

Synthesis of (R)-2-t-butoxycarbonylamino-5-oxo-5-(3,4,5-trifluorophenyl) valeric acid ethyl ester Preparation of 3,4,5-trifluorophenyl magnesium bromide: under a nitrogen atmosphere, 1-bromo-3,4,5-trifluorophenyl (2 mL) was added to a diethyl ether (60 mL) suspension of magnesium (1.7 g) and iodine (one fragment), and the resultant was heated. 1-bromo-3,4,5-trifluorophenyl (5.6 mL) was further added dropwise. After reflux was stopped, stirring was continued for 1 hour at room temperature.

Under a nitrogen atmosphere, the previously prepared 3,4,5-trifluorophenyl magnesium bromide was added dropwise at −40° C. into a tetrahydrofuran (200 mL) solution of (R)-5-oxopyrrolidine-1,2-dicarboxylic acid 1-t-butyl ester 2-ethyl ester (15 g) obtained in Example 4. After stirring for 1 hour at the same temperature, saturated ammonium chloride aqueous solution was added, and extraction with ethyl acetate was conducted. After washing the organic layer with brine, the resultant was dried over anhydrous magnesium sulfate. The solvent was removed under a vacuum, and the residue was passed through a silica pad (carrier: Chromatrex 400 cc, eluting solvent: ethyl acetate), and the title compound (22.34 g) was obtained. The physical property values are as follows.

ESI-MS; m/z 412 [M$^+$+Na].

Synthesis of (R)-5-(3,4,5-trifluorophenyl)-3,4-dihydro-2H-pyrrole-2-carboxylic acid ethyl ester 4 N hydrochloric acid/ethyl acetate (163 mL) was added to an ethyl acetate (30 mL) solution of (R)-2-t-butoxycarbonylamino-5-oxo-5-(3,4,5-trifluorophenyl) valeric acid ethyl ester (22.2 g), and stirring was continued for 3 hours at room temperature. The solvent was removed under a vacuum, and ethyl acetate and sodium bicarbonate aqueous solution were added to the residue, and the organic layer was partitioned. After washing the organic layer with brine, the resultant was dried over anhydrous magnesium sulfate. The solvent was removed under a vacuum, and the title compound (12.4 g) was obtained. The physical property values are as follows.

ESI-MS; m/z 272 [M⁺+H]. ¹H-NMR (CDCl₃) δ (ppm): 1.32 (t, J=7.2 Hz, 3H), 2.24-2.31 (m, 1H), 2.33-2.43 (m, 1H), 2.86-2.95 (m, 1H), 3.03-3.12 (m, 1H), 4.23 (q, J=7.2 Hz, 2H), 4.87-4.92 (m, 1H), 7.51 (dd, J=8.4, 6.4 Hz, 2H).

Synthesis of (2R,5S)-5-(3,4,5-trifluorophenyl)pyrrolidine-2-carboxylic acid ethyl ester 10% palladium on carbon (1.2 g, 50% water content) was added to an ethanol (170 mL) solution of (R)-5-(3,4,5-trifluorophenyl)-3,4-dihydro-2H-pyrrole-2-carboxylic acid ethyl ester (12.4 g). Under a hydrogen atmosphere, stirring was continued for 16 hours at room temperature. The catalyst was filtered on celite, and the filtrate was concentrated, and the title compound (11.98 g) was obtained. The physical property values are as follows.

¹H-NMR (CDCl₃) δ (ppm): 1.31 (t, J=7.2 Hz, 3H), 1.61-1.69 (m, 1H), 2.05-2.21 (m, 3H), 3.93 (dd, J=8.0, 5.6 Hz, 1H), 4.19 (dd, J=7.2, 7.2 Hz, 1H), 4.22 (q, J=7.2 Hz, 2H), 7.11 (dd, J=8.4, 6.4 Hz, 2H).

Synthesis of (2R,5S)-5-(3,4,5-trifluorophenyl)pyrrolidine-1,2-dicarboxylic acid 1-t-butyl ester 2-ethyl ester A dimethylformamide (120 mL) solution containing (2R,5S)-5-(3,4,5-trifluorophenyl)pyrrolidine-2-carboxylic acid ethyl ester (11.98 g), triethylamine (10.5 mL), and di-t-butyl dicarbonate (13.4 g) was stirred for 5 hours at room temperature. Imidazole (1.79 g) was added to the reaction mixture, and stirring was continued for 20 minutes at room temperature. Water and ethyl acetate were added, and the organic layer was partitioned, and the resultant was washed with 0.2 N hydrochloric acid (twice) and brine, in sequence. The organic layer was dried over anhydrous magnesium sulfate. The solvent was removed under a vacuum, and the residue was passed through a silica pad, and the title compound (16.4 g) was obtained. The physical property values are as follows.

ESI-MS; m/z 396 [M⁺+Na].

Synthesis of 2-[(2R,5S)-5-(3,4,5-trifluorophenyl)pyrrolidine-2-yl]propan-2-ol

Under a nitrogen atmosphere and under ice-cooling, methyl magnesium bromide (20.7 mL, 0.97M tetrahydrofuran solution) was added dropwise into a tetrahydrofuran (50 mL) solution of (2R,5S)-5-(3,4,5-trifluorophenyl)pyrrolidine-1,2-dicarboxylic acid 1-t-butyl ester 2-ethyl ester (2.5 g). After stirring for 2 hours at the same temperature, ammonium chloride aqueous solution and ethyl acetate were added, and the organic layer was partitioned. The organic layer was washed with brine and was dried with magnesium sulfate, and the solvent was removed under a vacuum. Ethyl acetate (7 mL) and 4 N hydrochloric acid/ethyl acetate (20 mL) were added to the residue, and stirring was continued for 1 hour at room temperature. The solvent was removed under a vacuum, and ethyl acetate and sodium bicarbonate aqueous solution were added, and the organic layer was partitioned. The organic layer was washed with brine and dried over anhydrous magnesium sulfate, and the solvent was removed under a vacuum, and the residue was purified by silica gel column chromatography (heptane/ethyl acetate→ethyl acetate), and the title compound (745 mg) was obtained. The physical property values are as follows.

ESI-MS; m/z 260 [M⁺+H]. ¹H-NMR (CDCl₃) δ (ppm): 1.19 (s, 3H), 1.21 (s, 3H), 1.49-1.58 (m, 1H), 1.76-1.89 (m, 2H), 2.04-2.16 (m, 1H), 3.19 (dd, J=8.4, 7.2 Hz, 1H), 4, 18 (dd, J=8.0, 8.0 Hz, 1H), 6.98-7.05 (m, 2H).

Synthesis of (6S,8aR)-1,1-dimethyl-6-(3,4,5-trifluorophenyl)tetrahydropyrrolo[2,1-c][1,4]oxazine-3,4-dione Under ice-cooling, oxalyl chloride (320 μL) was added dropwise into a dichloromethane (30 mL) solution containing 2-[(2R,5S)-5-(3,4,5-trifluorophenyl)pyrrolidine-2-yl]propan-2-ol (745 mg) and pyridine (5 mL). After stirring for 30 minutes at the same temperature, water was added to the reaction solution, and the organic layer was partitioned. After washing the organic layer with brine, the resultant was dried over anhydrous magnesium sulfate. The solvent was removed under a vacuum, and the residue was purified by silica gel column chromatography (heptane/ethyl acetate→ethyl acetate), and the title compound (580 mg) was obtained. The physical property values are as follows.

ESI-MS; m/z 314 [M⁺+H]. ¹H-NMR (CDCl₃) δ (ppm): 1.52 (s, 3H), 1.54 (s, 3H), 1.83-1, 95 (m, 1H), 2.14-2.22 (m, 2H), 2.41-2.52 (m, 1H), 4.11 (dd, J=11.6, 6.8 Hz, 1H), 5.08 (d, J=9.6 Hz, 1H), 6.97 (dd, J=8.4, 6.4 Hz, 2H).

Synthesis of (Z)-(6S,8aR)-3-[3-methoxy-4-(4-methylimidazol-1-yl)benzylidene]-1,1-dimethyl-6-(3,4,5-trifluorophenyl)tetrahydropyrrolo[2,1-c][1,4]oxazine-4 one Under ice-cooling, L-selectride (2.55 mL, 1.02 M tetrahydrofuran solution) was added dropwise into a tetrahydrofuran (20 mL) solution containing (6S,8aR)-1,1-dimethyl-6-(3,4,5-trifluorophenyl)tetrahydropyrrolo[2,1-c][1,4]oxazine-3,4-dione (580 mg), and stirring was continued for 1 hour at the same temperature. 5 N sodium hydroxide solution (386 was added to the reaction solution, and stirring was continued for 20 minutes at 0° C., and next, hydrogen peroxide solution (188 μL, 35% solution) was added, and stirring was continued for 20 minutes at 0° C. Sodium bisulfite (201 mg) was added, and after stirring for 20 minutes at room temperature, ethyl acetate and brine were added, and the organic layer was partitioned. The organic layer was dried over anhydrous magnesium sulfate, and the solvent was removed under a vacuum. Acetonitrile (20 mL) and triphenyl phosphonium bromide (676 mg) were added to the residue, and the resultant was heated under reflux for 1 hour. The resultant was returned to room temperature, and 3-methoxy-4-(4-methyl-1H-imidazol-1-yl)benzaldehyde (460 mg) and triethylamine (536 μL) were added, and stirring was continued for 60 hours at room temperature. Ethyl acetate and brine were added to the reaction solution, and the organic layer was partitioned. The organic layer was dried over anhydrous magnesium sulfate, and the solvent was removed under a vacuum, and the residue was purified by silica gel column chromatography (carrier: Chromatrex NH, eluting solvent: heptane/ethyl acetate→ethyl acetate), and the title compound (570 mg) was obtained. The physical property values are as follows.

ESI-MS; m/z 498 [M⁺+H]. ¹H-NMR (CDCl₃) δ (ppm): 1.47 (s, 3H), 1.58 (s, 3H), 1.77-1.88 (m, 1H), 1.99-2.04 (m, 1H), 2.09-2.15 (m, 1H), 2.29 (s, 3H), 2.34-2.45 (m, 1H), 3.85 (s, 3H), 3.93 (dd, J=11.6, 5.6 Hz, 1H), 5.06 (d, J=9.2 Hz, 1H), 6.78 (s, 1H), 6.92 (dd, J=0.8, 0.8 Hz, 1H), 6.94 (dd, J=8.4, 6.4

Hz, 2H), 7.19 (d, J=8.4 Hz, 1H), 7.32 (dd, J=8.4, 1.6 Hz, 1H), 7.52 (d, J=2.0 Hz, 1H), 7.70 (d, J=1.6 Hz, 1H).

EXAMPLE 12 AND 13

Synthesis of (Z)-(1S,6S,8aR)-3-[3-methoxy-4-(4-methylimidazol-1-yl)benzylidene]-1-methyl-6-(3,4,5-trifluorophenyl)tetrahydropyrrolo[2,1-c][1,4]oxazine-4 one and (Z)-(1R,6S,8aR)-3-[3-methoxy-4-(4-methylimidazol-1-yl)benzylidene]-1-methyl-6-(3,4,5-trifluorophenyl)tetrahydropyrrolo[2,1-c][1,4] oxazine-4 one

[Formula 17]

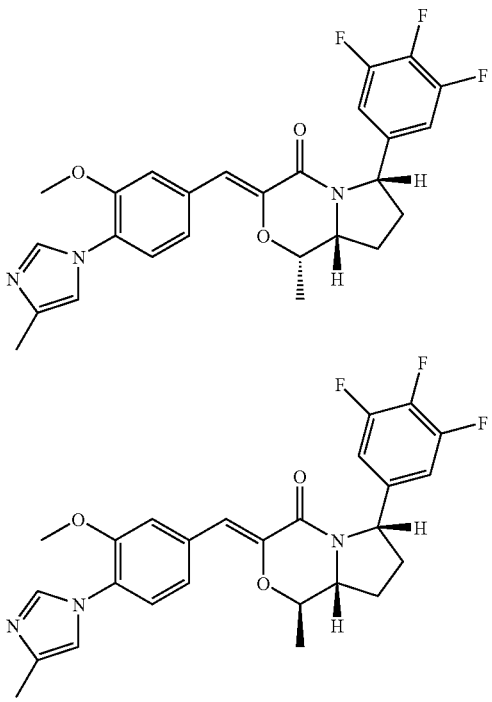

Synthesis of (S)-2-((R)-hydroxymethyl)-5-(3,4,5-trifluorophenyl)pyrrolidine-1-carboxylic acid t-butyl ester Under ice-cooling, lithium borohydride (554 mg) was added to a tetrahydrofuran solution of (2R,5S)-5-(3,4,5-trifluorophenyl)pyrrolidine-1,2-dicarboxylic acid 1-t-butyl ester 2-ethyl ester (6 g) obtained in Example 11. Stirring was continued for 30 minutes at the same temperature and for 13 hours at room temperature. Water and ethyl acetate were added to the reaction solution, and the organic layer was partitioned. The organic layer was washed with brine and dried over anhydrous magnesium sulfate. The solvent was removed under a vacuum, and the resultant was purified by silica gel column chromatography (heptane/ethyl acetate), and the title compound (4.65 g) was obtained. The physical property values are as follows.

ESI-MS; m/z 354 [M$^+$+Na]. $^1$H-NMR (CDCl$_3$) δ (ppm): 1.26 (s, 9H), 1.60-1.70 (m, 1H), 1.78-1.83 (m, 1H), 2.01-2.06 (m, 1H), 2.24-2.30 (m, 1H), 3.71-3.83 (m, 2H), 4.08-4.14 (m, 1H), 4.46 (brs, 1H), 4.75 (dd, J=6.8, 6.8 Hz, 1H), 6.88 (dd, J=8.0, 6.4 Hz, 2H).

Synthesis of (S)-2-((R)-1-hydroxyethyl)-5-(3,4,5-trifluorophenyl)pyrrolidine-1-carboxylic acid t-butyl ester A tetrahydrofuran (90 mL) solution containing dimethyl sulfoxide (1.68 mL) was cooled to −78° C., and oxalyl chloride (1.88 mL) was added dropwise. After stirring for 5 minutes at the same temperature, a tetrahydrofuran (10 mL) solution of (S)-2-((R)-hydroxymethyl)-5-(3,4,5-trifluorophenyl)pyrrolidine-1-carboxylic acid t-butyl ester (4.65 g) was added dropwise. After stirring for 40 minutes at the same temperature, triethylamine (8.7 mL) was added, and stirring was continued for 1 hour from −78° C. to room temperature. Ammonium chloride aqueous solution and ethyl acetate were added to the reaction solution, and the organic layer was partitioned. The organic layer was washed with brine and dried over anhydrous magnesium sulfate. The solvent was removed under a vacuum, and tetrahydrofuran (100 mL) was added to the residue, and the resultant was cooled to −78° C. Methyl magnesium bromide (17.3 mL, 0.97 M tetrahydrofuran solution) was added dropwise into the reaction solution, and stirring was continued for 1 hour at the same temperature. Ammonium chloride aqueous solution and ethyl acetate were added to the reaction solution, and the organic layer was partitioned. The organic layer was washed with brine and dried with magnesium sulfate, and the solvent was removed under a vacuum. The residue was purified by silica gel column chromatography (heptane/ethyl acetate), and the title compound (3.71 g) was obtained. The physical property values are as follows.

ESI-MS; m/z 368 [M$^+$+Na].

Synthesis of (R)-1-[(S)-5-(3,4,5-trifluorophenyl)pyrrolidine-2-yl]ethanol

4 N hydrochloric acid/ethyl acetate (26.8 mL) was added to an ethyl acetate (20 mL) solution of (S)-2-((R)-1-hydroxyethyl)-5-(3,4,5-trifluorophenyl)pyrrolidine-1-carboxylic acid t-butyl ester (3.71 g), and stirring was continued for 2 hours at room temperature. The solvent was removed under a vacuum, and 5 N sodium hydroxide solution and dichloromethane were added, and the organic layer was partitioned. The organic layer was dried over anhydrous magnesium sulfate, and the solvent was removed under a vacuum, and the title compound (2.6 g) was obtained. The physical property values are as follows.

ESI-MS; m/z 246 [M$^+$+H]

Synthesis of (1S,6S,8aR)-1-methyl-6-(3,4,5-trifluorophenyl)tetrahydropyrrolo[2,1-c][1,4]oxazine-3,4-dione and (1R,6S,8aR)-1-methyl-6-(3,4,5-trifluorophenyl)tetrahydropyrrolo[2,1-c][1,4]oxazine-3,4-dione Diethyl oxalate (14.3 mL) was added to (R)-1-[(S)-5-(3,4,5-trifluorophenyl)pyrrolidine-2-yl]ethanol (2.6 g), and stirring was continued for 4 hours at 120° C. The resultant was returned to room temperature, and the solvent was removed under a vacuum. The residue was purified by silica gel column chromatography (heptane/ethyl acetate→ethyl acetate), and the low polarity title compound (1.6 g) and the high polarity title compound (860 mg) was obtained. Their physical property values are as follows.

Low Polarity Title Compound $^1$H-NMR (CDCl$_3$) δ (ppm): 1.53 (d, J=6.4 Hz, 3H), 1.74-1.85 (m, 1H), 2.03 (dd, J=12.8, 6.4 Hz, 1H), 2.12-2.18 (m, 1H), 2.41-2.52 (m, 1H), 3.92 (ddd, J=10.8, 10.8, 5.2 Hz, 1H), 4.65-4.73 (m, 1H), 5.10 (d, J=8.8 Hz, 1H), 6.76-6.84 (m, 2H).
High Polarity Title Compound
$^1$H-NMR (CDCl$_3$) δ (ppm): 1.54 (d, J=6.8 Hz, 3H), 1.84-1.95 (m, 1H), 2.15-2.23 (m, 2H), 2.43-2.54 (m, 1H), 4.39-4.44 (m, 1H), 4.87-4.93 (m, 1H), 5.08 (d, J=9.2 Hz, 1H), 6.92-7.00 (m, 2H).

Synthesis of (Z)-(1S,6S,8aR)-3-[3-methoxy-4-(4-methylimidazol-1-yl)benzylidene]-1-methyl-6-(3,4,5-trifluorophenyl)tetrahydropyrrolo[2,1-c][1,4]oxazine-4 one Under ice-cooling, L-selectride (3.78 mL, 1.02 M tetrahydrofuran solution) was added dropwise into a tetrahydrofuran (25 mL) solution containing (1S,4R,6S)-1-methyl-6-(3,4,5-trifluorophenyl)tetrahydropyrrolo[2,1-c][1,4]oxazine-3,4-dione (860 mg, high polarity compound), and stirring was continued for 1 hour at the same temperature. 5 N sodium hydroxide solution (570 µL) was added to the reaction solution, and stirring was continued for 20 minutes at 0° C. Next, hydrogen peroxide solution (279 µL, 35% solution) was added, and stirring was continued for 20 minutes at 0° C. Sodium bisulfite (298 mg) was added, and after stirring for 20 minutes at room temperature, ethyl acetate and brine were added, and the organic layer was partitioned. The organic layer was dried over anhydrous magnesium sulfate, and the solvent was removed under a vacuum. Acetonitrile (25 mL) and triphenyl phosphonium bromide (1 g) was added to the residue, and the resultant was heated under reflux for 1 hour. The resultant was returned to room temperature, and 3-methoxy-4-(4-methyl-1H-imidazol-1-yl) benzaldehyde (683 mg) and triethylamine (796 µL) were added, and stirring was continued for 10 hours at room temperature. Ethyl acetate and brine were added to the reaction solution, and the organic layer was partitioned. The organic layer was dried over anhydrous magnesium sulfate, and the solvent was removed under a vacuum, and the residue was purified by silica gel column chromatography (two times, carrier: Chromatrex NH, eluting solvent: heptane/ethyl acetate→ethyl acetate and carrier: Chromatrex, eluting solvent: heptane/ethyl acetate→ethyl acetate→ethyl acetate/methanol), and the title compound (700 mg) was obtained. The physical property values are as follows.
ESI-MS; m/z 484 [M$^+$+H]. $^1$H-NMR (CDCl$_3$) δ (ppm): 1.48 (d, J=6.8 Hz, 3H), 1.77-1.88 (m, 1H), 2.00-2.05 (m, 1H), 2.11-2.17 (m, 1H), 2.29 (s, 3H), 2.35-2.46 (m, 1H), 3.84 (s, 3H), 4.24 (ddd, J=9.2, 4.8, 4.8 Hz, 1H), 4.78-4.84 (m, 1H), 5.06 (d, J=9.6 Hz, 1H), 6.81 (s, 1H), 6.92 (dd, J=1.2, 1.2 Hz, 1H), 6.94 (dd, J=8.4, 6.0 Hz, 2H), 7.19 (d, J=8.0 Hz, 1H), 7.38 (s, 1H), 7.40 (dd, J=8.0, 1.6 Hz, 1H), 7.70 (d, J=1.2 Hz, 1H).

Synthesis of (Z)-(1R,6S,8aR)-3-[3-methoxy-4-(4-methylimidazol-1-yl)benzylidene]-1-methyl-6-(3,4,5-trifluorophenyl)tetrahydropyrrolo[2,1-c][1,4]oxazine-4 one In the same manner as in Example 6 and Example 7, the title compound (1.87 g) containing geometrical isomers was obtained from (1R,4R,6S)-1-methyl-6-(3,4,5-trifluorophenyl)tetrahydropyrrolo[2,1-c][1,4]oxazine-3,4-dione (1.6 g, low polarity compound). Trifluoroacetic acid (5 mL) and 4 N hydrochloric acid/ethyl acetate (1 mL) was added to a chloroform (5 mL) solution of the title compound (500 mg) containing geometrical isomers, and stirring was continued for 10 hours at room temperature. The solvent was removed under a vacuum, and 2 N sodium hydroxide solution and ethyl acetate were added, and the organic layer was partitioned. The organic layer was washed with brine, and the resultant was dried with magnesium sulfate. The solvent was removed under a vacuum, and the resultant was purified by silica gel column chromatography (carrier: Chromatrex NH, eluting solvent: heptane/ethyl acetate→ethyl acetate), and the title compound (480 mg) was obtained. The physical property values are as follows.
$^1$H-NMR (CDCl$_3$) δ (ppm): 1.57 (d, J=6.4 Hz, 3H), 1.70-1.81 (m, 1H), 1.91 (dd, J=13.2, 6.4 Hz, 1H), 2.07-2.14 (m, 1H), 2.29 (s, 3H), 2.34-2.45 (m, 1H), 3.72-3.79 (m, 1H), 3.86 (s, 3H), 4.21-4.29 (m, 1H), 5.13 (d, J=8.8 Hz, 1H), 6.72 (s, 1H), 6.80 (dd, J=8.0, 6.0 Hz, 2H), 6.92 (dd, J=1.2, 1.2 Hz, 1H), 7.20 (d, J=8.0 Hz, 1H), 7.33 (dd, J=8.4, 1.6 Hz, 1H), 7.54 (d, J=1.6 Hz, 1H), 7.71 (d, J=1.2 Hz, 1H).

EXAMPLE 14

Synthesis of (Z)-(6S,8aR)-6-(3,4-difluorophenyl)-3-[3-methoxy-4-(4-methylimidazol-1-yl)benzylidene]-1,1-dimethyltetrahydropyrrolo[2,1-c][1,4]oxazin-4-one

[Formula 18]

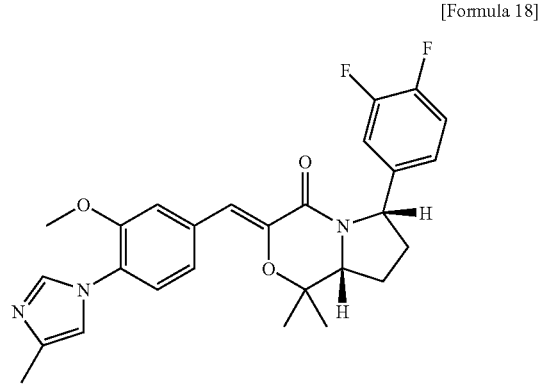

Synthesis of (R)-2-t-butoxycarbonylamino-5-oxo-5-(3,4-difluorophenyl)valeric acid ethyl ester Preparation of 3,4-difluorophenyl magnesium bromide: Under a nitrogen atmosphere, 1-bromo-3,4,5-trifluorophenyl (2 mL) was added to a diethyl ether (60 mL) suspension of magnesium (1.7 g) and iodine (one fragment), and the resultant was heated. 1-bromo-3,4-difluorphenyl (5.6 mL) was further added dropwise. After reflex was stopped, stirring was continued for 1 hour at room temperature.

Under a nitrogen atmosphere, the previously prepared 3,4-difluorophenyl magnesium bromide was added dropwise at −40° C. into a tetrahydrofuran (200 mL) solution of (R)-5-oxopyrrolidine-1,2-dicarboxylic acid 1-t-butyl ester 2-ethyl ester (15 g) obtained in Example 4. After stirring for 1 hour at the same temperature, saturated ammonium chloride aqueous solution was added, and extraction with ethyl acetate was conducted. After washing the organic layer with brine, the resultant was dried over anhydrous magnesium sulfate. The solvent was removed under a vacuum, and the residue was passed through a silica pad (carrier: Chromatrex 400 cc, eluting solvent: ethyl acetate), and the title compound (21.2 g) was obtained. The physical property values are as follows.
ESI-MS; m/z 394 [M$^+$+Na].

Synthesis of (R)-5-(3,4-difluorophenyl)-3,4-dihydro-2H-pyrrole-2-carboxylic acid ethyl ester 4 N hydrochloric acid/ethyl acetate (156 mL) was added to an ethyl acetate (30 mL) solution of (R)-2-t-butoxycarbonylamino-5-oxo-5-(3,4-difluorophenyl) valeric acid ethyl ester (21.2 g), and stirring was continued for 3 hours at room temperature. The solvent was removed under a vacuum, and ethyl acetate and sodium bicarbonate aqueous solution was added to the residue, and the organic layer was partitioned. After washing the organic layer with brine, the resultant was dried over anhydrous magnesium sulfate. The solvent was removed under a vacuum, and the title compound (12.19 g) was obtained. The physical property values were as follows.
ESI-MS; m/z 254 [M$^+$+H]. $^1$H-NMR (CDCl$_3$) δ (ppm): 1.32 (t, J=7.2 Hz, 3H), 2.21-2.30 (m, 1H), 2.32-2.41 (m, 1H), 2.89-2.98 (m, 1H), 3.06-3.14 (m, 1H), 4.23 (q, J=7.2 Hz, 2H), 4.89 (dd, J=8.4, 6.8 Hz, 1H), 7.15-7, 22 (m, 1H), 7.55-7.59 (m, 1H), 7, 73-7.78 (m, 1H).

Synthesis of (2R,5S)-5-(3,4-difluorophenyl)pyrrolidine-2-carboxylic acid ethyl ester 10% palladium on carbon (1.2 g, 50% water content) was added to an ethanol (160 mL) solution of (R)-5-(3,4 difluorophenyl)-3,4-dihydro-2H-pyrrole-2-carboxylic acid ethyl ester (12.2 g), and under a hydrogen atmosphere, stirring was continued for 16 hours at room temperature. The catalyst was filtered on celite, and the filtrate was concentrated, and ethanol (160 mL) and 10% palladium on carbon (1.2 g, 50% water content) was again added to the residue, and under a hydrogen atmosphere, stirring was continued for 15 hours at room temperature. The catalyst was filtered on celite, and the filtrate was concentrated, and the residue was purified by silica gel column chromatography (heptane/ethyl acetate), and the title compound (8.86 g) was obtained. The physical property values are as follows.
ESI-MS; m/z 256 [M$^+$+H]. $^1$H-NMR (CDCl$_3$) δ (ppm): 1.31 (t, J=7.2 Hz, 3H), 1.60-1.67 (m, 1H), 2.08-2.22 (m, 3H), 3.92 (dd, J=8.0, 4.8 Hz, 1H), 4.19 (dd, J=7.2, 4.8 Hz, 1H), 4.23 (q, J=7.2 Hz, 2H), 7.06-7.17 (m, 2H), 7.33 (ddd, J=11.2, 8.0, 2.0 Hz, 1H).

Synthesis of (2R,5S)-5-(3,4-difluorophenyl)pyrrolidine-1,2-dicarboxylic acid 1-t-butyl ester 2-ethyl ester A dimethylformamide (100 mL) solution containing (2R,5S)-5-(3,4-difluorophenyl)pyrrolidine-2-carboxylic acid ethyl ester (8.86 g), triethylamine (7.77 mL) and di-t-butyl dicarbonate (9.91 g) was stirred for 5 hours at room temperature. Imidazole (1.32 g) was added to the reaction mixture, and stirring was continued for 20 minutes at room temperature. Water and ethyl acetate were added, and the organic layer was partitioned, and the resultant was washed with 0.2 N hydrochloric acid (twice) and brine in sequence, and the organic layer was dried over anhydrous magnesium sulfate. The solvent was removed under a vacuum, and the residue was passed through a silica pad, and the title compound (12.3 g) was obtained. The physical property values are as follows.
ESI-MS; m/z 378 [M$^+$+Na].

Synthesis of 2-[(2R,5S)-5-(3,4-difluorophenyl)pyrrolidine-2-yl]propane-2-ol

Under a nitrogen atmosphere and under ice-cooling, methyl magnesium bromide (20.7 mL, 0.97 M tetrahydrofuran solution) was added dropwise into a tetrahydrofuran (60 mL) solution of (2R,5S)-5-(3,4-difluorophenyl)pyrrolidine-1,2-dicarboxylic acid 1-t-butyl ester 2-ethyl ester (2.5 g). After stirring for 2 hours at the same temperature, ammonium chloride aqueous solution and ethyl acetate were added, and the organic layer was partitioned. The organic layer was washed with brine and dried with magnesium sulfate, and the solvent was removed under a vacuum. Ethyl acetate (7 mL) and 4 N hydrochloric acid/ethyl acetate (20 mL) were added to the residue, and stirring was continued for 1 hour at room temperature. The solvent was removed under a vacuum, and ethyl acetate and sodium bicarbonate aqueous solution were added, and the organic layer was partitioned. The organic layer was washed with brine and dried over anhydrous magnesium sulfate, and the solvent was removed under a vacuum, and the title compound (1.66 g) was obtained. The physical property values are as follows.
ESI-MS; m/z 242 [M$^+$+H]. $^1$H-NMR (CDCl$_3$) δ (ppm): 1.19 (s, 3H), 1.21 (s, 3H), 1.51-1.61 (m, 1H), 1.76-1.93 (m, 2H), 2.04-2.15 (m, 1H), 2.84 (brs, 1H), 3.19 (dd, J=8.4, 6.8 Hz, 1H), 4.20 (dd, J=8.8, 7.2 Hz, 1H), 7.06-7.09 (m, 2H), 7.21 (dd, J=8.0, 1.6 Hz, 1H).

Synthesis of (6S,8aR)-6-(3,4-difluorophenyl)-1,1-dimethyltetrahydropyrrolo[2,1-c][1,4]oxazine-3,4-dione Under ice-cooling, oxalyl chloride (713 μL) was added dropwise into a chloroform (70 mL) solution containing 2-[(2R,5S)-5-(3,4-difluorophenyl)pyrrolidine-2-yl]propane-2-ol (1.66 g) and pyridine (10 mL). After stirring for 30 minutes at the same temperature, water was added to the reaction solution, and the organic layer was partitioned. After washing the organic layer with brine, the resultant was dried over anhydrous magnesium sulfate. The solvent was removed under a vacuum, and the resulting solid was washed with a mixture solvent of ether/heptane (1/1), and the title compound (1.3 g) was obtained. The physical property values are as follows.
ESI-MS; m/z 296 [M$^+$+H]. $^1$H-NMR (CDCl$_3$) δ (ppm): 1.51 (s, 3H), 1.54 (s, 3H), 1.87-1, 98 (m, 1H), 2.16-2.22 (m, 2H), 2.41-2.52 (m, 1H), 4.12 (dd, J=11.6, 6.4 Hz, 1H), 5.14 (d, J=9.2 Hz, 1H), 7.07-7.19 (m, 3H).

Synthesis of (Z)-(6S,8aR)-6-(3,4-difluorophenyl)-3-[3-methoxy-4-(4-methylimidazol-1-yl)benzylidene]-1,1-dimethyltetrahydropyrrolo[2,1-c][1,4]oxazin-4-one Under ice-cooling, L-selectride (5.71 mL, 1.02 M tetrahydrofuran solution) was added dropwise into a tetrahydrofuran (40 mL) solution containing (6S,8aR)-6-(3,4-difluorophenyl)-1,1-dimethyltetrahydropyrrlo [2,1-c][1,4]oxazine-3,4-dione (1.3 g). Stirring was continued for 1 hour at the same temperature. 5 N sodium hydroxide solution (862 μL) was added to the reaction solution, and stirring was continued for 20 minutes at 0° C., and next, hydrogen peroxide solution (422 μL, 35% solution) was added, and stirring was continued for 20 minutes at 0° C. Sodium bisulfite (450 mg) was added, and after stirring for 20 minutes at room temperature, ethyl acetate and brine were added, and the organic layer was partitioned. The organic layer was dried over anhydrous magnesium sulfate, and the solvent was removed under a vacuum. Acetonitrile (40 mL) and triphenyl phosphonium bromide (1.51 g) were added to the residue, and the resultant was heated under reflux for 1 hour. The resultant was returned to room temperature, and 3-methoxy-4-(4-methyl-1H-imidazol-1-yl) benzaldehyde (1.03 g) and triethylamine (1.2 mL) were added, and stirring was continued for 50 hours at room temperature. Ethyl acetate and brine were added to the reaction solution, and the organic layer was partitioned. The organic layer was dried over anhydrous magnesium sulfate, and the solvent was removed under a vacuum, and the residue was purified by silica gel column chromatography (two times) (carrier: Chromatrex NH, eluting solvent: heptane/ ethyl acetate→ethyl acetate; and carrier: Chromatrex, eluting solvent: heptane/ethyl acetate→ethyl acetate→ethyl acetate/ methanol), and the title compound (1.36 g) was obtained. The physical property values are as follows.

ESI-MS; m/z 480 [M$^+$+H]. $^1$H-NMR (CDCl$_3$) δ (ppm): 1.46 (s, 3H), 1.58 (s, 3H), 1.80-1.91 (m, 1H), 2.01-2.15 (m, 2H), 2.30 (s, 3H), 2.34-2.45 (m, 1H), 3.85 (s, 3H), 3.94 (dd, J=12.0, 5.2 Hz, 1H), 5.12 (d, J=9.2 Hz, 1H), 6.79 (s, 1H), 6.92 (s, 1H), 7.04-7.17 (m, 3H), 7.19 (d, J=8.0 Hz, 1H), 7.32 (dd, J=8.0, 1.6 Hz, 1H), 7.54 (d, J=1.2 Hz, 1H), 7.71 (d, J=1.2 Hz, 1H).

EXAMPLE 15

Synthesis of (Z)-(1S,6S,8aR)-6-(3,4-difluorophenyl)-3-[3-methoxy-4-(4-methylimidazol-1-yl)benzylidene]-1-methyltetrahydropyrrolo[2,1-c][1,4]oxazin-4-one

[Formula 19]

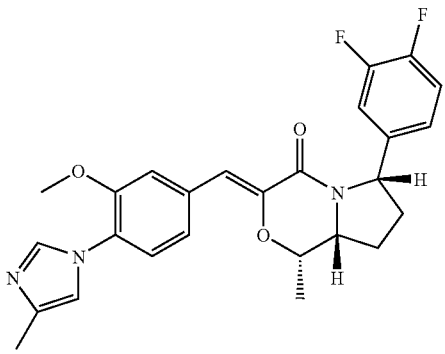

Synthesis of (2S,5R)-2-(4-fluorophenyl)-5-hydroxymethyl-pyrrolidine-1-carboxylic acid t-butyl ester Under ice-cooling, lithium borohydride (369 mg) was added to a tetrahydrofuran (50 mL) solution of (2R,5S)-5-(3, 4-fluorophenyl)pyrrolidine-1,2-dicarboxylic acid 1-t-butyl ester 2-ethyl ester (4 g) obtained in Example 14, and stirring was continued for 30 minutes at the same temperature and for 13 hours at room temperature. Water and ethyl acetate were added, and the organic layer was partitioned. The organic layer was washed with brine and dried over anhydrous magnesium sulfate. The solvent was removed under a vacuum, and the residue was purified by silica gel column chromatography (heptane/ethyl acetate), and the title compound (3.18 g) was obtained. The physical property values are as follows.

ESI-MS; m/z 318 [M$^+$+Na]. $^1$H-NMR (CDCl$_3$) δ (ppm): 1.24 (brs, 9H), 1.56-1.70 (m, 1H), 1.77-1.86 (m, 1H), 1.99-2.07 (m, 1H), 2.23-2.31 (m, 1H), 3.73-3.81 (m, 2H), 4.10-4.20 (m, 1H), 4.62 (brs, 1H), 4.78 (dd, J=7.2, 6.4 Hz, 1H), 6.95-6.99 (m, 1H), 7.03-7.13 (m, 2H).

Synthesis of (2S,5R)-2-(3,4-difluorophenyl)-5-((R)-1-hydroxyethyl)-pyrrolidine-1-carboxylic acid t-butyl ester and (2S,5R)-2-(3,4-difluorophenyl)-5-((S)-1-hydroxyethyl)-pyrrolidine-1-carboxylic acid t-butyl ester A tetrahydrofuran (60 mL) solution containing dimethyl sulfoxide (1.15 mL) was cooled to −78° C., and oxalyl chloride (1.29 mL) was added dropwise. After stirring for 5 minutes at the same temperature, a tetrahydrofuran (10 mL) solution of (2S,5R)-2-(3,4-difluorophenyl)-5-hydroxymethyl-pyrrolidine-1-carboxylic acid t-butyl ester (3.18 g) was added dropwise. After stirring the resultant for 40 minutes at the same temperature, triethylamine (5.95 mL) was added, and stirring was continued for 1 hour from −78° C. to room temperature. Ammonium chloride aqueous solution was added to the reaction solution, and the organic layer was partitioned. The organic layer was washed with brine and dried over anhydrous magnesium sulfate. The solvent was removed under a vacuum, and tetrahydrofuran (68 mL) was added to the residue, and the resultant was cooled to −78° C. Methyl magnesium bromide (11.8 mL, 0.97 M tetrahydrofuran solution) was added dropwise into the reaction solution, and stirring was continued for 1 hour at the same temperature. Ammonium chloride aqueous solution and ethyl acetate were added to the reaction solution, and the organic layer was partitioned. The organic layer was washed with brine and dried with magnesium sulfate. The solvent was removed under a vacuum. The residue was purified by silica gel column chromatography (heptane/ethyl acetate), and the low polarity title compound (795 mg) and the high polarity title compound (879 mg) were obtained. Their physical property values are as follows.

Low Polarity Title Compound $^1$H-NMR (CDCl$_3$) δ (ppm): 1.21 (s, 9H), 1.23 (d, J=6.4 Hz, 3H), 1.64-1.71 (m, 1H), 1.78-1.87 (m, 1H), 1.96-2.05 (m, 1H), 2.21-2.28 (m, 1H), 3.77-3.84 (m, 1H), 3.85-3.91 (m, 1H), 4.79 (dd, J=7.2, 7.2 Hz, 1H), 5.12 (brs, 1H), 6.96-7.02 (m, 2H), 7.22-7.26 (m, 2H).

High Polarity Title Compound $^1$H-NMR (CDCl$_3$) δ (ppm): 1.22 (d, J=6.4 Hz, 3H), 1.27 (s, 9H), 1.88-1.99 (m, 3H), 2.16-2.26 (m, 1H), 3.92-4.0 (brm, 1H), 4.08-4.16 (m, 1H), 4.74-4.82 (m, 1H), 6.95-7.01 (m, 2H), 7.26-7.30 (m, 2H).

Synthesis of (S)-1-[(2R,5S)-5-(3,4-fluorophenyl) pyrrolidine-2-yl]ethanol

A 4 N hydrochloric acid/ethyl acetate (6.8 mL) solution of (2S,5R)-2-(3,4-difluorophenyl)-5-((S)-1-hydroxyethyl)-pyrrolidine-1-carboxylic acid t-butyl ester (879 mg, high polarity compound) was stirred for 3 hours at room temperature. The solvent was removed under a vacuum, and ethyl acetate and sodium bicarbonate aqueous solution were added, and the organic layer was partitioned. The organic layer was washed with brine and dried over anhydrous magnesium sulfate, and the solvent was removed under a vacuum, and the title compound (602 mg) was obtained. The physical property values are as follows.

ESI-MS; m/z 228 [M$^+$+H]

Synthesis of (R)-6-[(S)-3,4-difluorophenyl]-1-methyltetrahydropyrrolo[2,1-c][1,4]oxazin-3,4-dione Under ice-cooling, oxalyl chloride (340 μL) was added dropwise into a chloroform (25 mL) solution containing (S)-1-[(2R,5S)-5-(3,4-difluorophenyl)pyrrolidine-2-yl]ethanol (602 mg) and pyridine (5 mL). Stirring was continued for 30 minutes at the same temperature. Water was added, and the organic layer was partitioned and then dried over anhydrous magnesium sulfate. The solvent was removed under a vacuum, and the residue was purified by silica gel column chromatography (heptane/ethyl acetate→ethyl acetate), and the title compound (297 mg) was obtained. The physical property values are as follows.

ESI-MS; m/z 282 [M++H]. $^1$H-NMR (CDCl$_3$) δ (ppm): 1.52 (d, J=6.8 Hz, 3H), 1.87-1.98 (m, 1H), 2.17-2.23 (m, 2H), 2.43-2.54 (m, 1H), 4.40-4.46 (m, 1H), 4.87-4.93 (m, 1H), 5.13 (d, J=9.2 Hz, 1H), 7.07-7.19 (m, 3H).

Synthesis of (Z)-(1S,6S,8aR)-6-(3,4-difluorophenyl)-3-[3-methoxy-4-(4-methylimidazol-1-yl)benzylidene]-1-methyltetrahydropyrrolo[2,1-c][1,4]oxazin-4-one Under ice-cooling, L-selectride (1.3 mL, 1.02 M tetrahydrofuran solution) was added dropwise into a tetrahydrofuran (10 mL) solution containing (R)-6-[(S)-3,4-difluorophenyl]-1-methyltetrahydropyrrolo[2,1-c][1,4]oxazin-3,4-dione (297 mg). Stirring was continued for 1.5 hours at the same temperature. A 5 N sodium hydroxide solution (197 μL) was added to the reaction solution, and stirring was continued for 10 minutes at 0° C., and next hydrogen peroxide solution (96 μL, 35% solution) was added, and stirring was continued for 10 minutes at 0° C. Sodium bisulfite (103 mg) was added, and after stirring for 20 minutes at room temperature, ethyl acetate and brine were added, and the organic layer was partitioned. The organic layer was dried over anhydrous magnesium sulfate, and the solvent was removed under a vacuum. Acetonitrile (10 mL) and triphenyl phosphonium bromide (345 mg) were added to the residue, and the resultant was heated under reflux for 2 hours. The resultant was returned to room temperature, and 3-methoxy-4-(4-methyl-1H-imidazol-1-yl)benzaldehyde (235 mg) and triethylamine (274 μL) were added, and the resultant was stirred at room temperature for 20 hours. The solvent was removed under a vacuum, and ethyl acetate and brine were added, and the organic layer was partitioned. The organic layer was dried over anhydrous magnesium sulfate, and the solvent was removed under a vacuum, and the residue was purified by silica gel column chromatography (carrier: Chromatrex NH and Chromatrex, eluting solvent: hexane/ethyl acetate→ethyl acetate→ethyl acetate/methanol), and the title compound (260 mg) was obtained. The physical property values are as follows.

ESI-MS; m/z 466 [M++H]. $^1$H-NMR (CDCl$_3$) δ (ppm): 1.47 (d, J=6.8 Hz, 3H), 1.80-1.91 (m, 1H), 2.02-2.07 (m, 1H), 2.10-2.17 (m, 1H), 2.29 (s, 3H), 2.35-2.46 (m, 1H), 3.84 (s, 3H), 4.23-4.28 (m, 1H), 4.78-4.84 (m, 1H), 5.11 (d, J=9.6 Hz, 1H), 6.81 (s, 1H), 6.91 (dd, J=1.2, 1.2 Hz, 1H), 7.04-7.15 (m, 3H), 7.19 (d, J=8.0 Hz, 1H), 7.38-7.40 (m, 1H), 7.38 (s, 1H), 7.69 (d, J=1.2 Hz, 1H).

EXAMPLE 16 AND 17

Synthesis of (Z)-(1R,6S,9aR)-3-[3-methoxy-4-(4-methylimidazol-1-yl)benzylidene]-1-methyl-6-(3,4,5-trifluorophenyl)hexahydropyrido[2,1-c][1,4]oxazin-4-one and (Z)-(1S,6S,9aR)-3-[3-methoxy-4-(4-methylimidazol-1-yl)benzylidene]-1-methyl-6-(3,4,5-trifluorophenyl)hexahydropyrido[2,1-c][1,4]oxazin-4-one

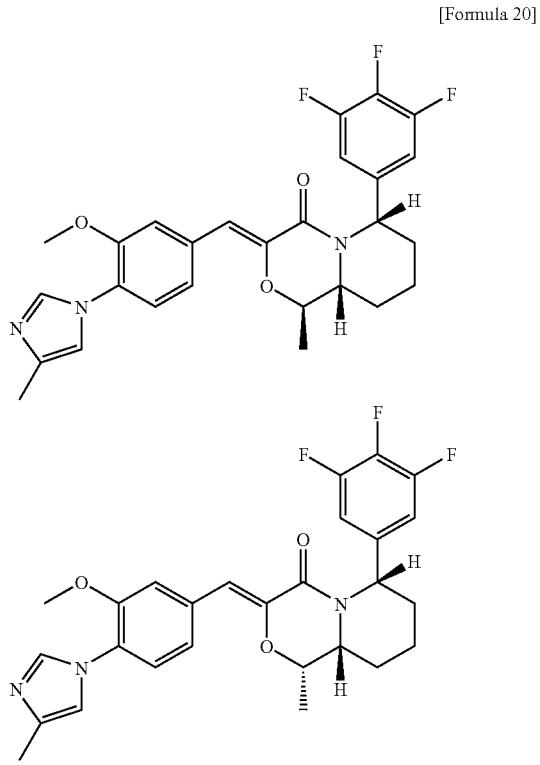

[Formula 20]

Synthesis of (R)-6-oxopiperidine-1,2-dicarboxylic acid 1-tertiary butyl ester 2-methyl ester At −20° C., thionyl chloride (206 mL) was added to methanol (750 mL) over 1 hour, and the reaction solution was stirred for 15 minutes at −20° C. (R)-6-oxopiperidine-2-carboxylic acid (CAS# 72002-30-3) (26.0 g) was added to the reaction solution at −20° C. The resultant reaction solution was stirred for 13 hours at room temperature. Afterwards, the reaction solution was concentrated under a vacuum. At 0° C., triethylamine (62.2 mL), DMAP (13.6 g), and next di-tertiary-butyl carbonate (146 g) were added to an acetonitrile (700 mL) solution of the residue. The reaction solution was stirred for 2 days at room temperature. The reaction solution was concentrated under a vacuum, and ethyl acetate and saturated sodium bicarbonate solution were added to the residue, and the organic layer was partitioned, and the resultant organic layer was further washed with brine. After drying the resulting organic layer with magnesium sulfate, the resultant was concentrated under a vacuum. By purifying the residue by silica gel column chromatography (eluting solvent: heptane-ethyl acetate system), 32.5 g of the title compound was obtained. The physical property values are as follows.

$^1$H-NMR (CDCl$_3$) δ (ppm): 1.50 (s, 9H), 1.65-1.85 (m, 2H), 2.00-2.09 (m, 1H), 2.12-2.21 (m, 1H), 2.45-2.63 (m, 2H), 3.77 (s, 3H), 4.68-4.74 (s, 1H).

Synthesis of (2R,6S)-6-(3,4,5-trifluorophenyl)piperidine-2-carboxylic acid methyl ester Under a nitrogen atmosphere and at −78° C., 3,4,5-trifluorophenyl magnesium bromide (prepared from 1-bromo-3,4,5-trifluorobenzene (11.7 g) and magnesium (1.48 g) according to the method described in Org. Synth., 2001, 79, 176) was added to a THF (140 mL) solution of (R)-6-oxopiperidine-1,2-dicarboxylic acid 1-tertiery butyl ester (13.0 g) over 30 minutes. The reaction solution was stirred for 2 hours from −78° C. to −10° C. Afterwards, at −10° C., the resultant reaction was quenched with saturated ammonium chloride aqueous solution. Water was added to the reaction solution, and extraction with ethyl acetate was conducted. After drying the resulting extraction solution with magnesium sulfate, concentration under a vacuum was conducted. A 4 N hydrochloric acid ethyl acetate solution (150 mL) was added at room temperature to an ethyl acetate (150 mL) solution of the residue. The resultant reaction solution was stirred for 9 hours at room temperature. The reaction solution was concentrated under a vacuum, and after making the residue basic by adding saturated sodium bicarbonate solution, chloroform was added, and stirring was continued for 2 hours at room temperature. The organic layer was partitioned, and after drying with magnesium sulfate, the resultant was concentrated under a vacuum. 10% palladium on carbon (700 mg) was added to a methanol (200 mL) solution of the residue, and the resultant reaction solution was stirred for 9 hours under a hydrogen atmosphere and at room temperature. The reaction solution was filtered over celite, and the filtrate was concentrated under a vacuum. By purifying the residue by silica gel column chromatography (eluting solvent:heptane-ethyl acetate system), 5.47 g of the title compound was obtained. The physical property values are as follows.

ESI-MS; m/z 274 [M$^+$+H]

Synthesis of [(2R,6S)-6-(3,4,5-trifluorophenyl)piperidine-2-yl]methanol

Under a nitrogen atmosphere, a tetrahydrofuran (10 mL) solution of (2R,6S)-6-(3,4,5-trifluorophenyl)piperidine-2-carboxylic acid methyl ester (3.25 g) was added dropwise at −20° C. into a tetrahydrofuran (50 mL) suspension of lithium aluminum hydride (621 mg). After confirming the disappearance of the raw materials, water (0.62 mL), 5 N sodium hydroxide solution (0.62 mL), and water (1.86 mL) were added in sequence to the reaction solution at the same temperature. After stirring for 15 minutes at the same temperature, ethyl acetate was added, and the resultant was filtered on celite. The filtrate was passed through a silica pad (carrier: Chromatrex NH, eluting solvent: ethyl acetate), and by removing the solvent under a vacuum, the title compound (2.87 g) was obtained. The physical property values are as follows.

ESI-MS; m/z 246 [M$^+$+H]

Synthesis of (2R,6S)-2-hydroxymethyl-(3,4,5-trifluorophenyl)piperidine-1-carboxylic acid benzyl ester Saturated sodium bicarbonate aqueous solution (5 mL) was added to a tetrahydrofuran (5 mL) solution of [(2R,6S)-6-(3,4,5-trifluorophenyl)piperidine-2-yl]methanol (500 mg), and benzyl chloroformate (379 μL) was added dropwise. After stirring for 16 hours at room temperature, water and ethyl acetate were added to the reaction solution, and the organic layer was partitioned. The organic layer was washed with brine, and the resultant was dried with magnesium sulfate. The solvent was removed under a vacuum, and the residue was purified by silica gel column chromatography (heptane/ethyl acetate), and the title compound (670 mg) was obtained. The physical property values are as follows.

ESI-MS; m/z 380 [M$^+$+H]. $^1$H-NMR (CDCl$_3$) δ (ppm): 1.51-1.59 (m, 1H), 1.68-2.04 (m, 4H), 2.13-2.20 (m, 1H), 3.32-3.36 (m, 2H), 4.94-4.55 (m, 1H), 5.12-5.22 (m, 2H), 5.30-5.35 (brm, 1H), 7.00 (dd, J=8.4, 6.8 Hz, 2H), 7.25-7.36 (m, 5H).

Synthesis of (2R,6S)-2-((R)-1-hydroxyethyl)-6-(3,4,5-trifluorophenyl)piperidine-1-carboxylic acid benzyl ester and (2R,6S)-2-((S)-1-hydroxyethyl)-6-(3,4,5-trifluorophenyl)piperidine-1-carboxylic acid benzyl ester A tetrahydrofuran (12 mL) solution containing dimethyl sulfoxide (200 μL) was cooled to −78° C., and oxalyl chloride (227 μL) was added dropwise. After stirring for 5 minutes at the same temperature, a tetrahydrofuran (3 mL) solution of (2R,6S)-2-hydroxymethyl-(3,4,5-trifluorophenyl)piperidine-1-carboxylic acid benzyl ester (670 mg) was added dropwise. After stirring for 40 minutes at the same temperature, triethylamine (1.25 mL) was added, and stirring was continued for 1 hour from −78° C. to room temperature. Ammonium chloride aqueous solution and ethyl acetate were added to the reaction solution, and the organic layer was partitioned. The organic layer was washed with brine, and the resultant was dried over anhydrous magnesium sulfate. The solvent was removed under a vacuum, and tetrahydrofuran (14.4 mL) was added to the residue, and the resultant was cooled to −78° C. Methyl magnesium bromide (2.49 mL, 0.97 M tetrahydrofuran solution) was added dropwise into the reaction solution, and stirring was continued for 1 hour at the same temperature. Ammonium chloride aqueous solution and ethyl acetate were added to the reaction solution, and the organic layer was partitioned. The organic layer was washed with brine, and the resultant was dried with magnesium sulfate, and the solvent was removed under a vacuum. The residue was purified by silica gel column chromatography (heptane/ethyl acetate), and a diastereomer mixture (600 mg) of the title compound was obtained. The physical property values are as follows.

ESI-MS; m/z 380 [M$^+$+H].

Synthesis of (S)-1-[(2R,6S)-6-(3,4,5-trifluorophenyl)piperidine-2-yl]ethanol and (R)-1-[(2R,6S)-6-(3,4,5-trifluorophenyl)piperidine-2-yl]ethanol 10% palladium on carbon (60 mg, 50% water content) was added to a methanol (6 mL) solution of the diastereomer mixture (600 mg) of (2R,6S)-2-((R)-1-hydroxyethyl)-6-(3,4,5-trifluorophenyl)piperidine-1-carboxylic acid benzyl ester and (2R,6S)-2-((S)-1-hydroxyethyl)-6-(3,4,5-trifluorophenyl)piperidine-1-carboxylic acid benzyl ester, and under a hydrogen atmosphere, stirring was continued for 2 hours at room temperature. The resultant was filtered on celite, and by removing the solvent under a vacuum, the diastereomer mixture (380 mg) of the title compound was obtained. The physical property values are as follows.

ESI-MS; m/z 260 [M$^+$+H].

Synthesis of (1R,6S,9aR)-1-methyl-6-(3,4,5-trifluorophenyl)hexahydropyrido[2,1-c][1,4]oxazine-3,4-dione and (1S,6S,9aR)-1-methyl-6-(3,4,5-trifluorophenyl)hexahydropyrido[2,1-c][1,4]oxazine-3,4-dione Under ice-cooling, oxalyl chloride (189 μL) was added dropwise into a chloroform (10 mL) solution of pyridine (2 mL) and the diastereomer mixture (380 mg) of (S)-1-[(2R,6S)-6-(3,4,5-trifluorophenyl)piperidine-2-yl]ethanol and (R)-1-[(2R,6S)-6-(3,4,5-trifluorphenyl)piperidine-2-yl]. Stirring was continued for 1 hour at the same temperature. Water was added, and the organic layer was partitioned, and the resultant was dried with magnesium sulfate. The solvent was removed under a vacuum, and the residue was purified by silica gel column chromatography (heptane/ethyl acetate→ethyl acetate), and a diastereomer mixture (160 mg) of the title compound was obtained. The physical property values are as follows.
ESI-MS; m/z 314 [M$^+$+H].

Synthesis of (1R,6S,9aR)-3-[3-methoxy-4-(4-methylimidazol-1-yl)benzylidene]-1-methyl-6-(3,4,5-trifluorophenyl)hexahydropyrido[2,1-c][1,4]oxazin-4-one and (1S,6S,9aR)-3-[3-methoxy-4-(4-methylimidazol-1-yl)benzylidene]-1-methyl-6-(3,4,5-trifluorophenyl)hexahydropyrido[2,1-c][1,4]oxazin-4-one Under ice-cooling, L-selectride (0.70 mL, 1.02 M tetrahydrofuran solution) was added dropwise into a tetrahydrofuran (5 mL) solution containing the diastereomer mixture (160 mg) of (1R,6S,9aR)-1-methyl-6-(3,4,5-trifluorophenyl)hexahydropyrido[2,1-c][1,4]oxazine-3,4-dione and (1S,6S,9aR)-1-methyl-6-(3,4,5-trifluorophenyl)hexahydropyrido[2,1-c][1,4]oxazine-3,4-dione, and stirring was continued for hour at the same temperature. A 5 N sodium hydroxide solution (106 μL) was added to the reaction solution, and stirring was continued for 20 minutes at 0° C. Next, hydrogen peroxide solution (52 L, 35% solution) was added, and stirring was continued for 20 minutes at 0° C. Sodium bisulfite (55 mg) was added, and after stirring for 20 minutes at room temperature, ethyl acetate and brine were added, and the organic layer was partitioned. The organic layer was dried over anhydrous magnesium sulfate, and the solvent was removed under a vacuum. Acetonitrile (5 mL) and triphenyl phosphonium bromide (186 mg) was added to the residue, and the resultant was heated under reflux for 1 hour. The resultant was returned to room temperature, and 3-methoxy-4-(4-methyl-1H-imidazol-1-yl)benzaldehyde (127 mg) and triethylamine (148 μL) were added, and stirring was continued for 16 hours at room temperature. The solvent was removed under a vacuum, and ethyl acetate and brine were added, and the organic layer was partitioned. The resultant was dried over anhydrous magnesium sulfate, and the solvent was removed under a vacuum, and the residue was purified by silica gel column chromatography (carrier: Chromatrex NH and Chromatrex, eluting solvent: hexane/ethyl acetate→ethyl acetate→ethyl acetate/methanol), and the diastereomer mixture (135 mg) of the title compound was obtained. The physical property values are as follows.
ESI-MS; m/z 498 [M$^+$+H]
The resulting diastereomer mixture (10 mg) was fractionated with CHIRALPAK™ IA made by Daicel (2 cm×25 cm: transition phase; hexane/ethanol 7/3). An optically active title compound (2.7 mg) with a retention time of 40 minutes and an optically active title compound (3.6 mg) with a retention time of 61 minutes were obtained. The physical property values for the optically active title compound with retention time of 40 minutes are as follows.
$^1$H-NMR (CDCl$_3$) δ (ppm): 1.33-1.70 (m, 3H), 1.50 (d, J=6.0 Hz, 3H), 1.81-1.87 (m, 1H), 2.10-2.24 (m, 2H), 2.29 (s, 3H), 3.70-3.77 (m, 1H), 3.86 (s, 3H), 4.13-4.20 (m, 1H), 5.32 (brs, 1H), 6.78 (s, 1H), 6.87 (dd, J=8.4, 6.4 Hz, 2H), 6.93 (dd, J=1.2, 1.2 Hz, 1H), 7.20 (d, J=8.0 Hz, 1H), 7.32 (dd, J=8.0, 1.6 Hz, 1H), 7.53 (d, J=1.2 Hz, 1H), 7.73 (d, J=1.2 Hz, 1H).
The physical property values for the optically active title compound with a retention time of 61 minutes are as follows.
$^1$H-NMR (CDCl$_3$) δ (ppm): 1.45 (d, J=6.4 Hz, 3H), 1.60-1.85 (m, 4H), 2.09-2.29 (m, 2H), 2.29 (s, 3H), 3.84 (s, 3H), 4.00-4.07 (m, 1H), 4.49-4.55 (m, 1H), 5.02 (dd, J=5.6, 5.6 Hz, 1H), 6.84 (s, 1H), 6.91 (s, 1H), 6.95 (dd, J=8.0, 6.4 Hz, 2H), 7.19 (d, J=8.0 Hz, 1H), 7.36 (dd, J=8.0, 1.6 Hz, 1H), 7.40 (d, J=1.6 Hz, 1H), 7.70 (d, J=1.2 Hz, 1H).

EXAMPLE 18

Synthesis of (Z)-(6S,8aR)-3-[(3-methoxy-4-(4-methylimidazol-1-yl)benzylidene]-1,1-cyclopropyl-6-(3,4,5-trifluorophenyl)tetrahydropyrrolo[2,1-c][1,4]oxazin-4-one

[Formula 21]

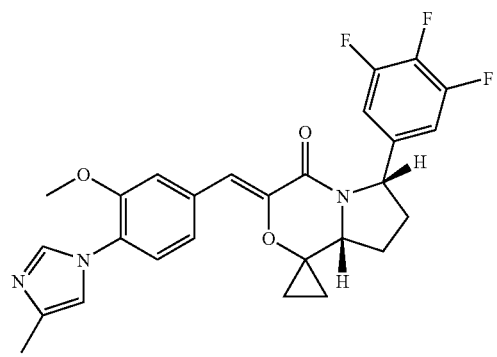

Synthesis of (2R,5S)-1-benzyl-5-(3,4,5-trifluorophenyl)pyrrolidine-2-carboxylic acid ethyl ester Benzaldehyde (2.46 mL) and acetic acid (3 mL) were added to a tetrahydrofuran/methanol (80 mL, 4/1) solution of (2R,5S)-5-(3,4,5-trifluorophenyl)pyrrolidine-2-carboxylic acid ethyl ester (3.42 g) obtained in Example 14. Stirring was continued for 10 minutes at room temperature. Sodium triacetoxybrohydride (5.15 g) was added to the reaction solution, and stirring was continued for 3.5 days. Ammonium chloride aqueous solution and ethyl acetate were added, and the organic layer was partitioned. The organic layer was washed with brine, and the resultant was dried with magnesium sulfate. The solvent was removed under a vacuum, and the residue was purified by silica gel column chromatography (heptane/ethyl acetate), and the title compound (3.43 g) was obtained. The physical property values are as follows.
ESI-MS; m/z 364 [M$^+$+H]. $^1$H-NMR (CDCl$_3$) δ (ppm): 1.18 (t, J=6.8 Hz, 3H), 1.75-1.82 (m, 1H), 1.94-1.98 (m, 1H), 2.02-2.13 (m, 2H), 3.50 (dd, J=8.8, 4.8 Hz, 1H), 3.57 (d, J=13.6 Hz, 1H), 3.76 (dd, J=8.4, 5.6 Hz, 1H), 3.82 (d, J=13.6 Hz, 1H), 3.98 (q, J=6.8 Hz, 2H), 7.14-7.25 (m, 2H).

Synthesis of 1-[(2R,5S)-1-benzyl-5-(3,4,5-trifluorophenyl)pyrrolidine-2-yl]cyclopropanol Under a nitrogen atmosphere and at room temperature, ethyl magnesium bromide (8.49 mL, tetrahydrofuran 1M solution) was added dropwise over 1 hour into an ether (10 mL) solution of (2R,5S)-1-benzyl-5-(3,4,5-trifluorophenyl) pyrrolidine-2-carboxylic acid ethyl ester (1.03 g) and titanium tetraisopropoxide (209 µL). The resultant was stirred at the same temperature for 15 hours. The reaction solution was ice-cold, and 1 N hydrochloric acid was added, stirring was continued for 30 minutes at the same temperature. Ethyl acetate was added, and the organic layer was partitioned, and after washing the organic layer with brine, the resultant was dried with magnesium sulfate. The solvent was removed under a vacuum, and the residue was purified by silica gel column chromatography, and the title compound (602 mg) was obtained. The physical property values are as follows.

ESI-MS; m/z 348 [M$^+$+H]. $^1$H-NMR (CDCl$_3$) δ (ppm): 0.30-0.38 (m, 2H), 0.54-0.58 (m, 1H), 0.75-0.79 (m, 1H), 1.64-1.74 (m, 1H), 1.88-1.97 (m, 1H), 2.02-2.08 (m, 1H), 2.10-2.19 (m, 1H), 2.45 (dd, J=8.8, 2.0 Hz, 1H), 2.99 (s, 1H), 3.69-3.83 (m, 3H), 6.93 (dd, J=8.8, 6.8 Hz, 2H), 7.08 (dd, J=8.0, 2.0 Hz, 1H), 7.17-7.24 (m, 3H).

Synthesis of 1-[(2R,5S)-5-(3,4,5-trifluorophenyl)pyrrolidine-2-yl]cyclopropanol 20% palladium hydroxide on carbon (100 mg, 50% water contain) was added to an ethanol (7 mL) solution of 1-[(2R,5S)-1-benzyl-5-(3,4,5-trifluorophenyl)pyrrolidine-2-yl]cyclopropanol (600 mg). Under a hydrogen atmosphere, stirring was continued for 3 hours. The resultant was filtered on celite, and by removing the solvent under a vacuum, the title compound (440 mg) was obtained. The physical property values are as follows.

ESI-MS; m/z 258 [M$^+$+H]. $^1$H-NMR (CDCl$_3$) δ (ppm): 0.43-0.53 (m, 2H), 0.73-0.78 (m, 1H), 0.85-0.91 (m, 1H), 1.57-1.67 (m, 1H), 1.87-2.15 (m, 3H), 2.97 (dd, J=8.0, 6.4 Hz, 1H), 4.17 (dd, J=8.0, 7.2 Hz, 1H), 7.03 (dd, J=7.8, 7.2 Hz, 2H).

Synthesis of (6S,8aR)-1,1-cyclopropyl-6-(3,4,5-trifluorophenyl)tetrahydropyrrolo[2,1-c][1,4]oxazine-3,4-dione Oxalyl chloride (189 µL) was added dropwise into a chloroform (15 mL) solution of pyridine (3 mL) and 1-[(2R,5S)-5-(3,4,5-trifluorophenyl)pyrrolidine-2-yl]cyclopropanol (440 mg). Stirring was continued for 1 hour at the same temperature. Water was added to the reaction solution, and the organic layer was partitioned and washed with brine. The organic layer was dried with magnesium sulfate, and the solvent was removed under a vacuum. The residue was purified by silica gel column chromatography (heptane/ethyl acetate→ethyl acetate), and the title compound (250 mg) was obtained. The physical property values are as follows.

ESI-MS; m/z 312 [M$^+$+H]. $^1$H-NMR (CDCl$_3$) δ (ppm): 0.88-0.94 (m, 1H), 1.14-1.21 (m, 1H), 1.26-1.33 (m, 1H), 1.37-1.49 (m, 2H), 1.91 (ddd, J=12.0, 6.4, 5.6 Hz, 1H), 2.02 (dd, J=13.2, 6.8 Hz, 1H), 2.43-2.54 (m, 1H), 4.72 (dd, J=11.6, 5.6 Hz, 1H), 5.15 (d, J=8.8 Hz, 1H), 6.84 (dd, J=8.0, 6.4 Hz, 2H).

Synthesis of (6S,8aR)-3-[3-methoxy-4-(4-methylimidazol-1-yl)benzylidene]-1,1-cyclopropyl-6-(3,4,5-trifluorophenyl)tetrahydropyrrolo[2,1-c][1,4]oxazin-4-one Under ice-cooling, L-selectride (1.3 mL, 1.02 M tetrahydrofuran solution) was added dropwise into a tetrahydrofuran (13 mL) solution containing (6S,8aR)-1,1-cyclopropyl-6-(3,4,5-trifluorophenyl)tetrahydropyrrolo[2,1-c][1,4]oxazine-3,4-dione (377 mg). Stirring was continued for 40 minutes at the same temperature. A 5 N sodium hydroxide solution (251 µL) was added to the reaction solution, and stirring was continued for 10 minutes at 0° C., and next hydrogen peroxide solution (245 µL, 35% solution) was added, and stirring was continued for 10 minutes at 0° C. Sodium bisulfite (260 mg) was added, and after stirring for 20 minutes at room temperature, ethyl acetate and brine were added, and the organic layer was partitioned. The organic layer was dried over anhydrous magnesium sulfate, and the solvent was removed under a vacuum. Acetonitrile (13 mL) and triphenyl phosphonium bromide (439 mg) were added to the residue, and the resultant was heated under reflux for 1 hour. The resultant was returned to room temperature, and 3-methoxy-4-(4-methyl-1H-imidazol-1-yl)benzaldehyde (299 mg) and triethylamine (348 µL) were added, and stirring was continued for 12 hours at room temperature. Ethyl acetate and brine were added to the reaction solution, and the organic layer was partitioned. The resultant was dried over anhydrous magnesium sulfate, and the solvent was removed under a vacuum. The residue was crudely purified by silica gel column chromatography (carrier: Chromatrex NH, eluting solvent: hexane/ethyl acetate→ethyl acetate). A crude material (100 mg) containing the title compound was obtained. The resulting crude material (20 mg) was purified by Daicel CHIRALPAK™ IA (2 cm×25 cm: transition phase; hexane/ethanol 1/1), and the title compound (3.8 mg) was obtained. The physical property values are as follows.

ESI-MS; m/z 496 [M$^+$+H]. $^1$H-NMR (CDCl$_3$) δ (ppm): 0.91-0.96 (m, 1H), 1.01-1.13 (m, 2H), 1.32-1.41 (m, 2H), 1.82-1.94 (m, 2H), 2.29 (s, 3H) 2.37-2.46 (m, 1H), 3.83 (s, 3H), 4.61 (dd, J=11.6, 4.8 Hz, 1H), 5.18 (d, J=8.8 Hz, 1H), 6.80 (s, 1H), 6.86 (dd, J=8.0, 6.0 Hz, 2H), 6.91 (dd, J=1.2, 1.2 Hz, 1H), 7.18 (d, J=8.0 Hz, 1H), 7.26 (dd, J=8.4, 1.6 Hz, 1H), 7.36 (d, J=1.2 Hz, 1H), 7.70 (d, J=1.6 Hz, 1H).

EXAMPLE 19

Synthesis of (6R,9aR)-3-[1-[3-methoxy-4-(4-methyl-1H-imidazol-1-yl) phenyl-(Z)-methylidene]-1,1-dimethyl-6-(3,4,5-trifluorophenyl)tetrahydro [1,4]oxazino[3,4-c][1,4]oxazin-4-one

[Formula 22]

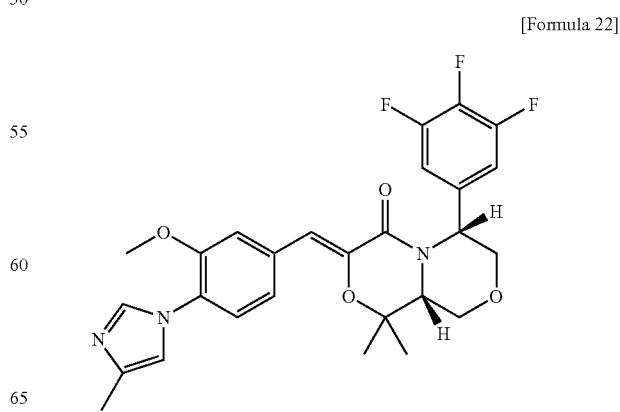

Synthesis of (3R,5R)-3-((R)-1-hydroxyethyl)-5-(3,4,5-trifluorophenyl)morpholin-4-carboxylic acid benzyl ester Saturated sodium bicarbonate aqueous solution (20 mL) and benzyl chloroformate (1.31 mL) were added to a tetrahydrofuran (20 mL) solution of (R)-1-[(3R,5R)-5-(3,4,5-trifluorophenyl)morpholin-3-yl]ethanol (2 g). After stirring the reaction solution for 16 hours at room temperature, additional benzyl chloroformate (1.33 mL) was added, and the resultant was further stirred for 20 hours. Water and ethyl acetate were added, and the organic layer was partitioned. The organic layer was washed with brine and dried over anhydrous magnesium sulfate, and the solvent was removed under a vacuum. The residue was purified by silica gel column chromatography (heptane/ethyl acetate), and the title compound (880 mg) was obtained. The physical property values are as follows.

$^1$H-NMR (CDCl$_3$) δ (ppm): 1.14 (d, J=7.2 Hz, 3H), 3.58-3.64 (m, 1H), 3.68 (dd, J=12.4, 4.0 Hz, 1H), 3.82 (dd, J=12.4, 4.0 Hz, 1H), 3.85 (dd, J=8.0, 4.0 Hz, 1H), 3.92 (d, J=12.0 Hz, 1H), 4.39 (d, J=12.8 Hz, 1H), 5.17 (brm, 1H), 5.20 (d, J=12.4 Hz, 1H), 5.27 (d, J=12.4 Hz, 1H), 7.28-7.38 (m, 7H).

Synthesis of (3R,5R)-3-acetyl-5-(3,4,5-trifluorophenyl)morpholin-4-carboxylic acid benzyl ester A tetrahydrofuran solution (15 mL) of dimethyl sulfoxide (0.22 mL) was cooled to −78° C., and oxalyl chloride (246 μL) was added dropwise into the resultant solution. The reaction solution was stirred for 5 minutes at the same temperature, and a tetrahydrofuran (5 mL) solution of (3R,5R)-3-((R)-1-hydroxyethyl)-5-(3,4,5-trifluorphenyl)morpholin-4-carboxylic acid benzyl ester (880 mg) was added dropwise. The resultant reaction solution was stirred for 1 hour at the same temperature, and triethylamine (1.54 mL) was added. The reaction solution was returned to room temperature, and stirring was continued for 1 hour. Ammonium chloride aqueous solution and ethyl acetate were added to the reaction solution, and the organic layer was partitioned, and the resultant was dried over anhydrous magnesium sulfate. The solvent was removed under a vacuum, and the resultant was purified by silica gel column chromatography (heptane/ethyl acetate), and the title compound (800 mg) was obtained. The physical property values are as follows.

$^1$H-NMR (CDCl$_3$) δ (ppm): 1.63 (s, 3H), 3.62 (dd, J=11.6, 4.4 Hz, 1H), 3.85 (dd, J=12.4, 4.4 Hz, 1H), 4.19 (d, J=12.0 Hz, 1H), 4.42 (brm, 1H), 4.65 (d, J=12.0 Hz, 1H), 5.09 (brs, 1H), 5.21 (d, J=11.6 Hz, 1H), 5.29 (d, J=11.6 Hz, 1H), 7.24-7.38 (m, 7H).

Synthesis of 1-[(3R,5R)-5-(3,4,5-trifluorophenyl)morpholin-3-yl]ethanone

An ethanol (15 mL) suspension of 10% palladium on carbon (50% water contain, 79.2 mg) and (3R,5R)-3-acetyl-5-(3,4,5-trifluorophenyl)morpholin-4-carboxylic acid benzyl ester (800 mg) was stirred for 15 minutes under a hydrogen atmosphere. The catalyst was separated by filtration on celite. The filtrate was concentrated, and the title compound (529 mg) was obtained. The physical property values are as follows.

ESI-MS; m/z 260 [M$^+$+H]

Synthesis of 2-[(3R,5R)-5-(3,4,5-trifluorophenyl)morpholin-3-yl]propane-2-ol Under a nitrogen atmosphere and at 0° C., methyl magnesium bromide (0.97 M tetrahydrofuran solution, 4.63 mL) was added dropwise into a tetrahydrofuran (25 mL) solution of 1-[(3R,5R)-5-(3,4,5-trifluorophenyl) morpholin-3-yl] ethanone (529 mg). After stirring the reaction solution for 1 hour at the same temperature, ammonium chloride aqueous solution and ethyl acetate were added, and the organic layer was partitioned. The organic layer was washed with brine and was dried over anhydrous magnesium sulfate. The solvent was removed under a vacuum, and the residue was purified by silica gel column chromatography (heptane/ethyl acetate), and the title compound (330 mg) was obtained. The physical property values are as follows.

ESI-MS; m/z 276 [M$^+$+H]. $^1$H-NMR (CDCl$_3$) δ (ppm): 1.25 (s, 6H), 2.00 (s, 1H), 2.17 (brs, 1H), 2.91 (dd, J=10.8, 3.2 Hz, 1H), 3.11 (dd, J=10.8, 10.8 Hz, 1H), 3.35 (dd, J=10.8, 10.8 Hz, 1H), 3.73 (dd, J=10.8, 3.2 Hz, 1H), 3.90-3.97 (m, 2H), 7.06 (dd, J=8.4, 6.4 Hz, 2H).

Synthesis of (6R,9aR)-1,1-dimethyl-6-(3,4,5-trifluorophenyl)tetrahydro [1,4]oxazino[3,4-c][1,4]oxazine-3,4-dione Under ice-cooling, oxalyl chloride (205 μL) was added dropwise into a chloroform (10 mL) solution of pyridine (2 mL) and 2-[(3R,5R)-5-(3,4,5-trifluorophenyl)morpholin-3-yl]propane-2-ol (330 mg). The reaction solution was stirred for 1 hour at the same temperature, and the resultant was stirred a further 2 hours at room temperature. Water was added to the reaction solution, and the organic layer was partitioned. The organic layer was washed with brine and dried over anhydrous magnesium sulfate, and the solvent was removed under a vacuum. The residue was purified by silica gel column chromatography (heptane/ethyl acetate), and the title compound (260 mg) was obtained. The physical property values are as follows.

ESI-MS; m/z 330 [M$^+$+H]. $^1$H-NMR (CDCl$_3$) δ (ppm): 1.50 (s, 3H), 1.55 (s, 3H), 3.52 (dd, J=11.6, 11.6 Hz, 1H), 3.72 (dd, J=12.0, 7.6 Hz, 1H), 4.07 (dd, J=11.2, 4.4 Hz, 1H), 4.18 (dd, J=12.4, 4.8 Hz, 1H), 4.24 (dd, J=11.2, 4.4 Hz, 1H), 4.84 (dd, J=8.0, 4.8 Hz, 1H), 7.03 (dd, J=8.0, 6.4 Hz, 2H).

Synthesis of (6R,9aR)-3-[1-[3-methoxy-4-(4-methyl-1H-imidazol-1-yl) phenyl-(Z)-methylidene]-1,1-dimethyl-6-(3,4,5-trifluorophenyl)tetrahydro [1,4]oxazino[3,4-c][1,4]oxazin-4-on Under ice cooling, L-selectride (1.14 mL, 1.02 M tetrahydrofuran solution) was added dropwise to a tetrahydrofuran solution (10 mL) containing (6R,9aR)-1,1-dimethyl-6-(3,4,5-trifluorophenyl)tetrahydro[1,4]oxazino[3,4-c][1,4]oxazin-3,4-dion (260 mg), and the reaction solution was stirred at the same temperature for 1 hour. A 5N-sodium hydroxide solution (173 μL) was added to the reaction solution and stirred at the same temperature for 20 minutes, and subsequently hydrogen peroxide solution (305 μL, 35% solution) was added and stirred at the same temperature for 20 minutes. Sodium bisulfite (328 mg) was added and stirred at room temperature for 20 minutes, and then ethyl acetate and brine were added and the organic layer was separated. The organic layer was dried over anhydrous magnesium sulfate, and the solvent was removed under a vacuum. Acetonitrile (10 mL) and triphenylphosphonium bromide (302 mg) were added to the residue and heated under reflux for 1 hour. The reaction solution was returned to room temperature, and 3-methoxy-4-(4-methyl-1H-imidazol-1-yl) benzaldehyde (206 mg) and triethylamine (240 μL) were added, and the reaction solution was stirred at room temperature for 20 hours. The solvent was removed under a vacuum, and ethyl acetate and brine were added and the organic layer was separated. The organic layer was dried over anhydrous magnesium sulfate, the solvent was removed under a vacuum, and the residue was purified with silica gel chromatography (elution solvent: heptane/ethyl acetate→ethyl acetate) to obtain the title compound (210 mg). The physical property values are as follows.

ESI-MS; m/z 514 [M$^+$+H]. $^1$H-NMR (CDCl$_3$) δ (ppm): 1.49 (s, 3H), 1.52 (s, 3H), 2.29 (d, J=1.2 Hz, 3H), 3.50 (dd, J=7.2, 7.2 Hz, 1H), 3.71 (dd, J=12.4, 7.6 Hz, 1H), 3.85 (s, 3H), 4.05 (dd, J=11.2, 4.4 Hz, 1H), 4.15 (dd, J=12.0, 4.4 Hz, 1H), 4.20 (dd, J=12.4, 4.4 Hz, 1H), 4.85 (dd, J=7.6, 4.8 Hz, 1H), 6.81 (s, 1H), 6.93 (dd, J=0.8, 0.8 Hz, 1H), 7.04 (dd, J=8.0, 6.4 Hz, 2H), 7.21 (d, J=8.4 Hz, 1H), 7.30 (dd, J=8.4, 6.4 Hz, 1H), 7.48 (d, J=1.6 Hz, 1H), 7.71 (d, J=1.2 Hz, 1H).

The present inventors performed following tests to show the usefulness of the compound of the general formula (I) of the present invention.

TEST EXAMPLE 1

Quantitation of Aβ Peptide in Neuronal Cell Culture Derived from a Rat Fetal Brain (1) Rat Primary Neuronal Cell Culture The cerebral cortex was isolated from 18-day embryos of Wister rats (Charles River Japan, Yokohama, Japan) and cultured. More specifically, under ether anesthesia, embryos were aseptically resected from pregnant rats. The brains were resected from the embryos and placed in an ice cold L-15 medium (Invitrogen Corp. Cat. #11415-064, Carlsbad, Calif., USA or SIGMA L15181 and the like). From the resected brains, the cerebral cortex was collected under a stereoscopic microscope. The collected pieces of the cerebral cortex were treated in an enzyme solution containing 0.25% trypsin (Invitrogen Corp. Cat. # 15050-065, Carlsbad, Calif. USA) and 0.01% DNase (Sigma D5025, St. Louis, Mo., USA) at 37° C. for 30 minutes to disperse cells. Then, the enzyme reaction was stopped by adding inactivated horse serum. The resultant enzyme treatment solution was centrifuged at 1500 rpm for 5 minutes to remove the supernatant. A medium (5-10 ml) was added to the obtained cell aggregates. The medium used was Neurobasal medium (Invitrogen Corp. Cat. #21103-049, Carlsbad, Calif., USA) added with 2% B27 supplement (Invitrogen Corp. Cat #17504-044, Carlsbad, Calif. USA), 25 μM 2-mercaptoethanol (2-ME, WAKO Cat. #139-06861, Osaka, Japan), 0.5 mM L-glutamine (Invitrogen Corp. Cat. #25030-081, Carlsbad, Calif., USA) and Antibiotics-Antimycotics (Invitrogen Corp. Cat. #15240-062, Carlsbad, Calif., USA) (Neurobasal/B27/2-ME). However, a media without 2-ME (Neurobasal/B27) was used when an assay was carried out. The cell aggregates mixed with the medium were pipetted gently to re-disperse the cells. The resultant cell dispersion was filtered through a 40 μm nylon mesh (cell strainer, Cat. #. 35-2340, Becton Dickinson Labware, Franklin Lakes, N.J., USA) to obtain a neuronal cell suspension by removing cell aggregates. The resultant neuronal cell suspension was diluted with the medium and seeded into poly-L or D-lysine coated 96 well polystyrene culture vessels (Falcon Cat. #. 35-3075, Becton Dickinson Labware, Franklin Lakes, N.J., USA, coated with poly-L-lysine by a following method or BIOCOAT™ cell environments Poly-D-lysine cell ware 96-well plate, Cat. #. 35-6461, Becton Dickinson Labware, Franklin Lakes, N.J., USA) at 100 μL/well so that the initial cell density was 5×10$^5$ cells/cm$^2$. The poly-L-lysine coating was carried out as follows. Using 0.15 M Borate buffer (SIGMA P2636, St. Louis, Mo., USA) solution was aseptically prepared. The resultant solution was added to 96 well polystyrene culture vessels at 100 mg/well and incubated at room temperature for 1 hour or longer or at 4° C. overnight or longer. Then the coated 96 well polystyrene culture vessels were washed with sterilized water 4 times or more, dried or rinsed with sterilized PBS or the medium and used for seeding the cells. After culturing the seeded cells were incubated at 37° C. in an incubator under a 5% CO$_2$-95% air for 1 day, the whole medium was replaced with fresh Neurobasal/B27/2-ME medium, and the incubation was continued for 3 days.

(2) Addition of Compound

At day 4 of culturing, drugs were added as follows. The whole medium was withdrawn and Neurobasal medium containing 2% B-27 but no 2-ME (Neurobasal/B27) was added to the well at 180 μL/well. A dimethylsulfoxide (hereinafter abbreviated as DMSO) solution of a test compound was diluted with Neurobasal/B27 to a 10 times concentration of the final concentration. The resultant diluted solution was added to the well at 20 μL/well and mixed well. The final DMSO concentration was to be 1% or less. Only DMSO was added to the control group.

(3) Sampling

After culturing 3 days after adding the compound, the whole medium was recovered. The medium thus obtained was used as ELISA samples. For Aβx-42 measurement, no dilution was made but for Aβx-40 measurement, samples were diluted 5 folds with the diluent attached to the ELISA kit to be subjected to the ELISA tests.

(4) Evaluation for Cell Viability

Cell viability was evaluated by the following MTT assay method. The warm medium was added to wells from which the medium had been removed at 100 μL/well, and further 8 μL/well of 8 mg/ml MTT (SIGMA M2128, St. Louis, Mo., USA) solution dissolved in D-PBS (−) (DULBECCO'S PHOSPHATE BUFFERED SALINE SIGMA D8537, St. Louis, Mo., USA) was added to each well. These 96 well polystyrene culture vessels were incubated at 37° C. in an incubator under 5% CO$_2$-95% air for 20 minutes. Then an MTT dissolving buffer was added at 100 μL/well, and after dissolving MTT formazan crystals well at 37° C. in the incubator under 5% CO$_2$-95% air, absorbance of each well at 550 nm was measured. The MTT dissolving buffer was prepared as follows. 100 g of SDS (sodium dodecylsulfate (sodium laurylsulfate), WAKO 191-07145, Osaka, Japan) was dissolved in a mixed solution of 250 ml of N,N'-dimethylformamide (WAKO 045-02916, Osaka, Japan) and 250 ml of distilled water. Further, the final pH of the solution was adjusted to about 4.7 by adding 350 μL each of concentrated hydrochloric acid and acetic acid.

When measurement was carried out, wells not seeded with cells but the medium and MTT solution were added were set as background (bkg). Each measured value was subtracted with the bkg, and the ratio (% of CTRL) to the control group (no drug treatment, CTRL) was calculated according to the following formula to compare and evaluate the cell viability.

% of $CTRL=(A550\_sample-A550\_bkg)/(A550\_CTRL-bkg)\times 100$ (wherein A550_sample: 550 nm absorbance of sample well, A550_bkg: 550 nm absorbance of background well, A550_CTRL: 550 nm absorbance of control group well)

(5) Aβ ELISA

Aβ ELISA was performed using human/rat β amyloid (42) ELISA KIT WAKO (#290-62601, Wako Pure Chemical Industries, Ltd.) or Human Amyloid beta (1-42) Assay Kit (#27711, Immuno-Biological Laboratories Co., Ltd. (IBL)). The method was conducted in accordance with the protocol (method described on a package insert) recommended by the manufacturer. Here, the Aβ standard curves were prepared by using beta-amyloid peptide 1-42, rat (Calbiochem, #171596 [Aβ42]).

(6) Results

The results are shown in Table 1 as percentage against Aβ concentration in the medium of the control group (% of CTRL).

TABLE 1

| Test compound | Aβ42 production reducing activity |
|---|---|
| Example 2 | 52 |
| Example 5 | 75 |
| Example 8 | 74 |
| Example 9 | 95 |
| Example 11 | 67 |
| Example 12 | 91 |
| Example 17 | 53 |
| Example 19 | 42 |

The results of Table 1 confirmed the Aβ42 production reducing activity by the compound of the present invention.

TEST EXAMPLE 2

Effect on Production of Amyloid β in Rat Cerebrospinal Fluid, Brain and Plasma

Animals were transferred to the laboratory the day before starting the experiment (day 0). Tentative ID numbers were painted to the tails of animals with oil based ink. Animals were measured for body weight, grouped for different treatments, and ID numbers were reattached. From the day of starting the experiment (day 1), the vehicle or test samples were orally administered to rats forcefully (5 mL/kg) once a day for 3 days. Six hours after the last administration, Nembutal (Dainippon Sumitomo Pharma Co., Ltd, Osaka) was administered intraperitoneally (50 mg/kg). Under anesthesia, the back of the neck was incised and a 25 G needle was inserted to cerebellomedullary cistern to collect about 100 μL of cerebrospinal fluid. The collected cerebrospinal fluid was placed in a tube containing 1 μL of 100 mmol/L p-ABSF to prevent degradation of Aβ and stored in ice. Subsequently, laparotomy was performed, about 2.5 mL of the blood was collected from the abdominal aorta using a heparin treated syringe and stored in ice. Finally, after decapitation, the brain was excised, rinsed lightly with physiological saline, and the wet weight of each half of the brain was measured and the brain was placed in 15 mL tube and frozen in liquid nitrogen. The excised brain samples were stored frozen until measurement. The cerebrospinal fluid was centrifuged at 4° C. at 7,000 rpm for 5 minutes, and the supernatant was recovered and Aβ was measured. The blood was centrifuged at 4° C. at 3,000 rpm for 5 minutes and the plasma was recovered and Aβ was measured.

In measuring Aβ40 and Aβ42, the cerebrospinal fluid or plasma was diluted with a diluent for the Aβ measuring kit. 70% formic acid was added to the brain tissue (right brain) at 1 mL per 100 mg wet weight and after sonication neutralized by diluting 20 fold with 0.9 mol/L Tris buffer (pH 12). The neutralized solution was used for Aβ measurement as it was.

The Aβ measurement was performed according to the manual attached to the measuring kit. That is, 100 μL each of diluted cerebrospinal fluid, diluted plasma sample or original stock solution of the neutralized brain solution was added to the Aβ 40 and Aβ 42 antibody solidified microtiter plate. In addition, 100 μL of the Aβ standard solution at each concentration was added and reacted at 4° C. overnight. After washing 5 times with a washing solution for the measuring kit, an HRP labeled secondary antigen was added and reacted at 4° C. for 1 hour. After the reaction, the plates were washed 5 times with the same washing solution, and color was developed with TMB solution and absorbance at 450 nm was measured after terminating the reaction with a stop solution by using SPECTRA MAX 190 (Molecular Devices, Sunnyvale, Calif., USA). The concentration of Aβ 40 and Aβ 42 in each sample was calculated from the standard curve.

EFFECTS OF THE INVENTION

Since the compound of the general formula (I) and (II) of the present invention or a pharmaceutically acceptable salt thereof have a production reducing activity against Aβ42 and the like, the present invention can provide a therapeutic or prophylactic agent for neurodegenerative diseases attributable to Aβ, in particular Alzheimer's disease, Down's syndrome and the like.

INDUSTRIAL APPLICABILITY

Since the compound represented by the general formula (I) of the present invention has an action of decreasing production of Aβ40 and Aβ42, it is useful, in particular, as an agent for prophylactic or therapeutic treatment of neurodegenerative diseases attributable to Aβ such as Alzheimer's disease and Down's syndrome.

The invention claimed is:

1. A compound represented by formula (I):

[Formula 1]

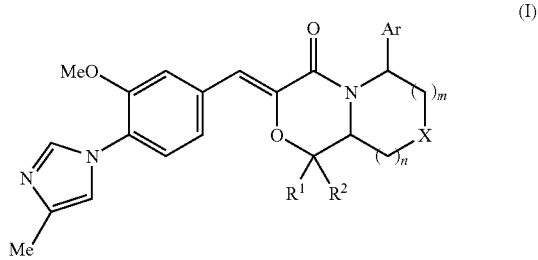

wherein (1) $R^1$ represents a C1-3 alkyl group, $R^2$ represents a hydrogen atom or a C1-3 alkyl group, or (2) $R^1$ and $R^2$, together with the carbon atom to which they are attached, form a C3-6 cycloalkyl group, Ar represents a phenyl group which may be substituted with 1 to 3 substituents that are the same or different and selected from substituent group A1 or a pyridinyl group which may be substituted with 1 to 3 substituents that are the same or different and selected from substituent group A1, X represents a methylene group which may be substituted with 1 or 2 substituents selected from substituent group A1 or a vinylene group which may be substituted with 1 or 2 substituents selected from substituent group A1, an oxygen atom, or an imino group which may be substituted with a C1-6 alkyl group or a C1-6 acyl group, and n and m are the same or different and integers of 0 to 2, or a pharmacologically acceptable salt thereof;

Substituent group A1: (1) a halogen atom, (2) a hydroxyl group, (3) a cyano group, (4) a C3-8 cycloalkyl group, (5) a C3-8 cycloalkoxy group, (6) a C1-6 alkyl group (the C1-6 alkyl group may be substituted with 1 to 5 halogen atoms or 1 to 3 C1-6 alkoxy groups), (7) an amino group which may be substituted with 1 or 2 C1-6 alkyl groups (the C1-6 alkyl group may be substituted with 1 to 5 halogen atoms), (8) a C1-6 alkoxy group (the C1-6 alkoxy group may be substituted with 1 to 5 halogen atoms), and (9) a carbamoyl group which may be substituted with 1 or 2 C1-6 alkyl groups (the C1-6 alkyl group may be substituted with 1 to 3 halogen atoms).

2. The compound or a pharmacologically acceptable salt thereof according to claim 1, wherein X represents a methylene group (the methylene group may be substituted with 1 or 2 substituents that are the same or different and selected from the group consisting of C1-6 alkyl groups and hydroxyl group), and n and m are 1.

3. The compound or a pharmacologically acceptable salt thereof according to claim 1, wherein X represents an oxygen atom, and n and m are 1.

4. The compound or a pharmacologically acceptable salt thereof according to claim 1, wherein X represents a methylene group, n is 1, and m is 0.

5. The compound or a pharmacologically acceptable salt thereof according to claim 1, wherein Ar is a phenyl group substituted with 1 to 3 halogen atoms.

6. The compound or a pharmacologically acceptable salt thereof according to claim 1, which is selected from the following group:
1) (Z)-(1R, 6R, 9aR)-3-[3-Methoxy-4-(4-methylimidazol-1-yl)benzylidene]-1-methyl-6-(3,4,5-trifluorophenyl) tetrahydro-[1,4]oxazino[3,4-c][1,4]oxazin-4-one,
2) (Z)-(1S 6R, 9aR)-3-[3-Methoxy-4-(4-methylimidazol-1-yl)benzylidene]-1-methyl-6-(3,4,5-trifluorophenyl) tetrahydro-[1,4]oxazine[3,4-c][1,4]oxazin-4-one,
3) (Z)-(1S, 6R, 9aR)-6-(3,4-Difluoro-phenyl)-3-[3-methoxy-4-(4-methylimidazol-1-yl)benzylidene]-1-methyltetrahydro-[1,4]oxazino[3,4-c][1,4]oxazin-4-one,
4) (Z)-(6S, 8aR)-6-(4-Fluorophenyl)-3-[3-methoxy-4-(4-methylimidazol-1-ylbenzylidene]-1,1-dimethyltetrahydropyrrolo[2,1-c][1,4]oxazin-4-one,
5) (Z)-(1S, 6R, 9aR)-3-[3-Methoxy-4-(4-methylimidazol-1-yl)benzylidene]-1-methyl-6-(4-chlorophenyl) hexahydropyrido[2,1-c][1,4]oxazin-4-one,
6) (Z)-(1S, 6S, 8aR)-6-(4-Fluorophenyl)-3-[3-methoxy-4-(4-methylimidazol-1-yl)benzylidene]-1-methyltetrahydropyrrolo[2,1-c][1,4]oxazin-4-one,
7) (Z)-(1R, 6S, 8aR)-6-(4-Fluorophenyl)-3-[3-methoxy-4-(4-methylimidazol-1-yl)benzylidene]-1-methyltetrahydropyrrolo[2,1-c][1,4]oxazin-4-one,
8) (Z)-(6S, 8aR)-6-(4-Chlorophenyl)-3-[3-methytoxy-4-(4-methylimidazol-1-yl)benzylidene]-1,1-dimethyltetrahydropyrrolo[2,1-c][1,4]oxazin-4-one,
9) (Z)-(1S, 6S, 8aR)-6-(4-Chlorophenyl)-3-[3-methoxy-4-(4-methylimidazol-1-yl)benzylidene]-1-methyltetrahydropyrrolo[2,1-c][1,4]oxazin-4-one,
10) (Z)-(1R, 6S, 8aR)-6-(4-Chlorophenyl)-3-[3-methoxy-4-(4-methylimidazol-1-yl)benzylidene]-1-methyltetrahydropyrrolo[2,1-c][1,4]oxazin-4-one,
11) (Z)-(6S, 8aR) -3-[3-Methoxy-4-(4-methylimidazol-1-yl)benzylidene]-1,1-dimethyl-6-(3,4,5-trifluorophenyl) tetrahydropyrrolo[2,1-c][1,4]oxazin-4-one,
12) (Z)-(1S, 6S, 8aR)-3-[3-Methoxy-4-(4-methylimidazol-1-yl)benzylidene]-1-methyl-6-(3,4,5-trifluorophenyl)tetrahydropyrrolo[2, 1-c][1,4]oxazin-4-one,
13) (Z)-(1R, 6S, 8aR)-3-[3-Methoxy-4-(4-methylimidazol- 1-yl)benzylidene]-1-methyl-6-(3,4,5-trifluorophenyl)tetrahydropyrrolo[2,1-c][1,4]oxazin-4-one,
14) (Z)-(6S, 8aR)-6-(3,4-Difluoro-phenyl)-3-[3-methoxy-4-(4-methylimidazol-1-yl)benzylidene]-1,1-dimethyltetrahydropyrrolo[2,1-c][1,4]oxazin-4-one,
15) (Z)-(1S, 6S, 8aR)-6-(3,4-Difluoro-phenyl)3-[3-methoxy-4-(4-methylimidazol-1-yl)benzylidene]-1-methyltetrahydropyrrolo[2,1-c][1,4]oxazin-4-one,
16) (Z)-(1R, 6S, 9aR)-3-[3-Methoxy-4-(4-methylimidazol- 1-yl)benzylidene]-1-methyl-6-(3,4,5-trifluorophenyl) hexahydropyrido[2,1-c][1,4]oxazin-4-one,
17) (Z)-(1S ,6S, 9aR)-3-[3-Methoxy-4-(4-methylimidazol- 1-yl)benzylidene]-1-methyl-6-(3,4,5-trifluoropheny)hexahydropyrido[2,1-c][1,4]oxazin-4-one,
18) (Z)-(6S, 8aR)-3-[3-Methoxy-4-(4-methylimidazol-1-yl)benzylidene]-1,1-cyclopropyl-6-(3,4,5-trifluoropheny)tetrahydropyrrolo[2,1-c][1,4]oxazin-4-one, and
19) (6a,9aR)-3-[1-[3-methoxy-4-(methyl-1IH -imidazol-1-yl) phenyl-(Z) -methylidene]- 1,1-dimethyl-6-(3,4,5-trifluoropheny)tetrahydro[1,4]oxazino[3,4-c][1,4]oxazin-4-one.

7. A pharmaceutical composition containing
the compound or a pharmacologically acceptable salt thereof according to any one of claims 1 to 6 as an active ingredient; and
a pharmaceutically acceptable carrier.

8. A method for treating a disease attributable to amyloid beta, selected from senile dementia, Down's syndrome and amyloidosis, said method comprising administering the compound or pharmaceutically acceptable salt thereof according to any one of claims 1 to 6 to a subject in need thereof.

* * * * *